US008563508B2

(12) United States Patent  
Jonassen et al.

(10) Patent No.: US 8,563,508 B2  
(45) Date of Patent: Oct. 22, 2013

(54) METHOD FOR PREVENTING OR REDUCING ACUTE RENAL FAILURE BY ADMINISTRATION OF THERAPEUTICALLY ACTIVE α-MSH ANALOGUES

(71) Applicant: AbbVie Inc., North Chicago, IL (US)

(72) Inventors: Thomas E. N. Jonassen, Holte (DK); Soren Nielsen, Aabyhoj (DK); Jorgen Frokiaer, Aabyhoj (DK); Bjarne Due Larsen, Roskilde (DK)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 13/847,275

(22) Filed: Mar. 19, 2013

(65) Prior Publication Data

US 2013/0217628 A1 Aug. 22, 2013

Related U.S. Application Data

(63) Continuation of application No. 12/064,923, filed as application No. PCT/DK2005/000545 on Aug. 26, 2005, now Pat. No. 8,466,104.

(51) Int. Cl.
*A61K 38/24* (2006.01)
*C07K 14/68* (2006.01)

(52) U.S. Cl.
USPC ..... 514/10.7; 514/15.4; 514/21.4; 424/185.1; 424/192.1; 424/193.1; 530/300; 530/312; 530/326

(58) Field of Classification Search
None
See application file for complete search history.

(56) References Cited

U.S. PATENT DOCUMENTS

| | | | |
|---|---|---|---|
| 4,288,627 | A | 9/1981 | Kubicek |
| 5,731,408 | A | 3/1998 | Hadley et al. |
| 7,008,925 | B1 | 3/2006 | Szardenings et al. |
| 7,414,107 | B2 | 8/2008 | Larsen |
| 7,662,732 | B2 | 2/2010 | Choi et al. |
| 7,935,786 | B2 | 5/2011 | Larsen |
| 2007/0027086 | A1 | 2/2007 | Szardenings et al. |
| 2008/0269114 | A1* | 10/2008 | Schwartz ..................... 514/12 |
| 2009/0069242 | A1 | 3/2009 | Jonassen et al. |
| 2011/0312878 | A1 | 12/2011 | Larsen |

FOREIGN PATENT DOCUMENTS

| | | |
|---|---|---|
| WO | 9117243 A1 | 11/1991 |
| WO | 9511988 A1 | 5/1995 |
| WO | 9946283 A1 | 9/1999 |
| WO | 9957148 A1 | 11/1999 |
| WO | 0104156 A1 | 1/2001 |
| WO | 0136980 A2 | 5/2001 |
| WO | 0182952 A2 | 11/2001 |
| WO | 0190140 A1 | 11/2001 |

OTHER PUBLICATIONS

Thermo Electron Corporation, technical information for N-terminal acetylation and C-terminal amidation of peptides; 2004; 2 pages.*
Vila et al. Role of hydrophobicity and solvent-mediated charge-charge interactions in stabilizing alpha-helices. Biophys J 75: 2637-2646, 1998.*
Adan R.A., et al., "Identification of Antagonists for Melanocortin MC3, MC4 and MC5 Receptors," European Journal of Pharmacology, 1994, vol. 269 (3), pp. 331-337.
Adessi C., et al., "Converting a Peptide into a Drug: Strategies to Improve Stability and Bioavailability," Current Medicinal Chemistry, 2002, vol. 9 (9), pp. 963-978. 111.
Amendment mailed Sep. 18, 2009 for U.S. Appl. No. 09/341590, filed Jul. 12, 1999.
Bagutti C., et al., "[111In]-DTPA-Labeled Analogues of Alpha-Melanocyte-Stimulating Hormone for Melanoma Targeting: Receptor Binding in Vitro and in Vivo," International Journal of Cancer, 1994, vol. 58 (5), pp. 749-755.
Barrett P., et al., "Cloning and Expression of a New Member of the Melanocyte-Stimulating Hormone Receptor Family," Journal of Molecular Endocrinology, 1994, vol. 12 (2), pp. 203-213.
Bazzani C., et al., "Protective Effect of Melanocortin Peptides in Rat Myocardial Ischemia," Journal of Pharmacology and Experimental Therapeutics, 2001, vol. 297 (3), pp. 1082-1087.
Bhardwaj R.S., et al., "Pro-Opiomelanocortin-Derived Peptides Induce IL-10 Production in Human Monocytes," Journal of Immunology, 1996, vol. 156 (7), pp. 2517-2521.
Boyfield I., et al., "Comparison of Agonist Potencies at Human Dopamine D2 and D3 Receptors, Expressed in the Same Cell Line, Using the Cytosensor Microphysiometer," Biochemical Society Transactions, 1996, vol. 24 (1), pp. 57S.
Campbell M.J., "Lipofection Reagents Prepared by a Simple Ethanol Injection Technique," BioTechniques, 1995, vol. 18 (6), pp. 1027-1032.
Canevari S., et al., "Bispecific Antibody Targeted T Cell Therapy of Ovarian Cancer: Clinical Results and Future Directions," Journal of Hematotherapy, 1995, vol. 4 (5), pp. 423-427.
Catania A., et al., "The Neuropeptide Alpha-MSH has Specific Receptors on Neutrophils and Reduces Chemotaxis in Vitro," Peptides, 1996, vol. 17 (4), pp. 675-679.
Chen G., et al., "Reduction of Ischemic Stroke in Rat Brain by Alpha Melanocyte Stimulating Hormone," Neuropeptides, 2008, vol. 42 (3), pp. 331-338.
Chen W., et al., "A Colorimetric Assay for Measuring Activation of Gs- and Gq-Coupled Signaling Pathways," Analytical Biochemistry, 1995, vol. 226 (2), pp. 349-354.
Chhajlani V., "Distribution of cDNA for Melanocortin Receptor Subtypes in Human Tissues," Biochemistry & Molecular Biology International, 1996, vol. 38 (1), pp. 73-80.

(Continued)

*Primary Examiner* — Bridget E Bunner
(74) *Attorney, Agent, or Firm* — Xu Zhang; AbbVie Inc.

(57) ABSTRACT

The invention describes peptide analogues of α-melanocyte-stimulating hormone (α-MSH), which possess an increased efficacy compared to the native α-MSH peptide. The α-MSH analogues exhibit increased anti-inflammatory effects and increased capability to prevent ischemic conditions compared to α-MSH. The invention further discloses use of the peptides for the manufacture of pharmaceutical compositions for the treatment or prophylaxis of a condition in the tissue of one or more organs of a mammal, and moreover pharmaceutical compositions.

3 Claims, 16 Drawing Sheets

(56) References Cited

OTHER PUBLICATIONS

Chhajlani V., et al., "Molecular Cloning and Expression of the Human Melanocyte Stimulating Hormone Receptor cDNA," FEBS Letters, 1992, vol. 309 (3), pp. 417-420.

Chhajlani V., et al., "Molecular Cloning of a Novel Human Melanocortin Receptor," Biochemical and Biophysical Research Communications, 1993, vol. 195 (2), pp. 866-873.

Chiao H., et al., "Alpha-Melanocyte-Stimulating Hormone Protects Against Renal Injury after Ischernia in Mice and Rats," The Journal of Clinical Investigation, 1997, vol. 99 (6), pp. 1165-1172.

Chima R.S., et al., "C-Peptide Ameliorates Kidney Injury Following Hemorrhagic Shock," Division of Critical Care Medicine, Cincinnati Children's Hospital Medical Center, 3333 Burnet Avenue, Cincinnati, OH 45229, USA Shock, 2011.

Chluba-De Tapia J., et al., "Induction of Constitutive Melanogenesis in Amelanotic Mouse Melanoma Cells by Transfection of the Human Melanocortin-1 Receptor Gene," Journal of Cell Science, 1996, vol. 109 (Pt 8), pp. 2023-2030.

Christensen C.W., et al., "Neuropharmacological Aspects of Hypothalamic Peptides and Alpha-MSH," Current Studies of Hypothalamic Function, 1978, vol. 1, pp. 182-191.

Cone R.D., "The Melanocortin Receptors: Agonists, Antagonists, and the Hormonal Control of Pigmentation," Recent Progress in Hormone Research, 1996, vol. 51, pp. 287-317.

Datta P.C., et al., "Alpha-Melanocyte-Stimulating Hormone and Behavior," Neuroscience & Biobehavioral Reviews, 1982, vol. 6 (3), pp. 297-310.

De Wied D., et al., "Neuropeptides Derived from Pro-Opiocortin: Behavioral, Physiological, and Neurochemical Effects," Physiological Reviews, 1982, vol. 62 (3), pp. 976-1059.

De Wildt D.J., et al., "Effect of Gamma 2-Melanocyte-Stimulating Hormone on Cerebral Blood Flow in Rats," Journal of Cardiovascular Pharmacology, 1995, vol. 25 (6), pp. 898-905.

Definition of "acetyl" [online], [retrieved on Mar. 23, 2012]. Retrieved from the Internet:< URL: http://www.thefreedictionary.com/acetyl+group>.

Definition of "amide" [online], [retrieved on Mar. 23, 2012]. Retrieved from the Internet:< URL: http://www.thefreedictionary.com/Amidation>.

Definition of "inhibit", Downloaded from dictionary.com on Jun. 19, 2011, 1 page.

Deng J., et al., "Alpha-Melanocyte-Stimulating Hormone Inhibits Lung Injury After Renal Ischemia/Reperfusion," American Journal of Respiratory and Critical Care Medicine, 2004, vol. 169 (6), pp. 749-756.

Desarnaud F., et al., "Molecular Cloning, Functional Expression and Pharmacological Characterization of a Mouse Melanocortin Receptor Gene," The Biochemical Journal, 1994, vol. 299 (Pt 2), pp. 367-373.

Doi K., et al., "AP214, An Analogue of Alpha-Melanocyte-Stimulating Hormone, Ameliorates Sepsis-Induced Acute Kidney Injury and Mortality," Kidney International, 2008, vol. 73 (11), pp. 1266-1274.

Doi K., et al., "AP214, An Analogue of Alpha-Melanocyte-Stimulating Hormone, Ameliorates Sepsis-Induced Acute Kidney Injury and Mortality," NIH Public Access, Kidney International Author Manuscript; Available in PMC, 2008, pp. 1-21.

Eberle A.N., "Structure-Activity Relationships of the Melanotropins," in: The Melanotropins: Chemistry, Physiology and Mechanisms of Action, Eberle, A.N., Ed., S. Larger Publishing, Basel, Switzerland, 1988, pp. 333-379. El.

Ehrlich S.D. "DNA Cloning in *Bacillus subtilis*," Proceedings of the National Academy of Sciences, 1978, vol. 75 (3), pp. 1433-1436.

Fan W., et al., "Role of Melanocortinergic Neurons in Feeding and the Agouti Obesity Syndrome," Nature, 1997, vol. 385 (6612), pp. 165-168.

Fathi Z., et al., "Cloning, Expression, and Tissue Distribution of a Fifth Melanocortin Receptor Subtype." Neurochemical Research, 1995, vol. 20 (1), pp. 107-113.

Feng J.D., et al., "Effects of Preoptic Microinjections of Alpha-MSH on Fever and Normal Temperature Control in Rabbits," Brain Research Bulletin, 1987, vol. 18 (4), pp. 473-477.

Forslin Aronsson S., et al., "Alpha-Melanocyte-Stimulating Hormone is Neuroprotective in Rat Global Cerebral lschemia," Neuropeptides, 2006, vol. 40 (1), pp. 65-75.

Friedman J.M., et al., "The Alphabet of Weight Control," 1997, vol. 385 (6612), pp. 119-120.

Fukuta M., et al., "Insulin Fragments as a Carrier for Peptide Delivery Across the Blood-Brain Barrier," Pharmaceutical Research, 1994, vol. 11 (12), pp. 1681-1688.

Gantz I., et al, "Molecular Cloning, Expression, and Characterization of a Fifth Melanocortin Receptor," Biochemical and Biophysical Research Communications, 1994, vol. 200 (3), pp. 1214-1220.

Gantz I., et al., "Molecular Cloning, Expression, and Gene Localization of a Fourth Melanocortin Receptor," Journal of Biological Chemistry, 1993, vol. 268 (20), pp. 15174-15179.

Gantz I., et al., "Molecular Cloning of a Novel Melanocortin Receptor," Journal of Biological Chemistry, 1993, vol. 268 (11), pp. 8246-8250.

Garrud P., et al., "Pituitary-Adrenal Hormones and Extinction of Rewarded Behaviour in the Rat," Physiology & Behavior, 1974, vol. 12 (1), pp. 109-119.

Gatti S., et al., "Alpha-Melanocyte-Stimulating Hormone Protects the Allograft in Experimental Heart Transplantation," Transplantation, 2002, vol. 74 (12), pp. 1678-1684.

Giblin M.F., et al., "Synthesis and Characterization of Rhenium-Complexed Alpha-Melanotropin Analogs," Bioconjugate Chemistry, 1997, vol. 8 (3), pp. 347-353.

Gilbert W., et al., "Useful Proteins from Recombinant Bacteria," Scientific American, 1980, vol. 242 (4), pp. 74-94.

Giuliani D., et al., "Selective Melanocortin MC4 Receptor Agonists Reverse Haemorrhagic Shock and Prevent Multiple Organ Damage," British Journal of Pharmacology, 2007, vol. 150 (5), pp. 595-603.

Gong H., et al., "EPO and Alpha-MSH Prevent Ischemia/Reperfusion-Induced Down-Regulation of AQPs and Sodium Transporters in Rat Kidney," Kidney International, 2004, vol. 66 (2), pp. 683-695.

Gonindard C., et al., "The Administration of an Alpha-MSH Analogue Reduces the Serum Release of IL-1 Alpha and TNF Alpha Induced by the Injection of a Sublethal Dose of Lipopolysaccharides in the BALB/c Mouse," Pigment Cell Research, 1996, vol. 9 (3), pp. 148-153.

Grieco P., et al., "Novel Alpha-Melanocyte Stimulating Hormone Peptide Analogues with High Candidacidal Activity," Journal of Medicinal Chemistry, 2003, vol. 46 (5), pp. 850-855.

Griffon N., et al., "Molecular Cloning and Characterization of the Rat Fifth Melanocortin Receptor," Biochemical and Biophysical Research Communications, 1994, vol. 200 (2), pp. 1007-1014.

Gruber K.A., et al., "ACTH-(4-10) through Gamma-MSH: Evidence for a New Class of Central Autonomic Nervous System-Regulating Peptides," American Journal of Physiology, 1989, vol. 257 (4 Pt 2), pp. R681-R694.

Guo Z., et al., "3'-End-Forming Signals of Yeast mRNA," Molecular and Cellular Biology, 1995, vol. 15 (11), pp. 5983-5990.

Hartmeyer M., et al., "Human Dermal Microvascular Endothelial Cells Express the Melanocortin Receptor Type 1 and Produce Increased Levels of IL-8 upon Stimulation with Alpha-Melanocyte-Stimulating Hormone," Journal of Immunology, 1997, vol. 159 (4), pp. 1930-1937.

Hassoun H.T., et al., "Alpha-Melanocyte-Stimulating Hormone Protects against Mesenteric Ischemia-Reperfusion Injury," American Journal of Physiology—Gastrointestinal and Liver Physiology, 2002, vol. 282 (6), pp. G1059-G1068.

Hill C., et al., "The Effects of Acute and Chronic Alpha Melanocyte Stimulating Hormone (alphaMSH) on Cardiovascular Dynamics in Conscious Rats," Peptides, 2002, vol. 23 (9), pp. 1625-1630.

Hiltz M.E., et al., "Anti-Inflammatory Activity of Alpha-MSH(11-13) Analogs: Influences of Alteration in Stereochemistry," Peptides, 1991, vol. 12 (4), pp. 767-771.

Hnatowich M.R., et al., "ACTH Receptors in Nervous Tissue. High Affinity Binding-Sequestration of [125I]Phe2,Nle4 ACTH 1-24 in Homogenates and Slices From Rat Brain," Canadian Journal of Physiology and Pharmacology, 1989, vol. 67 (6), pp. 568-576.

(56) References Cited

OTHER PUBLICATIONS

Hol E.M., et al., "Protection by an ACTH4-9 Analogue Against the Toxic Effects of Cisplatin and Taxol on Sensory Neurons and Glial Cells in Vitro," Journal of Neuroscience Research, 1994, vol. 39 (2), pp. 178-185.

Hruby V.J., et al., "Cyclic Lactam Alpha-Melanotropin Analogues of Ac-Nle4-Cyclo[Asp5, D-Phe7,Lys10] Alpha-Melanocyte-Stimulating Hormone-(4-10)-NH2 with Bulky Aromatic Amino Acids at Position 7 Show High Antagonist Potency and Selectivity at Specific Melanocortin Receptors," Journal of Medicinal Chemistry, 1995, vol. 38 (18), pp. 3454-3461.

Huang T.M., et al., "Preoperative Proteinuria Predicts Adverse Renal Outcomes After Coronary Artery Bypass Grafting," Journal of the American Society of Nephrology, 2011, vol. 22 (1), pp. 156-163.

Huh S.K., et al., "The Protective Effects of Alpha-Melanocyte Stimulating Hormone on Canine Brain Stem Ischemia," Neurosurgery, 1997, vol. 40 (1), pp. 132-140.

Humphreys M.H., et al., "Cardiovascular Effects of Melanocortins," European Journal of Pharmacology, 2011, vol. 660 (1), pp. 43-52.

Jung E.J., et al., "Protective Effect of Alpha-Melanocyte-Stimulating Hormone on Pancreas Islet Cell against Peripheral Blood Mononuclear Cell-Mediated Cytotoxicity in Vitro," Transplantation Proceedings, 2007, vol. 39 (5), pp. 1604-1606.

Kawaguchi M., et al., "Inflammasome Activation of Cardiac Fibroblasts is Essential for Myocardial Ischemia/Reperfusion Injury," Circulation, 2011, vol. 123 (6), pp. 594-604.

Klein M.C., et al., "Pressor and Cardioaccelerator Effects of Gamma MSH and Related Peptides," Life Sciences, 1985, vol. 36 (8), pp. 769-775.

Knittel J.J., et al., "Structure-Activity Studies of Highly Potent Cyclic [Cys4,Cys10]Melanotropin Analogues," Journal of Medicinal Chemistry, 1983, Vol, 26 (2), pp. 125-129.

Kohda Y., et al., "Alpha-Melanocyte-Stimulating Hormone and Acute Renal Failure," Current Opinion in Nephrology and Hypertension, 1998, vol. 7 (4), pp. 413-417.

Kullmann W., "Proteases as Biocatalysts for the Synthesis of Model Peptides", in: Enzymatic Peptide Synthesis, Chapter 7, CRC Press, Boca Raton, Florida, 1987, pp. 41-59.

Labbe O., et al., "Molecular Cloning of a Mouse Melanocortin 5 Receptor Gene Widely Expressed in Peripheral Tissues," Biochemistry, 1994, vol. 33 (15), pp. 4543-4549.

Lands S., et al., "The Biochemistry of Melanotropin, Agents," Pharmacological Reviews, 1967, vol. 19 (1), pp. 1-20.

Larsen, et al., "Structural Inducing Probes (SIP)—Blow New Hope into the General Use of Peptides as Drugs," Abstract from Peptides 2000, Proceedings of the European Peptide Symposium 26th, Abstract.

Lichtensteiger W., et al., "Pre- and Postnatal Ontogeny of [125I]Nle4,D-Phe7-Alpha-MSH Binding Sites in Rat Brain," Annals of the New York Academy of Sciences, 1993, vol. 680, pp. 652-654.

Lin S.Y., et al., "A Gamma-Melanocyte Stimulating Hormone-Like Peptide Causes Reflex Natriuresis after Acute Unilateral Nephrectomy," Hypertension, 1987, vol. 10 (6), pp. 619-627.

Lipton J.M., et al., "Anti-Inflammatory Actions of the Neuroimmunomodulator Alpha-MSH," Immunology Today, 1997, vol. 18 (3), pp. 140-145.

Liu C.F., et al., "Orthogonal Ligation of Unprotected Peptide Segments through Pseudoproline Formation for the Synthesis of HIV-1 Protease Analogs," Journal of the American Chemical Society, 1996, vol. 118, pp. 307-312.

Low M.J., et al., "Receptors for the Melanocortin Peptides in the Central Nervous System," Current Opinion in Endocrinology and Diabetes, 1994, pp. 79.

Luger T.A., et al., "Alfa-MSH Related Peptides: A New Class of Anti-Inflammattory and Immunomodulating Drugs," Annals of the Rheumatic Diseases, 2007, vol. 66 (Suppl. 3), pp. iii52-iii55.

Luger T.A., et al., "The Proopiomelanocortin System in Cutaneous Neuroimmunomodulation. An Introductory Overview," New York Academy of Sciences Conference on Cutaneous Neuroimmunomodulation: The Proopiomelanocortin System, 1998, Annals New York Academy of Sciences, pp. xi-Xiii.

Luger T.A., et al., "The Role of Alpha-Melanocyte-Stimulating Hormone in Cutaneous Biology," Journal of Investigative Dermatology Symposium Proceedings, 1997, vol. 2 (1), pp. 87-93.

Minutoli L., et al., "Melanocortin 4 Receptor Activation Protects against Testicular Ischemia-Reperfusion Injury by Triggering the Cholinergic Antiinflammatory Pathway," Endocrinology, 2011, vol. 152 (10), pp. 3852-3861.

Mioni C., et al.. "Further Evidence that Melanocortins Prevent Myocardial Reperfusion Injury by Activating Melanocortin MC3 Receptors," European Journal of Pharmacology, 2003, vol. 477 (3), pp. 227-234.

Mountjoy K.G., et al., "Localization of the Melanocortin-4 Receptor (MC4-R) in Neuroendocrine and Autonomic Control Circuits in the Brain," Molecular Endocrinology, 1994, vol. 8 (10), pp. 1298-1308.

Mountjoy K.G., et al., "The Cloning of a Family of Genes the Encode the Melanocortin Receptors," Science, 1992, vol. 257 (5074), pp. 1248-1251.

Mukherji B., et al., "Immunobiology and Immunotherapy of Melanoma," Current Opinion in Oncology, 1995, vol. 7 (2), pp. 159-161.

Murphy, et al., Intensive Care Med, Sep. 1996, vol. 22 (Suppl, 3). 5336, poster 219.

Murphy J.R., et al., "Genetic Construction, Expression, and Melanoma-Selective Cytotoxicity of a Diphtheria Toxin-Related Alpha-Melanocyte-Stimulating Hormone Fusion Protein," Proceedings of the National Academy of Sciences, 1986, vol. 83 (21), pp. 8258-8262.

Ni X.P., et al., "Central Receptors Mediating the Cardiovascular Actions of Melanocyte Stimulating Hormones," Journal of Hypertension, 2006, vol. 24 (11), pp. 2239-2246.

Nordstedt C., et al., "A Modification of a Protein-Binding Method for Rapid Quantification of cAMP in Cell-Culture Supernatants and Body Fluid," Analytical Biochemistry, 1990, vol. 189 (2), pp. 231-234.

Odonohue T.L., et al., "Comparison of Biological and Behavioral Activities of Alpha- and Gamma-Melanocyte Stimulating Hormones," Peptides, 1981, vol. 2 (1), pp. 101-104.

O'Donohue T.L., et al., "The Opiomelanotropinergic Neuronal and Endocrine Systems," Peptides, 1982, vol. 3 (3). pp. 353-395.

O'Hare K.B., et al., "Polymeric Drug-Carriers Containing Doxorubicin and Melanocyte-Stimulating Hormone: In Vitro and in Vivo Evaluation Against Murine Melanoma," Journal of Drug Targeting, 1993, vol. 1 (3), pp. 217-229.

Pardridge W.M., "Recent Developments in Peptide Drug Delivery to the Brain," Pharmacology & Toxicology, 1992, vol. 71 (1), pp. 3-10.

Patel D., et al., "Peptide Targeting and Delivery Across the Blood-Brain Barrier Utilizing Synthetic Triglyceride Esters: Design, Synthesis, and Bioactivity," Bioconjugate Chemistry, 1997, vol. 8 (3), pp. 434-441.

Prokai-Tatrai K., et al., "Brain-Targeted Delivery of a Leucine-Enkephalin Analogue by Retrometabolic Design," Journal of Medicinal Chemistry, 1996, vol. 39 (24), pp. 4775-4782.

Prusis P., et al., "A Three Dimensional Model for the Interaction of MSH with the Melanocortin-1 Receptor," Biochemical and Biophysical Research Communications, 1995, vol. 210 (1), pp. 205-210.

Rajora N,, et al., "Alpha-MSH Modulates Experimental Inflammatory Bowel Disease," Peptides, 1997, vol. 18 (3), pp. 381-385.

Rajora N., et al., "Alpha-MSH Modulates Local and Circulating Tumor Necrosis Factor-Alpha in Experimental Brain Inflammation," The Journal of Neuroscience, 1997, vol. 17 (6), pp. 2181-2186.

Riedle S., et al., "In Vivo Activation and Expansion of T Cells by a Bi-Specific Antibody Abolishes Metastasis Formation of Human Melanoma Cells in SCID Mice," International Journal of Cancer, 1998, vol. 75 (6), pp. 908-918.

Rizzi A., et al., "Pharmacological Characterization of the Novel Nociceptin/Orphanin FQ Receptor Ligand, ZP120: In Vitro and in Vivo Studies in Mice," British Journal of Pharmacology, 2002, vol. 137 (3), pp. 369-374.

Romanos M.A., et al., "Foreign Gene Expression in Yease: A Review," Yeast, 1992, vol. 8 (6), pp. 423-488.

Roselli-Rehfuss L:, et al., "Identification of a Receptor for Gamma Melanotropin and Other Proopiomelanocortin Peptides in the Hypo-

(56) References Cited

OTHER PUBLICATIONS thalamus and Limbic System," Proceedings of the National Academy of Sciences, 1993, vol. 90 (19), pp. 8856-8860.
Saito Y., et al., "Vector-Mediated Delivery of 125I-labeled Beta-Amyloid Peptide A Beta 1-40 through the Blood-Brain Barrier and Binding to Alzheimer Disease Amyloid of the A Beta 1-40/Vector Complex," Proceedings of the National Academy of Sciences, 1995, vol. 92 (22), pp. 10227-10231.
Sawyer T.K., et al., "4-Norleucine, 7-D-Phenylalanine-Alpha-Melanocyte-Stimulating Hormone: A Highly Potent Alpha-Melanotropin with Ultralong Biological Activity," Proceedings of the National Academy of Sciences, 1980, vol. 77 (10), pp. 5754-5758.
Sawyer T.K., et al., "[half-Cys4,half-Cys10]-Alpha-Melanocyte-Stimulating Hormone: A Cyclic Alpha-Melanotropin Exhibiting Superagonist Biological Activity," Proceedings of the National Academy of Sciences, 1982, vol. 79 (6), pp. 1751-1755.
Schioth H.B., et al., "Binding of Cyclic and Linear MSH Core Peptides to the Melanocortin Receptor Subtypes," European Journal of Pharmacology, 1997, vol. 319 (2-3), pp. 369-373.
Schioth H.B., et al., "Characterisation of Melanocortin Receptor Subtypes by Radioligand Binding Analysis," European Journal of Pharmacology, 1995, vol. 288 (3), pp. 311-317.
Schioth H.B., et al., "Characterisation of the Melanocortin 4 Receptor by Radioligand Binding," Pharmacology & Toxicology, 1996, vol. 79 (3), pp. 161-165.
Schioth H.B., et al., "Selective Properties of C- and N-Terminals and Core Residues of the Melanocyte-Stimulating Hormone on Binding to the Human Melanocortin Receptor Subtypes," European Journal of Pharmacology, 1998, vol. 349 (2-3), pp. 359-366.
Schioth H.B., et al., "Selectivity of Cyclic [D-Nal7] and [D-Phe7] Substituted MSH Analogues for the Melanocortin Receptor Subtypes," Peptides, 1997; vol. 18 (7), pp. 1009-1113.
Schioth H.B., et al,, "Expression of Functional Melanocortin 1 Receptors in Insect Cells," Biochemical and Biophysical Research Communications, 1996, vol. 221 (3), pp. 807-814.
Schioth H.B., et al., "Major Pharmacological Distinction of the ACTH Receptor from Other Melanocortin Receptors," Life Sciences, 1996, vol. 59 (10), pp. 797-801.
Siegrist W., et al., "Melanocortins and their Implication in Melanoma," Trends in Endocrinology & Metabolism, 1995, vol. 6 (4), pp. 115-120.
Simmons M.N., et al., "Alpha-Melanocyte Stimulating Hormone Analogue AP214 Protects against Ischemia Induced Acute Kidney Injury in a Porcine Surgical Model," Journal of Urology, 2010, vol. 183 (4), pp. 1625-1629.
Simpson E.R., et al., "Regulation of the Synthesis of Steroidogenic Enzymes in Adrenal Cortical Cells by ACTH," Annual Review of Physiology, 1988, vol. 50, pp. 427-440.
Solca F.F., et al., "B16-G4F Mouse Melanoma Cells: An MSH Receptor-Deficient Cell Clone," FEBS Letters, 1993, vol. 322 (2), pp. 177-180.
Star R.A., et al., "Evidence of Autocrine Modulation of Macrophage Nitric Oxide Synthase by Alpha-Melanocyte-Stimulating Hormone," Proceedings of the National Academy of Sciences, 1995, vol. 92 (17), pp. 8016-8020.
Steinbruchel D., et al., "Poster: AP214 Improves Long-Term (3 Month) Outcome on Composite Endpoint of Death, RRT or Reduced Kidney Function in Patients Undergoing Cardiac Surgery in a Phase 2 Clinical Trial," Journal of the American Society of Nephrology.
Steinbruchel D., et al., "TH-P0363: Safety, Pharmacokinetics and Efficacy of AP214, a Novel Melanocortin Receptor Agonists, in Patients Undergoing Cardiac Surgery on Cardiopulmonary Bypass," Journal of the American Society of Nephrology, 2011, pp. 196A.
Szardenings M., et al., "New Highly Specific Agonistic Peptides for Human Melanocortin MC(1) Receptor," Peptides, 2000, vol. 21 (2), pp. 239-243.
Szardenings M., et al., "Phage Display Selection on Whole Cells Yields a Peptide Specific for Melanocortin Receptor 1," The Journal of Biological Chemistry, 1997, vol. 272 (44), pp. 27943-27948.

Tai M.H., et al., "Role of Nitric Oxide in Alpha-Melanocyte-Stimulating Hormone-Induced Hypotension in the Nucleus Tractus Solitarii of the Spontaneously Hypertensive Rats," Journal of Pharmacology and Experimental Therapeutics, 2007, vol. 321 (2), pp. 455-461.
Tamai I., et al., "Structure-Internalization Relationship for Adsorptive-Mediated Endocytosis of Basic Peptides at the Blood-Brain Barrier," Journal of Pharmacology and Experimental Therapeutics, 1997, vol. 280 (1), pp. 410-415.
Tatro J.B., et al., "Heterogeneity of Brain Melanocortin Receptors Suggested by Differential Ligand Binding in Situ," Brain Research, 1994, vol. 635 (1-2), pp. 148-158.
Tatro J.B., et al, "Interaction of an Alpha-Melanocyte-Stimulating Hormone-Diphtheria Toxin Fusion Protein with Melanotropin Receptors in Human Melanoma Metastases," Cancer Research, 1992, vol. 52 (9), pp. 2545-2548.
Tatro J.B., et al., "Specific Receptors for Alpha-Melanocyte-Stimulating Hormone are Widely Distributed in Tissues of Rodents," Endocrinology, 1987, vol. 121 (5), pp. 1900-1907.
Thielemans K.M., "Immunotherapy with Bispecific Antibodies," Verh K Acad Geneeskd Belg, 1995, vol. 57 (3), pp. 229-248.
Thornwall M., et al., "Immunohistochemical Detection of the Melanocortin 1 Receptor in Human Testis, Ovary and Placenta using Specific Monoclonal Antibody," Hormone Research, 1997, vol. 48 (5), pp. 215-218.
Toth I., "A Novel Chemical Approach to Drug Delivery: Lipidic Amino Acid Conjugates," Journal of Drug Targeting, 1994, vol. 2 (3), pp. 217-239.
Vanetti M., et al., "Molecular Cloning of a Bovine MSH Receptor Which is Highly Expressed in the Testis," FEBS Letters, 1994, vol. 348 (3), pp. 268-272.
Vecsernyes M., et al., "The Administration of Alpha-Melanocyte-Stimulating Hormone Protects the Ischemic/Reperfused Myocardium," European Journal of Pharmacology, 2003, vol. 470 (3), pp. 177-183.
Wiegant V.M., et al., "Intracerebroventricular ACTH Activates the Pituitary-Adrenal System:Dissociation from a Behavioral Response," Life Sciences, 1979, vol. 25 (21), pp. 1791-1796.
Wikberg J.E., et al., "New Aspects on the Melanocortins and their Receptors," Pharmacological Research, 2000, vol. 42 (5), pp. 393-420.
Wikberg J.E., "Melanocortin Receptors: Perspectives for Novel Drugs," European Journal of Pharmacology, 1999, vol. 375 (1-3), pp. 295-310.
Wong K.Y., et al., "A Potential Mechanism of Local Anti-Inflammatory Action of Alpha-Melanocyte-Stimulating Hormone Within the Brain: Modulation of Tumor Necrosis Factor-Alpha Production by Human Astrocytic Cells," Neuroimmunomodulation, 1997, vol. 4 (1), pp. 37-41.
Wu D., et al., "Central Nervous Syte,m Pharmacologic Effect in Conscious Rats after Intravenous Injection of a Biotinylated Vasoactive Intestinal Peptide Analog Coupled to a Blood-Brain Barrier Drug Delivery System," Journal of Pharmacology and Experimental Therapeutics, 1996, vol. 279 (1), pp. 77-83.
Xia Y., et al., "Expression of Melanocortin 1 Receptor in Periaqueductal Gray Matter," Neuroreport, 1995, vol. 6 (16), pp. 2193-2196.
Xia Y., et al., "Immunological Localisation of Melanocortin 1 Receptor on the Cell Surface of WM266-4 Human Melanoma Cells," Cancer Letters, 1996, vol. 98 (2), pp. 157-162.
Zlokovic B.V., "Cerebrovascular Permeability to Peptides: Manipulations of Transport Systems at the Blood-Brain Barrier," Pharmaceutical Research, 1995, vol. 12 (10), pp. 1395-1406.
Zou L., et al., "Delayed Administration of Alpha-Melanocyte-Stimulating Hormone or Combined Therapy with BAY 11-7085 Protects Against Gut Ischemia-Reperfusion Injury," Shock, 2003, vol. 20 (5), pp. 469-475.
Gaberc-Porekar, V. et al., "Histidines in affinity tags and surface clusters for immobilized metal-ion affinity chromatography of trimeric tumor necrosis factor alpha," J. Chromat. A. (1999) 852:117-128.

(56) References Cited

OTHER PUBLICATIONS

Goel, A. et al., "Relative position of the hexahistidine tag effects binding properties of a tumor-associated single-chain Fv construct," Biochem. Biophys. Acta (2000) 1523:13-20.

Hang, Q. et al., "Cloning, expression, and biochemical characterization of hexahistidine-tagged terminase proteins," J. Biol. Chem. (1999) 274(22)15305-15314.

Jo, S.K. et al., "Pharmacologic treatment of acute kidney injury: why drugs haven't worked and what is on the horizon," Clin. J. Am. Soc. Nephrol. (2007) 2:356-365.

Lieberthal, W. et al., "Acute renal failure. II. Experimental models of acute renal failure: imperfect but indispensable," Am. J. Physiol. Renal Physiol. (2000) 278:F1-F12.

Moritz, O.L. et al., "A functional rhodopsin-green fluorescent protein fusion protein localizes correctly in transgenic xenopus laevis retinal rods and is expressed in a time-dependent pattern," J. Biol. Chem. (2001) 276(30):28242-28251.

Ronco, C. et al., "Potential interventions in sepsis-related acute kidney injury," Clin. J. Am. Soc. Nephrol. (2008) 3:531-544.

Rosen, S. et al., "Difficulties in understanding human 'acute tubular necrosis': limited data and flawed animal models," Kidney Int'l (2001) 60:1220-1224.

Terpe, K., "Overview of tag protein fusions: from molecular and biochemical fundamentals to commercial systems," Appl. Microbiol. Biotechnol. (2003) 60:523-533.

Wu, J. et al., "Hexahistidine (His6)-tag dependent protein dimerization: a cautionary tale," Acta Biochimica Polonica (1999) 46(3):591-599.

Yewdell, J.W. et al., "Out with the old, in with the new? Comparing methods for measuring protein degradation," Cell Biol. Int. (2011) 35:6 pages.

\* cited by examiner

*: different from vehicle

*: different from vehicle

SEQUENCE LISTING

```
<160> NUMBER OF SEQ ID NOS: 101

<210> SEQ ID NO 1
<211> LENGTH: 19
<212> TYPE: PRT
<213> ORGANISM: Artificial sequence
<220> FEATURE:
<223> OTHER INFORMATION: alpha-MSH analogue

<400> SEQUENCE: 1

Lys Lys Lys Lys Lys Lys Ser Tyr Ser Met Glu His Phe Arg Trp Gly
1               5                   10                  15

Lys Pro Val

<210> SEQ ID NO 2
<211> LENGTH: 19
<212> TYPE: PRT
<213> ORGANISM: Artificial sequence
<220> FEATURE:
<223> OTHER INFORMATION: alpha-MSH analogue

<400> SEQUENCE: 2

Glu Glu Glu Glu Glu Glu Ser Tyr Ser Met Glu His Phe Arg Trp Gly
1               5                   10                  15

Lys Pro Val

<210> SEQ ID NO 3
<211> LENGTH: 19
<212> TYPE: PRT
<213> ORGANISM: Artificial sequence
<220> FEATURE:
<223> OTHER INFORMATION: alpha-MSH analogue
<220> FEATURE:
<221> NAME/KEY: MUTAGEN
<222> LOCATION: (19)..(19)
<223> OTHER INFORMATION: d-valine

<400> SEQUENCE: 3

Lys Lys Lys Lys Lys Lys Ser Tyr Ser Met Glu His Phe Arg Trp Gly
1               5                   10                  15

Lys Pro Val
```

```
<210> SEQ ID NO 4
<211> LENGTH: 19
<212> TYPE: PRT
<213> ORGANISM: Artificial sequence
<220> FEATURE:
<223> OTHER INFORMATION: alpha-MSH analogue
<220> FEATURE:
<221> NAME/KEY: MUTAGEN
<222> LOCATION: (19)..(19)
<223> OTHER INFORMATION: d-valine

<400> SEQUENCE: 4

Glu Glu Glu Glu Glu Glu Ser Tyr Ser Met Glu His Phe Arg Trp Gly
1               5                   10                  15

Lys Pro Val

<210> SEQ ID NO 5
<211> LENGTH: 19
<212> TYPE: PRT
<213> ORGANISM: Artificial sequence
<220> FEATURE:
<223> OTHER INFORMATION: alpha-MSH analogue
<220> FEATURE:
<221> NAME/KEY: MUTAGEN
<222> LOCATION: (10)..(10)
<223> OTHER INFORMATION: Xaa=Nle

<400> SEQUENCE: 5

Lys Lys Lys Lys Lys Lys Ser Tyr Ser Xaa Glu His Phe Arg Trp Gly
1               5                   10                  15

Lys Pro Val

<210> SEQ ID NO 6
<211> LENGTH: 19
<212> TYPE: PRT
<213> ORGANISM: Artificial sequence
<220> FEATURE:
<223> OTHER INFORMATION: alpha-MSH analogue
<220> FEATURE:
<221> NAME/KEY: MUTAGEN
<222> LOCATION: (10)..(10)
<223> OTHER INFORMATION: Xaa=Nle
<220> FEATURE:
<221> NAME/KEY: MUTAGEN
<222> LOCATION: (13)..(13)
<223> OTHER INFORMATION: d-phenylalanine

<400> SEQUENCE: 6

Glu Glu Glu Glu Glu Glu Ser Tyr Ser Xaa Glu His Phe Arg Trp Gly
1               5                   10                  15

Lys Pro Val

<210> SEQ ID NO 7
<211> LENGTH: 19
<212> TYPE: PRT
<213> ORGANISM: Artificial sequence
<220> FEATURE:
<223> OTHER INFORMATION: alpha-MSH analogue
<220> FEATURE:
<221> NAME/KEY: MUTAGEN
<222> LOCATION: (10)..(10)
<223> OTHER INFORMATION: Xaa=Nle
<220> FEATURE:
<221> NAME/KEY: MUTAGEN
<222> LOCATION: (13)..(13)
<223> OTHER INFORMATION: d-phenylalanine
<220> FEATURE:
<221> NAME/KEY: MUTAGEN
<222> LOCATION: (19)..(19)
<223> OTHER INFORMATION: d-valine
```

```
<400> SEQUENCE: 7

Lys Lys Lys Lys Lys Lys Ser Tyr Ser Xaa Glu His Phe Arg Trp Gly
1               5                   10                  15

Lys Pro Val

<210> SEQ ID NO 8
<211> LENGTH: 19
<212> TYPE: PRT
<213> ORGANISM: Artificial sequence
<220> FEATURE:
<223> OTHER INFORMATION: alpha-MSH analogue
<220> FEATURE:
<221> NAME/KEY: MUTAGEN
<222> LOCATION: (10)..(10)
<223> OTHER INFORMATION: Xaa=Nle
<220> FEATURE:
<221> NAME/KEY: MUTAGEN
<222> LOCATION: (13)..(13)
<223> OTHER INFORMATION: d-phenylalanine
<220> FEATURE:
<221> NAME/KEY: MUTAGEN
<222> LOCATION: (19)..(19)
<223> OTHER INFORMATION: d-valine

<400> SEQUENCE: 8

Glu Glu Glu Glu Glu Glu Ser Tyr Ser Xaa Glu His Phe Arg Trp Gly
1               5                   10                  15

Lys Pro Val

<210> SEQ ID NO 9
<211> LENGTH: 19
<212> TYPE: PRT
<213> ORGANISM: Artificial sequence
<220> FEATURE:
<223> OTHER INFORMATION: alpha-MSH analogue
<220> FEATURE:
<221> NAME/KEY: VARSPLIC
<222> LOCATION: (10)..(10)
<223> OTHER INFORMATION: Xaa=NIe
<220> FEATURE:
<221> NAME/KEY: MUTAGEN
<222> LOCATION: (13)..(13)
<223> OTHER INFORMATION: beta-2-naphthyl-d-alanine

<400> SEQUENCE: 9

Lys Lys Lys Lys Lys Lys Ser Tyr Ser Xaa Glu His Xaa Arg Trp Gly
1               5                   10                  15

Lys Pro Val

<210> SEQ ID NO 10
<211> LENGTH: 19
<212> TYPE: PRT
<213> ORGANISM: Artificial sequence
<220> FEATURE:
<223> OTHER INFORMATION: alpha-MSH analogue
<220> FEATURE:
<221> NAME/KEY: MUTAGEN
<222> LOCATION: (10)..(10)
<223> OTHER INFORMATION: Xaa=NIe
<220> FEATURE:
<221> NAME/KEY: MUTAGEN
<222> LOCATION: (13)..(13)
<223> OTHER INFORMATION: beta-2-naphthyl-d-alanine

<400> SEQUENCE: 10

Glu Glu Glu Glu Glu Glu Ser Tyr Ser Xaa Glu His Xaa Arg Trp Gly
1               5                   10                  15

Lys Pro Val
```

```
<210> SEQ ID NO 11
<211> LENGTH: 19
<212> TYPE: PRT
<213> ORGANISM: Artificial sequence
<220> FEATURE:
<223> OTHER INFORMATION: alpha-MSH analogue
<220> FEATURE:
<221> NAME/KEY: MUTAGEN
<222> LOCATION: (10)..(10)
<223> OTHER INFORMATION: Xaa=NIe
<220> FEATURE:
<221> NAME/KEY: MUTAGEN
<222> LOCATION: (13)..(13)
<223> OTHER INFORMATION: beta-2-naphthyl-d-alanine
<220> FEATURE:
<221> NAME/KEY: MUTAGEN
<222> LOCATION: (19)..(19)
<223> OTHER INFORMATION: d-valine

<400> SEQUENCE: 11

Lys Lys Lys Lys Lys Lys Ser Tyr Ser Xaa Glu His Xaa Arg Trp Gly
1               5                   10                  15

Lys Pro Val

<210> SEQ ID NO 12
<211> LENGTH: 19
<212> TYPE: PRT
<213> ORGANISM: Artificial sequence
<220> FEATURE:
<223> OTHER INFORMATION: alpha-MSH analogue
<220> FEATURE:
<221> NAME/KEY: MUTAGEN
<222> LOCATION: (10)..(10)
<223> OTHER INFORMATION: Xaa=NIe
<220> FEATURE:
<221> NAME/KEY: MUTAGEN
<222> LOCATION: (13)..(13)
<223> OTHER INFORMATION: beta-2-naphthyl-d-alanine
<220> FEATURE:
<221> NAME/KEY: MUTAGEN
<222> LOCATION: (19)..(19)
<223> OTHER INFORMATION: d-valine

<400> SEQUENCE: 12

Glu Glu Glu Glu Glu Glu Ser Tyr Ser Xaa Glu His Xaa Arg Trp Gly
1               5                   10                  15

Lys Pro Val

<210> SEQ ID NO 13
<211> LENGTH: 19
<212> TYPE: PRT
<213> ORGANISM: Artificial sequence
<220> FEATURE:
<223> OTHER INFORMATION: alpha-MSH analogue

<400> SEQUENCE: 13

Lys Lys Lys Lys Lys Lys Ser Ser Ile Ile Ser His Phe Arg Trp Gly
1               5                   10                  15

Lys Pro Val

<210> SEQ ID NO 14
<211> LENGTH: 19
<212> TYPE: PRT
<213> ORGANISM: Artificial sequence
<220> FEATURE:
<223> OTHER INFORMATION: alpha-MSH analogue

<400> SEQUENCE: 14
```

```
Glu Glu Glu Glu Glu Glu Ser Ser Ile Ile Ser His Phe Arg Trp Gly
1               5                   10                  15

Lys Pro Val

<210> SEQ ID NO 15
<211> LENGTH: 19
<212> TYPE: PRT
<213> ORGANISM: Artificial sequence
<220> FEATURE:
<223> OTHER INFORMATION: alpha-MSH analogue
<220> FEATURE:
<221> NAME/KEY: MUTAGEN
<222> LOCATION: (19)..(19)
<223> OTHER INFORMATION: d-valine

<400> SEQUENCE: 15

Lys Lys Lys Lys Lys Lys Ser Ser Ile Ile Ser His Phe Arg Trp Gly
1               5                   10                  15

Lys Pro Val

<210> SEQ ID NO 16
<211> LENGTH: 19
<212> TYPE: PRT
<213> ORGANISM: Artificial sequence
<220> FEATURE:
<223> OTHER INFORMATION: alpha-MSH analogue
<220> FEATURE:
<221> NAME/KEY: MUTAGEN
<222> LOCATION: (19)..(19)
<223> OTHER INFORMATION: d-valine

<400> SEQUENCE: 16

Glu Glu Glu Glu Glu Glu Ser Ser Ile Ile Ser His Phe Arg Trp Gly
1               5                   10                  15

Lys Pro Val

<210> SEQ ID NO 17
<211> LENGTH: 19
<212> TYPE: PRT
<213> ORGANISM: Artificial sequence
<220> FEATURE:
<223> OTHER INFORMATION: alpha-MSH analogue
<220> FEATURE:
<221> NAME/KEY: MUTAGEN
<222> LOCATION: (13)..(13)
<223> OTHER INFORMATION: d-phenylalanine

<400> SEQUENCE: 17

Lys Lys Lys Lys Lys Lys Ser Ser Ile Ile Ser His Phe Arg Trp Gly
1               5                   10                  15

Lys Pro Val

<210> SEQ ID NO 18
<211> LENGTH: 19
<212> TYPE: PRT
<213> ORGANISM: Artificial sequence
<220> FEATURE:
<223> OTHER INFORMATION: alpha-MSH analogue
<220> FEATURE:
<221> NAME/KEY: MUTAGEN
<222> LOCATION: (13)..(13)
<223> OTHER INFORMATION: d-phenylalanine

<400> SEQUENCE: 18

Glu Glu Glu Glu Glu Glu Ser Ser Ile Ile Ser His Phe Arg Trp Gly
1               5                   10                  15

Lys Pro Val
```

```
<210> SEQ ID NO 19
<211> LENGTH: 19
<212> TYPE: PRT
<213> ORGANISM: Artificial sequence
<220> FEATURE:
<223> OTHER INFORMATION: alpha-MSH analogue
<220> FEATURE:
<221> NAME/KEY: MUTAGEN
<222> LOCATION: (13)..(13)
<223> OTHER INFORMATION: d-phenylalanine
<220> FEATURE:
<221> NAME/KEY: MUTAGEN
<222> LOCATION: (19)..(19)
<223> OTHER INFORMATION: d-valine

<400> SEQUENCE: 19

Lys Lys Lys Lys Lys Lys Ser Ser Ile Ile Ser His Phe Arg Trp Gly
1               5                   10                  15

Lys Pro Val

<210> SEQ ID NO 20
<211> LENGTH: 19
<212> TYPE: PRT
<213> ORGANISM: Artificial sequence
<220> FEATURE:
<223> OTHER INFORMATION: alpha-MSH analogue
<220> FEATURE:
<221> NAME/KEY: MUTAGEN
<222> LOCATION: (13)..(13)
<223> OTHER INFORMATION: d-phenylalanine
<220> FEATURE:
<221> NAME/KEY: MUTAGEN
<222> LOCATION: (19)..(19)
<223> OTHER INFORMATION: d-valine

<400> SEQUENCE: 20

Glu Glu Glu Glu Glu Glu Ser Ser Ile Ile Ser His Phe Arg Trp Gly
1               5                   10                  15

Lys Pro Val

<210> SEQ ID NO 21
<211> LENGTH: 19
<212> TYPE: PRT
<213> ORGANISM: Artificial sequence
<220> FEATURE:
<223> OTHER INFORMATION: alpha-MSH analogue
<220> FEATURE:
<221> NAME/KEY: MUTAGEN
<222> LOCATION: (13)..(13)
<223> OTHER INFORMATION: Xaa=beta-2-naphthyl-d-alanine

<400> SEQUENCE: 21

Lys Lys Lys Lys Lys Lys Ser Ser Ile Ile Ser His Xaa Arg Trp Gly
1               5                   10                  15

Lys Pro Val

<210> SEQ ID NO 22
<211> LENGTH: 19
<212> TYPE: PRT
<213> ORGANISM: Artificial sequence
<220> FEATURE:
<223> OTHER INFORMATION: alpha-MSH analogue
<220> FEATURE:
<221> NAME/KEY: MUTAGEN
<222> LOCATION: (13)..(13)
<223> OTHER INFORMATION: Xaa=beta-2-naphthyl-d-alanine

<400> SEQUENCE: 22
```

Glu Glu Glu Glu Glu Glu Ser Ser Ile Ile Ser His Xaa Arg Trp Gly
1               5                   10                  15

Lys Pro Val

<210> SEQ ID NO 23
<211> LENGTH: 19
<212> TYPE: PRT
<213> ORGANISM: Artificial sequence
<220> FEATURE:
<223> OTHER INFORMATION: alpha-MSH analogue
<220> FEATURE:
<221> NAME/KEY: MUTAGEN
<222> LOCATION: (13)..(13)
<223> OTHER INFORMATION: Xaa=beta-2-naphthyl-d-alanine
<220> FEATURE:
<221> NAME/KEY: MUTAGEN
<222> LOCATION: (19)..(19)
<223> OTHER INFORMATION: d-valine

<400> SEQUENCE: 23

Lys Lys Lys Lys Lys Lys Ser Ser Ile Ile Ser His Xaa Arg Trp Gly
1               5                   10                  15

Lys Pro Val

<210> SEQ ID NO 24
<211> LENGTH: 19
<212> TYPE: PRT
<213> ORGANISM: Artificial sequence
<220> FEATURE:
<223> OTHER INFORMATION: alpha-MSH analogue
<220> FEATURE:
<221> NAME/KEY: MUTAGEN
<222> LOCATION: (13)..(13)
<223> OTHER INFORMATION: Xaa=beta-2-naphthyl-d-alanine
<220> FEATURE:
<221> NAME/KEY: MUTAGEN
<222> LOCATION: (19)..(19)
<223> OTHER INFORMATION: d-valine

<400> SEQUENCE: 24

Glu Glu Glu Glu Glu Glu Ser Ser Ile Ile Ser His Xaa Arg Trp Gly
1               5                   10                  15

Lys Pro Val

<210> SEQ ID NO 25
<211> LENGTH: 16
<212> TYPE: PRT
<213> ORGANISM: Artificial sequence
<220> FEATURE:
<223> OTHER INFORMATION: alpha-MSH analogue

<400> SEQUENCE: 25

Lys Lys Lys Lys Lys Lys Met Glu His Phe Arg Trp Gly Lys Pro Val
1               5                   10                  15

<210> SEQ ID NO 26
<211> LENGTH: 16
<212> TYPE: PRT
<213> ORGANISM: Artificial sequence
<220> FEATURE:
<223> OTHER INFORMATION: alpha-MSH analogue

<400> SEQUENCE: 26

Glu Glu Glu Glu Glu Glu Met Glu His Phe Arg Trp Gly Lys Pro Val
1               5                   10                  15

<210> SEQ ID NO 27
<211> LENGTH: 16

```
<212> TYPE: PRT
<213> ORGANISM: Artificial sequence
<220> FEATURE:
<223> OTHER INFORMATION: alpha-MSH analogue
<220> FEATURE:
<221> NAME/KEY: MUTAGEN
<222> LOCATION: (16)..(16)
<223> OTHER INFORMATION: d-valine

<400> SEQUENCE: 27

Lys Lys Lys Lys Lys Lys Met Glu His Phe Arg Trp Gly Lys Pro Val
1               5                   10                  15

<210> SEQ ID NO 28
<211> LENGTH: 16
<212> TYPE: PRT
<213> ORGANISM: Artificial sequence
<220> FEATURE:
<223> OTHER INFORMATION: alpha-MSH analogue
<220> FEATURE:
<221> NAME/KEY: MUTAGEN
<222> LOCATION: (16)..(16)
<223> OTHER INFORMATION: d-valine

<400> SEQUENCE: 28

Glu Glu Glu Glu Glu Glu Met Glu His Phe Arg Trp Gly Lys Pro Val
1               5                   10                  15

<210> SEQ ID NO 29
<211> LENGTH: 16
<212> TYPE: PRT
<213> ORGANISM: Artificial sequence
<220> FEATURE:
<223> OTHER INFORMATION: alpha-MSH analogue
<220> FEATURE:
<221> NAME/KEY: MUTAGEN
<222> LOCATION: (7)..(7)
<223> OTHER INFORMATION: Xaa=Nle
<220> FEATURE:
<221> NAME/KEY: MUTAGEN
<222> LOCATION: (10)..(10)
<223> OTHER INFORMATION: d-phenylalanine

<400> SEQUENCE: 29

Lys Lys Lys Lys Lys Lys Xaa Glu His Phe Arg Trp Gly Lys Pro Val
1               5                   10                  15

<210> SEQ ID NO 30
<211> LENGTH: 16
<212> TYPE: PRT
<213> ORGANISM: Artificial sequence
<220> FEATURE:
<223> OTHER INFORMATION: alpha-MSH analogue
<220> FEATURE:
<221> NAME/KEY: MUTAGEN
<222> LOCATION: (7)..(7)
<223> OTHER INFORMATION: Xaa=Nle
<220> FEATURE:
<221> NAME/KEY: MUTAGEN
<222> LOCATION: (10)..(10)
<223> OTHER INFORMATION: d-phenylalanine

<400> SEQUENCE: 30

Glu Glu Glu Glu Glu Glu Xaa Glu His Phe Arg Trp Gly Lys Pro Val
1               5                   10                  15

<210> SEQ ID NO 31
<211> LENGTH: 16
<212> TYPE: PRT
<213> ORGANISM: Artificial sequence
<220> FEATURE:
<223> OTHER INFORMATION: alpha-MSH analogue
```

```
<220> FEATURE:
<221> NAME/KEY: MUTAGEN
<222> LOCATION: (7)..(7)
<223> OTHER INFORMATION: Xaa=Nle
<220> FEATURE:
<221> NAME/KEY: MUTAGEN
<222> LOCATION: (10)..(10)
<223> OTHER INFORMATION: d-phenylalanine
<220> FEATURE:
<221> NAME/KEY: MUTAGEN
<222> LOCATION: (16)..(16)
<223> OTHER INFORMATION: d-valine

<400> SEQUENCE: 31

Lys Lys Lys Lys Lys Lys Xaa Glu His Phe Arg Trp Gly Lys Pro Val
1               5                   10                  15

<210> SEQ ID NO 32
<211> LENGTH: 16
<212> TYPE: PRT
<213> ORGANISM: Artificial sequence
<220> FEATURE:
<223> OTHER INFORMATION: alpha-MSH analogue
<220> FEATURE:
<221> NAME/KEY: MUTAGEN
<222> LOCATION: (7)..(7)
<223> OTHER INFORMATION: Xaa=Nle
<220> FEATURE:
<221> NAME/KEY: MUTAGEN
<222> LOCATION: (10)..(10)
<223> OTHER INFORMATION: d-phenylalanine
<220> FEATURE:
<221> NAME/KEY: MUTAGEN
<222> LOCATION: (16)..(16)
<223> OTHER INFORMATION: d-valine

<400> SEQUENCE: 32

Glu Glu Glu Glu Glu Glu Xaa Glu His Phe Arg Trp Gly Lys Pro Val
1               5                   10                  15

<210> SEQ ID NO 33
<211> LENGTH: 16
<212> TYPE: PRT
<213> ORGANISM: Artificial sequence
<220> FEATURE:
<223> OTHER INFORMATION: alpha-MSH analogue
<220> FEATURE:
<221> NAME/KEY: MUTAGEN
<222> LOCATION: (7)..(7)
<223> OTHER INFORMATION: Xaa=Nle
<220> FEATURE:
<221> NAME/KEY: MUTAGEN
<222> LOCATION: (10)..(10)
<223> OTHER INFORMATION: Xaa=beta-2-naphthyl-d-alanine

<400> SEQUENCE: 33

Lys Lys Lys Lys Lys Lys Xaa Glu His Xaa Arg Trp Gly Lys Pro Val
1               5                   10                  15

<210> SEQ ID NO 34
<211> LENGTH: 16
<212> TYPE: PRT
<213> ORGANISM: Artificial sequence
<220> FEATURE:
<223> OTHER INFORMATION: alpha-MSH analogue
<220> FEATURE:
<221> NAME/KEY: MUTAGEN
<222> LOCATION: (7)..(7)
<223> OTHER INFORMATION: Xaa=Nle
<220> FEATURE:
<221> NAME/KEY: MUTAGEN
<222> LOCATION: (10)..(10)
<223> OTHER INFORMATION: Xaa=beta-2-naphthyl-d-alanine
```

-continued

```
<400> SEQUENCE: 34

Glu Glu Glu Glu Glu Glu Xaa Glu His Xaa Arg Trp Gly Lys Pro Val
1               5                   10                  15

<210> SEQ ID NO 35
<211> LENGTH: 16
<212> TYPE: PRT
<213> ORGANISM: Artificial sequence
<220> FEATURE:
<223> OTHER INFORMATION: alpha-MSH analogue
<220> FEATURE:
<221> NAME/KEY: MUTAGEN
<222> LOCATION: (7)..(7)
<223> OTHER INFORMATION: Xaa=Nle
<220> FEATURE:
<221> NAME/KEY: MUTAGEN
<222> LOCATION: (10)..(10)
<223> OTHER INFORMATION: Xaa=beta-2-naphthyl-d-alanine
<220> FEATURE:
<221> NAME/KEY: MUTAGEN
<222> LOCATION: (16)..(16)
<223> OTHER INFORMATION: d-valine

<400> SEQUENCE: 35

Lys Lys Lys Lys Lys Lys Xaa Glu His Xaa Arg Trp Gly Lys Pro Val
1               5                   10                  15

<210> SEQ ID NO 36
<211> LENGTH: 16
<212> TYPE: PRT
<213> ORGANISM: Artificial sequence
<220> FEATURE:
<223> OTHER INFORMATION: alpha-MSH analogue
<220> FEATURE:
<221> NAME/KEY: MUTAGEN
<222> LOCATION: (7)..(7)
<223> OTHER INFORMATION: Xaa=Nle
<220> FEATURE:
<221> NAME/KEY: MUTAGEN
<222> LOCATION: (10)..(10)
<223> OTHER INFORMATION: Xaa=beta-2-naphthyl-d-alanine
<220> FEATURE:
<221> NAME/KEY: MUTAGEN
<222> LOCATION: (16)..(16)
<223> OTHER INFORMATION: d-valine

<400> SEQUENCE: 36

Glu Glu Glu Glu Glu Glu Xaa Glu His Xaa Arg Trp Gly Lys Pro Val
1               5                   10                  15

<210> SEQ ID NO 37
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 37

Lys Lys Lys Lys Lys Lys
1               5

<210> SEQ ID NO 38
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 38

Glu Lys Lys Lys Lys Lys
1               5
```

```
<210> SEQ ID NO 39
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 39

Lys Glu Lys Lys Lys Lys
1               5

<210> SEQ ID NO 40
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 40

Lys Lys Glu Lys Lys Lys
1               5

<210> SEQ ID NO 41
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 41

Lys Lys Lys Glu Lys Lys
1               5

<210> SEQ ID NO 42
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 42

Lys Lys Lys Lys Glu Lys
1               5

<210> SEQ ID NO 43
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 43

Lys Lys Lys Lys Lys Glu
1               5

<210> SEQ ID NO 44
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 44

Glu Glu Lys Lys Lys Lys
1               5
```

```
<210> SEQ ID NO 45
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 45

Glu Lys Glu Lys Lys Lys
1               5

<210> SEQ ID NO 46
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 46

Glu Lys Lys Glu Lys Lys
1               5

<210> SEQ ID NO 47
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 47

Glu Lys Lys Lys Glu Lys
1               5

<210> SEQ ID NO 48
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 48

Glu Lys Lys Lys Lys Glu
1               5

<210> SEQ ID NO 49
<211> LENGTH: 6
<212> TYPE: ARtificial sequence
<213> ORGANISM: ARtificial sequence
<220> FEATURE:
<223> OTHER INFORMATION: alpha-MSH analogue

<400> SEQUENCE: 49

Lys Glu Glu Lys Lys Lys
1               5

<210> SEQ ID NO 50
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 50

Lys Glu Lys Glu Lys Lys
1               5

<210> SEQ ID NO 51
<211> LENGTH: 6
```

```
<212> TYPE: PRT
<213> ORGANISM: Artificial sequence
<220> FEATURE:
<223> OTHER INFORMATION: alpha-MSH analogue

<400> SEQUENCE: 51

Lys Glu Lys Lys Glu Lys
1               5

<210> SEQ ID NO 52
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 52

Lys Glu Lys Lys Lys Glu
1               5

<210> SEQ ID NO 53
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 53

Lys Lys Glu Glu Lys Lys
1               5

<210> SEQ ID NO 54
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 54

Lys Lys Glu Lys Glu Lys
1               5

<210> SEQ ID NO 55
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 55

Lys Lys Glu Lys Lys Glu
1               5

<210> SEQ ID NO 56
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 56

Lys Lys Lys Glu Glu Lys
1               5

<210> SEQ ID NO 57
<211> LENGTH: 6
<212> TYPE: PRT
<213> ORGANISM: Artificial sequence
```

```
<220> FEATURE:
<223> OTHER INFORMATION: alpha-MSH analogue

<400> SEQUENCE: 57

Lys Lys Lys Glu Lys Glu
1               5

<210> SEQ ID NO 58
<211> LENGTH: 6
<212> TYPE: PRT
<213> ORGANISM: Artificial seuence
<220> FEATURE:
<223> OTHER INFORMATION: alpha-MSH analogue

<400> SEQUENCE: 58

Lys Lys Lys Lys Glu Glu
1               5

<210> SEQ ID NO 59
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 59

Glu Glu Glu Lys Lys Lys
1               5

<210> SEQ ID NO 60
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 60

Glu Glu Lys Glu Lys Lys
1               5

<210> SEQ ID NO 61
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 61

Glu Glu Lys Lys Glu Lys
1               5

<210> SEQ ID NO 62
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 62

Glu Glu Lys Lys Lys Glu
1               5

<210> SEQ ID NO 63
<211> LENGTH: 6
<212> TYPE: PRT
<213> ORGANISM: Artificial sequence
<220> FEATURE:
<223> OTHER INFORMATION: alpha-MSH analogue
```

<400> SEQUENCE: 63

Glu Lys Glu Glu Lys Lys
1               5

<210> SEQ ID NO 64
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 64

Glu Lys Glu Lys Glu Lys
1               5

<210> SEQ ID NO 65
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 65

Glu Lys Glu Lys Lys Glu
1               5

<210> SEQ ID NO 66
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 66

Glu Lys Lys Glu Glu Lys
1               5

<210> SEQ ID NO 67
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 67

Glu Lys Lys Glu Lys Glu
1               5

<210> SEQ ID NO 68
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 68

Glu Lys Lys Lys Glu Glu
1               5

<210> SEQ ID NO 69
<211> LENGTH: 6
<212> TYPE: PRT
<213> ORGANISM: Artificial sequnence
<220> FEATURE:
<223> OTHER INFORMATION: alpha-MSH analogue

<400> SEQUENCE: 69

```
Lys Lys Lys Glu Glu Glu
1               5

<210> SEQ ID NO 70
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 70

Lys Lys Glu Lys Glu Glu
1               5

<210> SEQ ID NO 71
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 71

Lys Lys Glu Glu Lys Glu
1               5

<210> SEQ ID NO 72
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 72

Lys Lys Glu Glu Glu Lys
1               5

<210> SEQ ID NO 73
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 73

Lys Glu Lys Lys Glu Glu
1               5

<210> SEQ ID NO 74
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 74

Lys Glu Lys Glu Lys Glu
1               5

<210> SEQ ID NO 75
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 75

Lys Glu Lys Glu Glu Lys
```

<210> SEQ ID NO 76
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 76

Lys Glu Glu Lys Lys Glu
1               5

<210> SEQ ID NO 77
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 77

Lys Glu Glu Lys Glu Lys
1               5

<210> SEQ ID NO 78
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 78

Lys Glu Glu Glu Lys Lys
1               5

<210> SEQ ID NO 79
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 79

Lys Lys Glu Glu Glu Glu
1               5

<210> SEQ ID NO 80
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 80

Lys Glu Lys Glu Glu Glu
1               5

<210> SEQ ID NO 81
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 81

Lys Glu Glu Lys Glu Glu
1               5

-continued

```
<210> SEQ ID NO 82
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 82

Lys Glu Glu Glu Lys Glu
1               5

<210> SEQ ID NO 83
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 83

Lys Glu Glu Glu Glu Lys
1               5

<210> SEQ ID NO 84
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 84

Glu Lys Lys Glu Glu Glu
1               5

<210> SEQ ID NO 85
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 85

Glu Lys Glu Lys Glu Glu
1               5

<210> SEQ ID NO 86
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 86

Glu Lys Glu Glu Lys Glu
1               5

<210> SEQ ID NO 87
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 87

Glu Lys Glu Glu Glu Lys
1               5

<210> SEQ ID NO 88
```

```
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 88

Glu Glu Lys Lys Glu Glu
1               5

<210> SEQ ID NO 89
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 89

Glu Glu Lys Glu Lys Glu
1               5

<210> SEQ ID NO 90
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 90

Glu Glu Lys Glu Glu Lys
1               5

<210> SEQ ID NO 91
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 91

Glu Glu Glu Lys Lys Glu
1               5

<210> SEQ ID NO 92
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 92

Glu Glu Glu Lys Glu Lys
1               5

<210> SEQ ID NO 93
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 93

Glu Glu Glu Glu Lys Lys
1               5

<210> SEQ ID NO 94
<211> LENGTH: 6
<212> TYPE: PRT
```

```
<213> ORGANISM: Artificial sequence
<220> FEATURE:
<223> OTHER INFORMATION: alpha-MSH analogue

<400> SEQUENCE: 94

Lys Glu Glu Glu Glu Glu
1               5

<210> SEQ ID NO 95
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 95

Glu Lys Glu Glu Glu Glu
1               5

<210> SEQ ID NO 96
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 96

Glu Glu Lys Glu Glu Glu
1               5

<210> SEQ ID NO 97
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 97

Glu Glu Glu Lys Glu Glu
1               5

<210> SEQ ID NO 98
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 98

Glu Glu Glu Glu Lys Glu
1               5

<210> SEQ ID NO 99
<211> LENGTH: 6
<212> TYPE: PRT
<213> ORGANISM: Artificial sequence
<220> FEATURE:
<223> OTHER INFORMATION: alpha-MSH analogue

<400> SEQUENCE: 99

Glu Glu Glu Glu Glu Lys
1               5

<210> SEQ ID NO 100
<211> LENGTH: 6
<212> TYPE: PRT
<213> ORGANISM: Artificial sequence
<220> FEATURE:
```

-continued

```
<223> OTHER INFORMATION: alpha-MSH analogue

<400> SEQUENCE: 100

Glu Glu Glu Glu Glu Glu
1               5

<210> SEQ ID NO 101
<211> LENGTH: 13
<212> TYPE: PRT
<213> ORGANISM: Artificial sequence
<220> FEATURE:
<223> OTHER INFORMATION: alpha-MSH analogue

<400> SEQUENCE: 101

Ser Tyr Ser Met Glu His Phe Arg Trp Gly Lys Pro Val
1               5                   10
```

METHOD FOR PREVENTING OR REDUCING ACUTE RENAL FAILURE BY ADMINISTRATION OF THERAPEUTICALLY ACTIVE α-MSH ANALOGUES

This application is a continuation of U.S. patent application Ser. No. 12/064,923, filed Feb. 26, 2008, which is a national stage entry of PCT/DK2005/000545, filed Aug. 26, 2005, both of which are incorporated herein by reference in their entireties.

This application also incorporates by reference the Sequence Listing filed herewith and entitled "11653USC1SEQLIST", which was created on Feb. 25, 2013 and has a size of 25 KB.

FIELD OF INVENTION

The invention relates to peptide analogues of α-melanocyte-stimulating hormone (α-MSH), which posses an increased efficacy compared to the native α-MSH peptide. The α-MSH analogues exhibit increased anti-inflammatory effects and increased capability to treat or prevent whole body, organ or cell damages associated with ischemia or ischemia followed by vascular reperfusion compared to α-MSH.

BACKGROUND

The native peptide α-melanocyte-stimulating hormone (α-MSH) is known as the native agonist for the type 1, the type 3, the type 4 and the type 5 melanocortin (MC) receptor. The MC receptors belong to the class of G-protein coupled receptors. All receptor subtypes are coupled to a G-stimulatory protein, which means that receptor stimulation involves increased production of cAMP. ACTH is the native ligand to the Type 2 receptor (MC2).

A series of studies have been performed on the MC receptors in a variety of tissues. Type 1 receptor (MC1), to which α-MSH binds with great affinity, is known to be expressed in several tissues and cells such a brain, including astrocytes, testis, ovary, macrophages and neutrophils. MC1 is likely to be expressed, however, in an even wider range of tissues although this remains to be established. The selectivity for the MC receptors to bind different MSH peptides varies. MC1 binds with great affinity α-MSH and with lower affinity also β-MSH, γ-MSH and ACTH. MC2 has been reported only to bind ACTH, but none of the MSH peptides. The highest affinity for the ligands of the other receptors include γ-MSH (MC3-receptor), and β-MSH (MC4-receptor). In contrast, MC5 binds with much lower affinity the MSH peptides with the same pattern as MC1 (i.e. highest affinity for α-MSH).

MSH-peptides acting through stimulation of the MC-receptors have a variety of functions including immunomodulation, anti-inflammation, body temperature regulation, pain perception, aldosterone synthesis, blood pressure regulation, heart rate, vascular tone, brain blood flow, nerve growth, placental development, synthesis/release of a variety of hormones such as aldosterone, thyroxin, prolactin, FSH. ACTH has a major effect on stimulating steroidoneogenesis. Also α-MSH induces pigment formation in skin.

It is important to emphasize that a number of actions of MSH peptides, especially α-MSH, are not fully established with respect to which receptors are involved. The anti-inflammatory action of α-MSH has been speculated to involve a variety of processes including interference with NO production, endothelin-1 action, interleukin 10 formation, which again is linked to MC1 receptors expressed in macrophages and monocytes.

MC receptor stimulation with α-MSH has been shown to be important in a variety of inflammatory processes (Lipton and Catania 1997): 1) Inhibit chemotactive migration of neutrophils (Catania 1996). 2) α-MSH including analogs inhibit the release of cytokine (IL-1, TNF-α) in response to LPS treatment (Goninard 1996). 3) Inhibit TNF-α in response to bacterial endotoxin (Wong, K. Y. et al., 1997). 4) ICV or IP administration of α-MSH inhibit central TNF-α production by locally administered LPS. 5) α-MSH has been shown to reduce the inflammation in experimental inflammatory bowel disease (Rajora, N. et al., 1997), ischemia-induced acute renal failure (Star, R. A. et al., 1995). 6) α-MSH also have some protective effect by inhibiting the induction and elicitation of contact hypersensitivity and induces hapten tolerance, and it is speculated that α-MSH may mediate important negative regulation of cutaneous inflammation and hyper-proliferative skin diseases (Luger, T. A., 1997). To this end α-MSH causes increased IL-8 release from dermal microvasculature endothelial cells (Hartmeyer, M., 1997).

Both hypoxia (ischemia) and reperfusion injuries are important factors in human pathophysiology. Examples of tissue hypoxia that predispose to injury during reperfusion include circulatory shock, myocardial ischemia, stroke, temporary renal ischemia, major surgery and organ-transplantation. Because diseases due to ischemia are exceedingly common causes of morbidity and mortality and because organ transplantation is increasingly frequent, treatment strategies with the potential of limiting reperfusion injuries is of great need in order to improve public health. The underlying pathophysiology of ischemia reperfusion injuries is complex and involves not only a classical inflammatory reperfusion response with neutrophil-infiltration, but also cytokine gene expression including tumor necrosis factor-α (TNF-α), interleukin (IL)-1β, IL-6, IL-8, interferon-γ, and intercellular adhesion molecule-1 (ICAM-1) within the reperfusion tissue/organ. Furthermore, it has been suggested that locally produced TNF-α contributes to postischemic organ dysfunction as in the postinfarctional heart by direct depression of contractility and induction of apoptosis. Because of the complex nature of ischemia and/or reperfusion injuries simple anti-inflammatory treatment concepts have been shown ineffective: Most experimental studies therefore point to the fact that concomitant interaction with more than one of the activated pathways is needed in order to protect against reperfusion injuries. α-MSH have been shown to have both anti-inflammatory, anti-oxidative and anti-apoptotic abilities, which gives a good explanation for the effectiveness of this compound in order to protect against reperfusion injuries.

It is known that certain modifications of amino acid residues in the α-MSH amino acid sequence result in an increased receptor affinity (for e.g. the MC4 receptor), prolonged biological activity or a more receptor-specific binding profile of the peptide (Schiöth et al. 1998, Hruby et al. 1995, Sawyer et al. 1980, Hiltz et al. 1991, Scardenings et al. 2000). However, when aiming towards generation of peptidic drugs, these peptides still have problems with low stability towards enzymatic degradation.

As stated above, the problem in the development of peptidic therapeutical active drugs is that peptides are rapidly and very effectively degraded by enzymes, generally with half-lives in the range of minutes. Proteases and other proteolytic enzymes are ubiquitous, particularly in the gastro-intestinal tract, and therefore peptides are usually susceptible to degradation in multiple sites upon oral administration, and to some extent in the blood, the liver, the kidney, and the vascular endothelia. Furthermore, a given peptide is usually susceptible to degradation at more than one linkage within the backbone; each locus of hydrolysis is mediated by a certain protease. Even if such obstacles are overcome, for neuropeptides in particular, difficulties have been encountered in their transport across the blood-brain barrier.

In order to increase the metabolic stability of peptides, a technology called SIP (Structural Induced Probe) has been developed by Larsen et al. 1999 (WO 99/46283). The SIP technology is based on the use of structure inducing probes, which are represented by short peptide sequences, i.e. $(Lys)_6$ added to the C-terminal or to the N-terminal or both the C- and N-termini of the parent peptide. The structural inducing probe constrains the parent peptide into a more ordered conformation based on intramolecular hydrogen bonds, whereby the peptide chimer (peptide linked to the probe) is less susceptible to proteases in contrast to peptides in the random-coil conformation. As a result of the structuring, the peptide chimer is much more difficult for a protease to degrade. The addition of a SIP to a biologically active peptide generally results in an increase in the enzymatic stability of the peptide while the biological activity at the same time is maintained (Rizzi et al. 2002).

SUMMARY OF THE INVENTION

The present inventor has surprisingly shown that SIP-modification of α-MSH and α-MSH analogues in the N-terminal end of the peptides increases the maximal efficacy of the peptides compared to the native α-MSH peptide. The peptides of the invention display increased anti-inflammatory effects and increased capability to prevent ischemic conditions compared to the native α-MSH.

Thus, the present invention relates to specific peptides comprising a SIP modification in the N-terminal part of the peptide and an amino acid sequence of α-MSH or a variant of α-MSH in the C-terminal part of the peptide.

In a first aspect, the invention provides a peptide amounting in total from 12 to 19 amino acid residues comprising the amino acid sequence:

$$X\text{-}Aa_1\text{-}Aa_2\text{-}Aa_3\text{-}Aa_4\text{-}Aa_5\text{-}Y\text{-}Aa_6\text{-}Aa_7\text{-}Z$$

wherein X comprises six amino acid residues R1-R2-R3-R4-R5-R6, wherein R1, R2, R3, R4, R5 and R6 independently can be Lys or Glu, and wherein Y comprises an amino acid sequence selected from His-Phe-Arg, His-(D-Phe)-Arg, His-Nal-Arg and His-(D-Nal)-Arg, and wherein Z comprises an amino acid sequence selected from Lys-Pro-Val and Lys-Pro-(D-Val), and wherein $Aa_1$, $Aa_2$, $Aa_3$, $Aa_4$, $Aa_5$, $Aa_6$ and $Aa_7$ independently can be any natural or unnatural amino acid residue or absent, and wherein the carboxy terminus of said peptide is —C(=O)—B1, wherein B1 is selected from OH, $NH_2$, NHB2, N(B2)(B3), OB2, and B2, wherein B2 and B3 are independently selected from optionally substituted $C_{1-6}$ alkyl, optionally substituted $C_{2-6}$ alkenyl, optionally substituted $C_{6-10}$ aryl, optionally substituted $C_{7-16}$ aralkyl, and optionally substituted $C_{7-16}$ alkylaryl; and wherein the amino terminus of said peptide is (B4)HN—, (B4)(B5)N—, or (B6)HN—, wherein B4 and B5 are independently selected from H, optionally substituted $C_{1-6}$ alkyl, optionally substituted $C_{2-6}$ alkenyl, optionally substituted $C_{6-10}$ aryl, optionally substituted $C_{7-16}$ aralkyl, and optionally substituted $C_{7-16}$ alkylaryl; B6 is B4-C(=O)—.

The invention also relates to use of said peptides for the manufacture of pharmaceutical compositions for the treatment or prophylaxis of a condition in the tissue of one or more organs of a mammal. Furthermore, the present invention relates to a composition, e.g., a pharmaceutical composition, comprising one or more peptides according to the invention and a pharmaceutically acceptable carrier, to peptides according to the invention for use in medicine, and to methods for treating a condition in the tissue of one or more organs of a mammal comprising administering an effective dose of a peptide according to the invention. Specifically, the invention is directed to a method for treating conditions caused by ischemia, inflammation and/or toxic effects of poising or drug treatment.

The figure shows the maximal antiinflammatory effect of α-MSH analogue #1 (SEQ ID NO.1*) (MCA#1) in experimental setup 1. The maximal inhibitory effect on LPS-induced TNF-α production was achieved by $10^{-7}$ M for both α-MSH and MCA#1. Mean±SE (N=6-9 in each group). *:p<0.05 vs Vehicle#:p<0.05 vs α-MSH.

Figure 2:
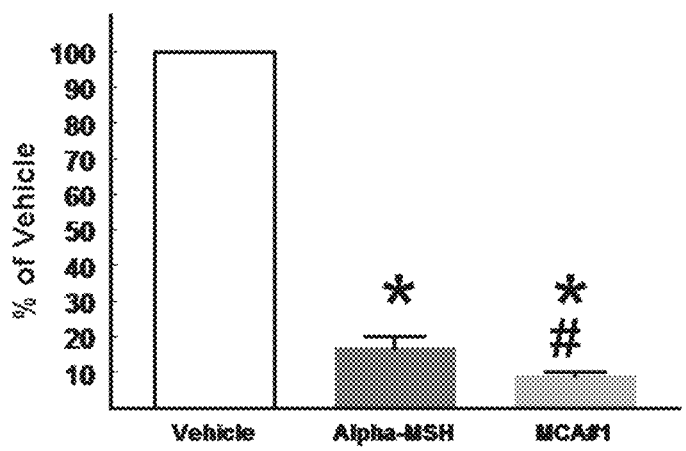

FIG. 2 LPS Induced TNF-α Accumulation on Plasma

The figure shows the maximal antiinflammatory effect of α-MSH analogue #1 (SEQ ID NO.1*) (MCA#1) in experimental setup 2. The maximal inhibitory effect on LPS-induced TNF-α production in rats was achieved by 200 µg/kg bw given iv for both α-MSH and MCA#1. Mean±SE (N=4-6 in each group). *:p<0.05 vs Vehicle#:p<0.05 vs α-MSH.

FIG. 3 Eosinophils

The figure shows the effect of αMSH and α-MSH analogue #1 (SEQ ID NO.1*) (MCA#1) on eosinophil accumulation within the lungs in experimental setup 3. Both compounds were given in a dose of 200 µg/kg bw given iv bid. Mean±SE (N=6-9 in each group). *:different from vehicle.

Figure 4:
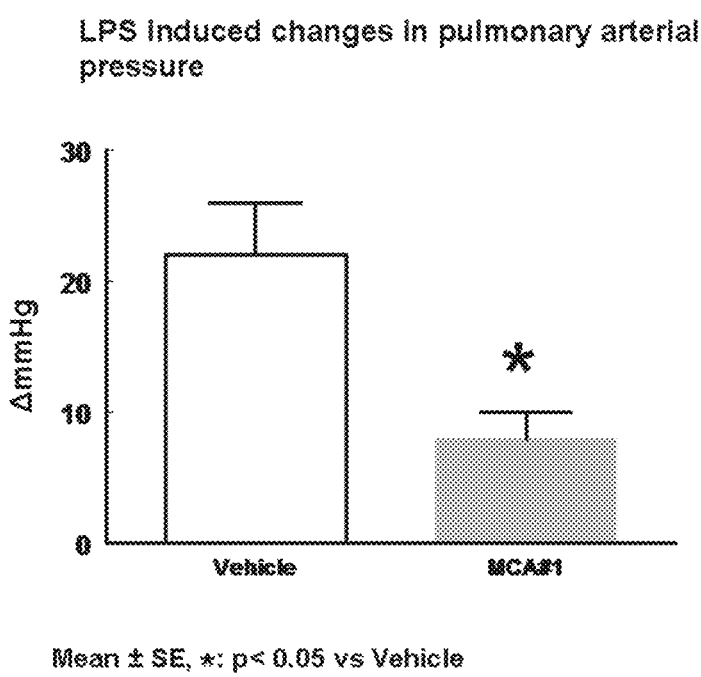

FIG. 4 Pulmonary Artery Pressure

The figure shows effect of α-MSH analogue #1 (SEQ ID NO.1*) (MCA#1) on LPS induced the changes in pulmonary artery pressure in pigs. Mean±SE (N=3 and 6 in the two groups). *:different from vehicle.

Figure 5:
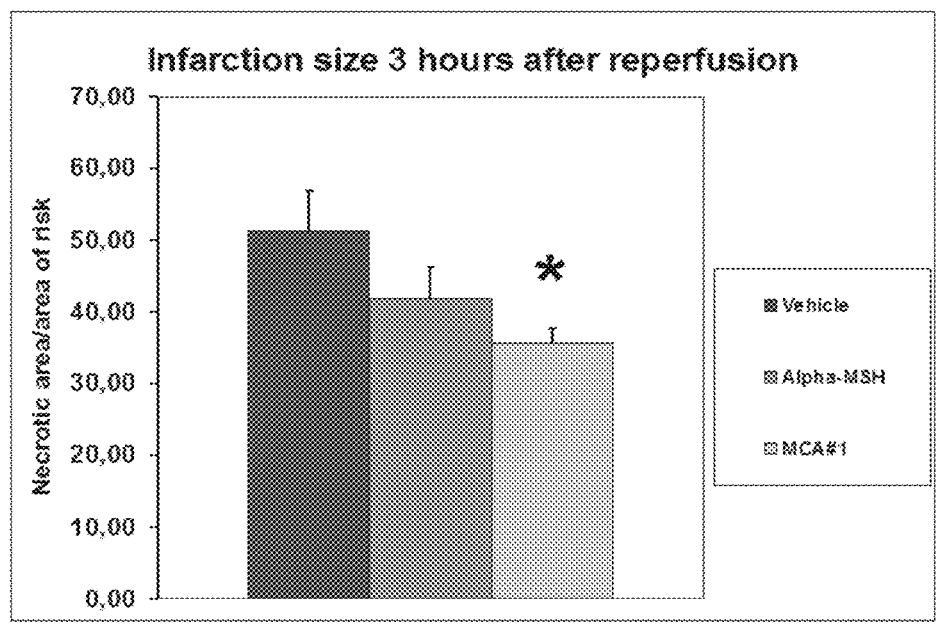

FIG. 5 Infarction Size 3 Hours after Reperfusion

The figure shows the protective effect of α-MSH analogue #1 (SEQ ID NO.1*) (MCA#1) on myocardial infarction size in experimental setup 4. The maximal effect of MCA#1 was achieved by 200 µg/kg bw given iv. Mean±SE (N=5-10 in each group). *:different from vehicle.

Figure 6:
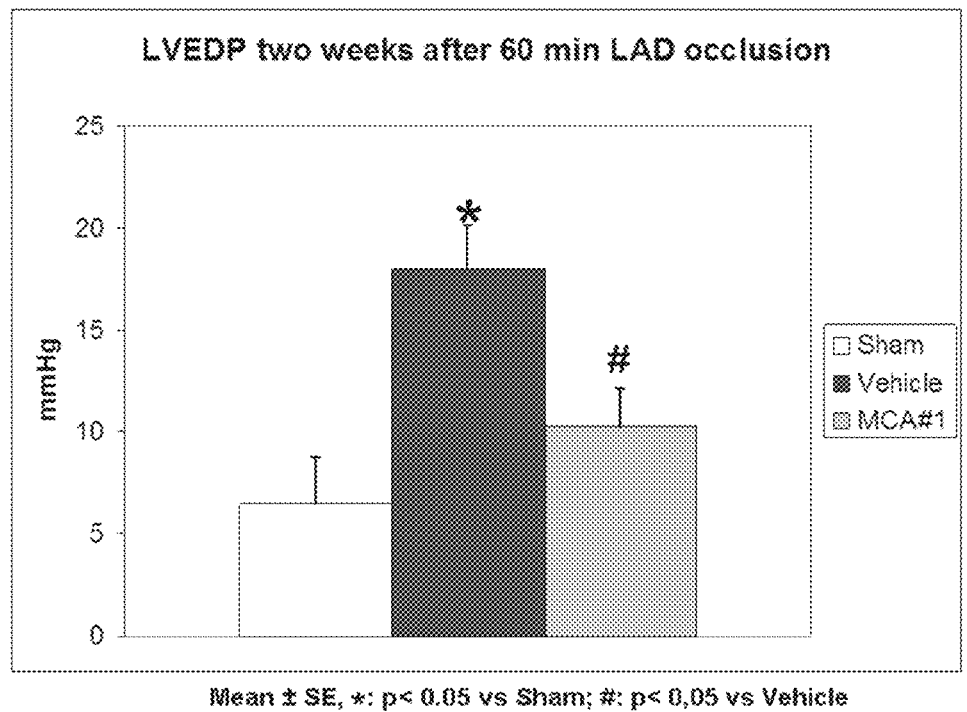

FIG. 6 LVEDP Two Weeks after 60 Min LAD Occlusion

The figure shows the protective effect of α-MSH analogue #1 (SEQ ID NO.1*) (MCA#1) on the development of post infarctional congestive heart failure in experimental setup 5. The effect of MCA#1 was achieved by 200 µ/kg bw. Mean±SE (N=6-9 in each group). *:p<0.05 vs Sham; #:p<05 vs vehicle.

FIG. 7 Diuresis

The figure shows the protective effect of α-MSH analogue #1 (SEQ ID NO.1*) (MCA#1) on the development of post ischemic polyuria in experimental setup 6. The effect of MCA#1 was achieved by 200 µg/kg bw given iv. Mean±SE (N=5-7 in each group). *;different from vehicle.

Figure 8:
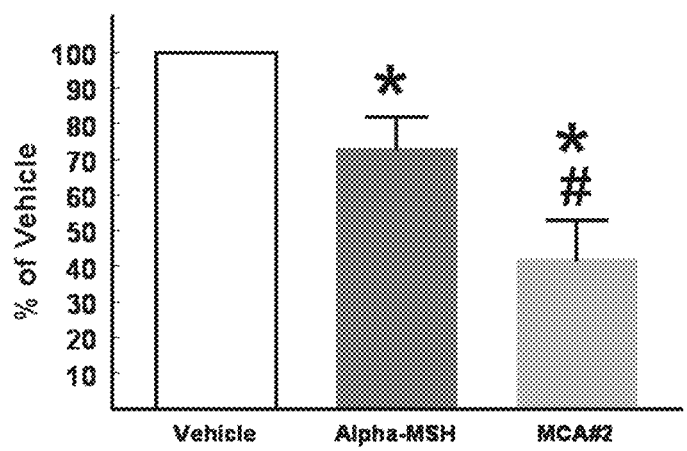

FIG. 8 LPS Induced TNF-α Accumulation in Suspension of Human Lymphocytes

The figure shows the maximal antiinflammatory effect of the α-MSH analogue #2 (SEQ. NO. 5) (MCA#2) in experimental setup 1. The maximal inhibitory effect on LPS-induced TNFα production was achieved by $10^{-7}$ M for both α-MSH and MCA#2. Mean±SE (N=6-9 in each group). *:p<0.05 vs Vehicle; #:p<0.05 vs α-MSH.

Figure 9:
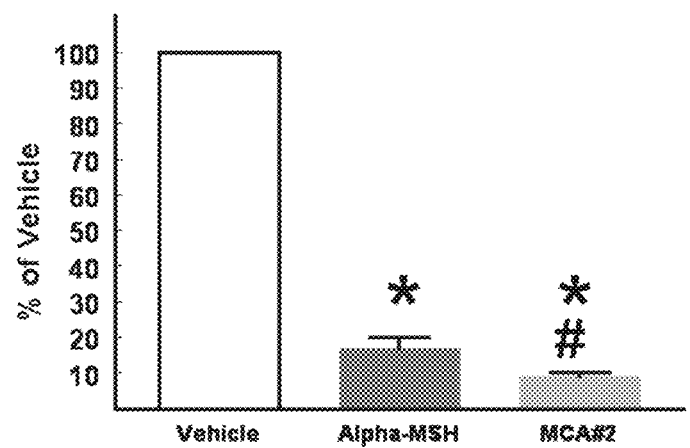

FIG. 9 LPS Induced TNF-α Accumulation in Plasma

The figure shows the maximal antiinflammatory effect of α-MSH analogue α-MSH analogue #2 (SEQ. NO. 5) (MCA#2) in experimental setup 2. The maximal inhibitory effect on LPS-induced TNF-α production in rats was achieved by 200 μg/kg bw given iv for both α-MSH and MCA#2. Mean±SE (N=4-6 in each group). *:p<0.05 vs Vehicle; #:p<0.05 vs α-MSH.

Figure 10:
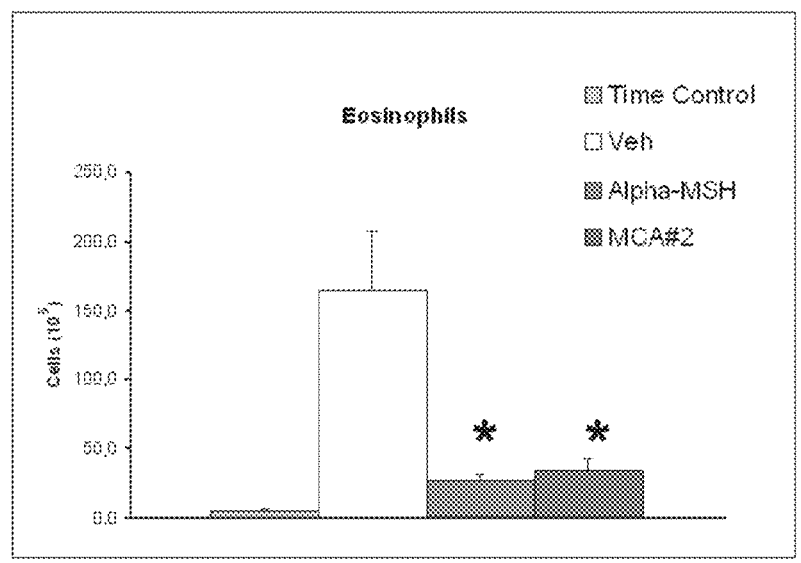

FIG. 10 Eosinophils

The figure shows the effect of α-MSH and α-MSH analogue #2 (SEQ ID NO.5*) (MCA#2) on eosinophil accumulation within the lungs in experimental setup 3. Both compounds were given in a dose of 200 μg/kg bw given iv bid. Mean±SE (N=6-9 in each group). *:different from vehicle.

Figure 11:
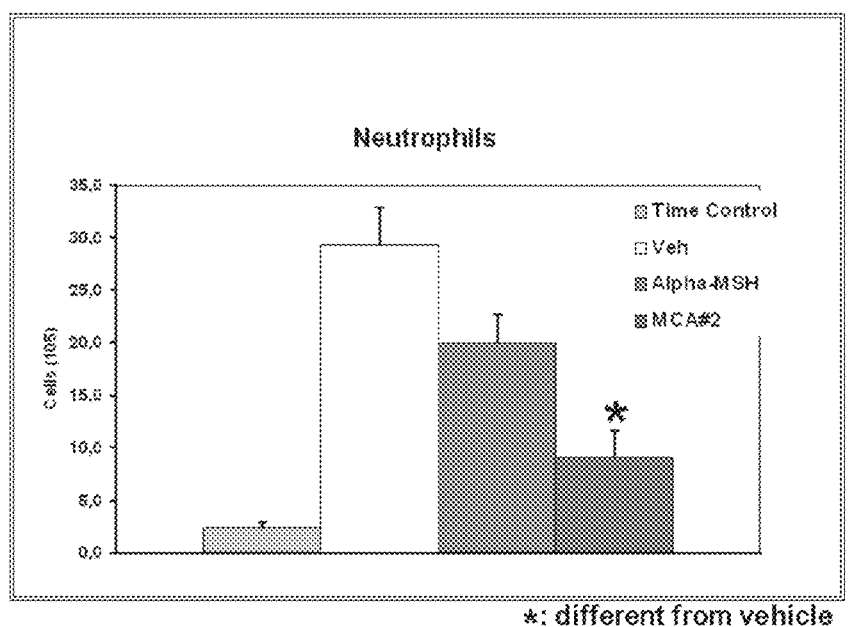

FIG. 11 Neutrophils

The figure shows the effect of α-MSH and α-MSH analogue #2 (SEQ ID NO.5*) (MCA#2) on neutrophil accumulation within the lungs in experimental setup 3. Both compounds were given in a dose of 200 μg/kg bw given iv bid. Mean±SE (N=6-9 in each group). *:different from vehicle.

Figure 12:
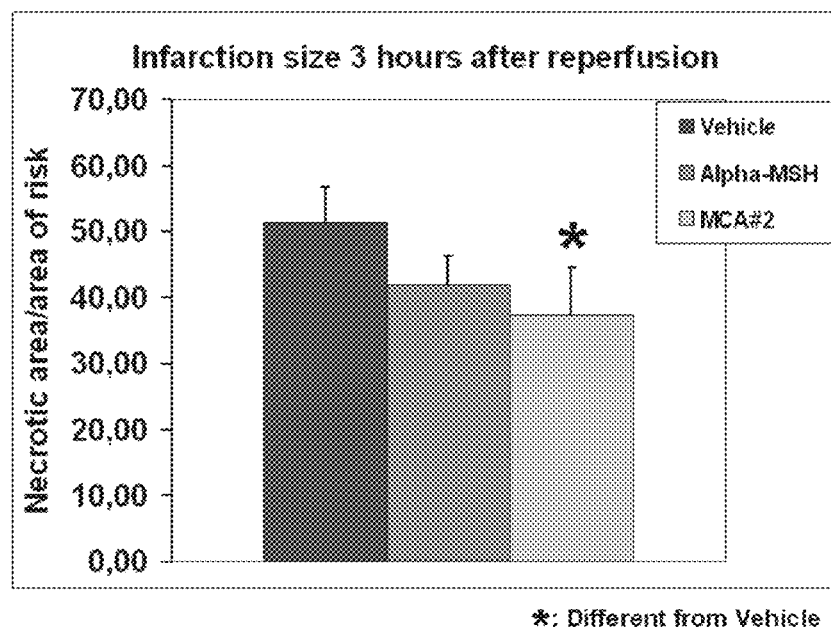

FIG. 12 Infarction Size 3 Hours after Reperfusion

The figure shows the protective effect of α-MSH analogue #2 (SEQ ID NO.5*) (MCA#2) on myocardial infarction size in experimental setup 4. The effect of MCA#3 was achieved by μg/kg bw given iv. Mean±SE (N=5-10 in each group). *:different from vehicle.

Figure 13:
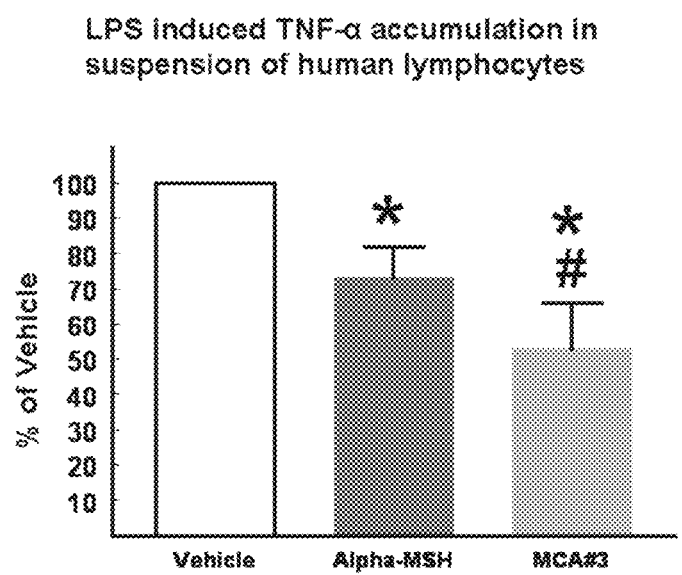

FIG. 13 LPS Induced TNF-α Accumulation in Suspension of Huuman Lymphocytes

The figure shows the maximal antiinflammatory effect of α-MSH analogue #3 (SEQ ID NO.9*) (MCA#3) in experimental setup 1. The maximal inhibitory effect on LPS-induced TNFα production was achieved by $10^{-7}$ M for both α-MSH and MCA#3. Mean±SE (N=6-9 in each group). *:p<0.05 vs Vehicle; #:p<0.05 vs α-MSH.

Figure 14:
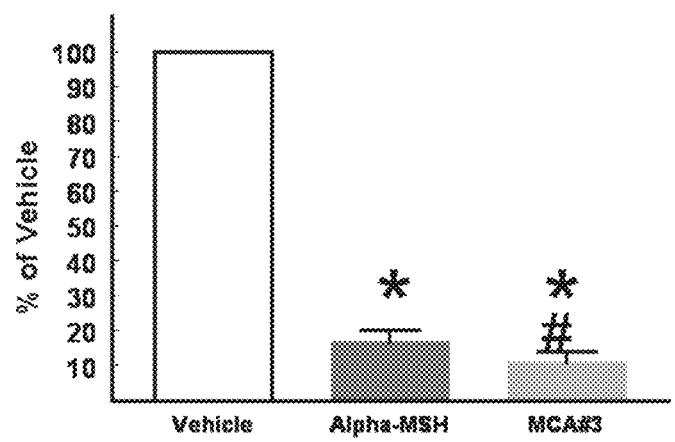

FIG. 14 LPS Induced TNF-α Accumulation in Plasma

The figure shows the maximal antiinflammatory effect of α-MSH analogue #3 (SEQ. NO. 9) (MCA#3) in experimental setup 2. The maximal inhibitory effect on LPS-induced TNFα production in rats was achieved by 200 μg/kg bw given iv for both α-MSH and MCA#3. Mean±SE (N=4-6 in each group). *:p<0.05 vs Vehicle; #:p<0.05 vs α-MSH.

Figure 15:
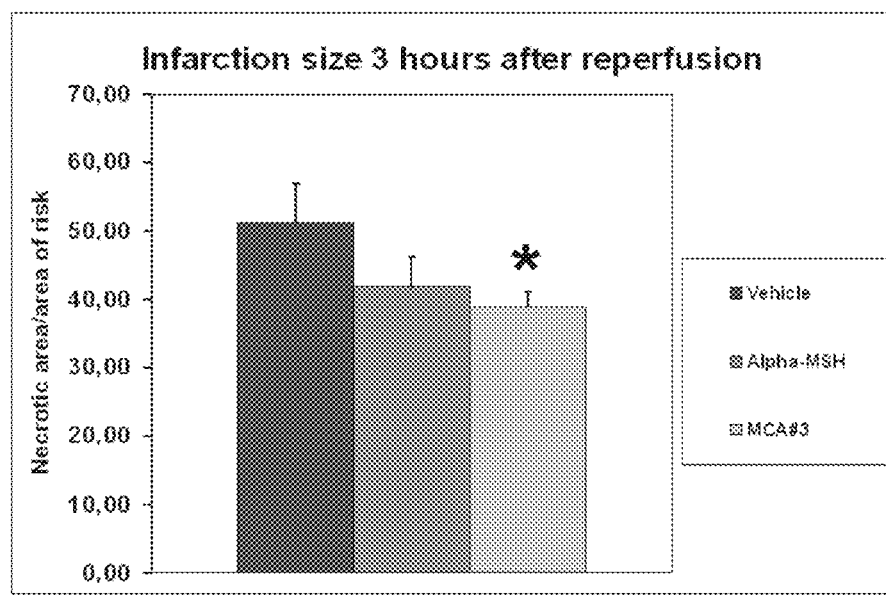

FIG. 15 Infarction Size 3 Hours after Reperfusion

The figure shows the protective effect of α-MSH analogue #3 (SEQ ID NO.9*) (MCA#3) on myocardial infarction size in experimental setup 4. The effect of MCA#3 was achieved by μg/kg bw given iv. Mean±SE (N=5-10 in each group). *:different from vehicle.

Figure 16:
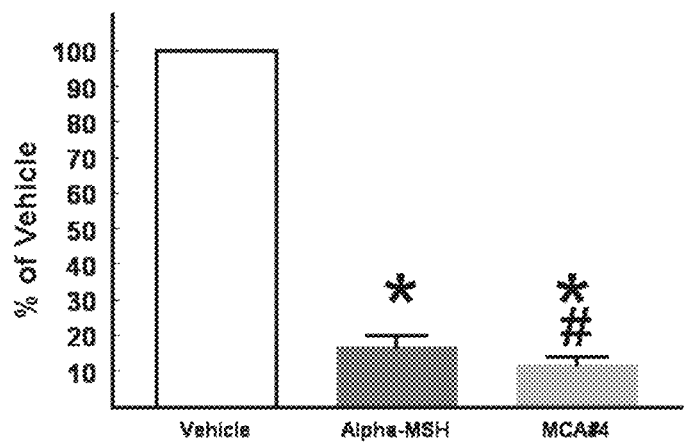

FIG. 16 LPS Induced TNF-α Accumulation in Plasma

The figure shows the maximal antiinflammatory effect of α-MSH analogue #4 (SEQ. NO. 13) (MCA#4) in experimental setup 2. The maximal inhibitory effect on LPS-induced TNFα production in rats was achieved by 200 μg/kg bw given iv for both α-MSH and MCA#4. Mean±SE (N=4-6 in each group). *:p<0.05 vs Vehicle; #:p<0.05 vs α-MSH.

DESCRIPTION OF THE INVENTION

The present invention relates to therapeutically active peptides having the effects of ameliorate or prevent organ dysfunction induced by ischemia, inflammation and/or toxic effects of poising or drug treatment.

As defined herein, a peptide sequence is "therapeutically active" if it can be used for the treatment, remission, or attenuation of a disease state, physiological condition, symptoms or etiological indication(s) or evaluation or diagnosis thereof. A peptide sequence is "prophylactically active" if it can be used to prevent a disease state, physiological condition, symptoms or etiological indications. A pharmacologically active agent is also physiologically and/or biologically active. Pharmacological activity measures the effect of a substance (peptide) on physiological and/or biological systems in vitro, in vivo or ex vivo and may be assayed using standard in vitro, in vivo or ex vivo assays known in the art for a particular peptide or a peptide with a similar physiological function The Peptides of the Invention The present invention relates to peptides comprising the amino acid sequence of α-MSH or a variant of α-MSH in the C-terminal part of the peptide and a structural inducing probe (SIP) in the N-terminal part of the peptide. The peptides of the invention are termed α-MSH analogues. In the present specification and claims, these terms are used synonymously.

The α-MSH variant is defined as an amino acid sequence that is modified compared to naturally occurring α-MSH (Ser-Tyr-Ser-Met-Glu-His-Phe-Arg-Trp-Gly-Lys-Pro-Val, SEQ ID NO: 101) by having at least one amino acid residue deletion, substitution, addition or modification within the sequence. The α-MSH variant preferably has the structure: $Aa_1$-$Aa_2$-$Aa_3$-$Aa_4$-$Aa_5$-Y-$Aa_6$-$Aa_7$-Z, wherein Y comprises an amino acid sequence selected from His-Phe-Arg, His-(D-Phe)-Arg, His-Nal-Arg and His-(D-Nal)-Arg, and wherein Z comprises an amino acid sequence selected from Lys-Pro-Val and Lys-Pro-(D-Val), and wherein $Aa_1$, $Aa_2$, $Aa_3$, $Aa_4$, $Aa_5$, $Aa_6$ and $Aa_7$ independently can be any natural or unnatural amino acid residue or absent.

In the present context, the term "amino acid residue" means any naturally occurring amino acid residue (natural amino acid residue) or unnaturally occurring amino acid residue (unnatural amino acid residue).

A natural amino acid residue is defined as an amino acid residue existing in nature, such as Ala, Arg, Asn, Asp, Cys, Gln, Glu, Gly, H is, Ile, Leu, Lys, Met, Phe, Pro, Ser, Tyr, Thr, Trp, Val.

Examples of preferred natural amino acid residues with regard to the α-MSH variant structure, are Ser, Tyr, Met, Glu, Ile, Trp and Gly.

An unnaturally amino acid residue is defined as an amino acid residue not existing in nature, but created experimentially. The unnatural amino acid residues include synthetic α, β, or γ-amino acid residues (whether in the L-configuration or the D-configuration) as well as side-chain modified amino acids such as modified tyrosines wherein the aromatic ring is further substituted with e.g., one or more halogens, sulfono groups, nitro groups etc., and/or the phenol group is converted into an ester group, etc, including side-chain protected amino acids, wherein the amino acid side-chains are protected in accordance with methods known to the person skilled in peptide chemistry, such as described in, e.g., Bodanszky et al. 1994, and J. Jones, and Jones 1991. Examples of preferred unnatural amino acid residues are Norleucine (Nle), Nal (beta-2-naphthyl-alanine), D-Nal (beta-2-naphthyl-d-alanine), D-phenylalanine (D-Phe) and D-valine (D-Val).

In the broadest aspect, the present invention relates to a peptide amounting in total from to 19 amino acid residues comprising the amino acid sequence:

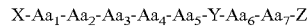

wherein X comprises six amino acid residues R1-R2-R3-R4-R5-R6, wherein R1, R2, R3, R4, R5 and R6 independently can be Lys or Glu, and wherein Y comprises an amino acid sequence selected from His-Phe-Arg, His-(D-Phe)-Arg, His-Nal-Arg and His-(D-Nal)-Arg, and wherein Z comprises an amino acid sequence selected from Lys-Pro-Val and Lys-Pro-(D-Val), and wherein $Aa_1$, $Aa_2$, $Aa_3$, $Aa_4$, $Aa_5$, $Aa_6$ and $Aa_7$ independently can be any natural or unnatural amino acid residue or absent, and wherein the carboxy terminus of said peptide is —C(=O)—B1, wherein B1 is selected from OH, $NH_2$, NHB2, N(B2)(B3), OB2, and B2, wherein B2 and B3 are independently selected from optionally substituted $C_{1-6}$ alkyl, optionally substituted $C_{2-6}$ alkenyl, optionally substituted $C_{6-10}$ aryl, optionally substituted $C_{7-16}$ aralkyl, and optionally substituted $C_{7-16}$ alkylaryl; and wherein the amino terminus of said peptide is (B4)HN—, (B4)(B5)N—, or (B6)HN—, wherein B4 and B5 are independently selected from H, optionally substituted $C_{1-6}$ alkyl, optionally substituted $C_{2-6}$ alkenyl, optionally substituted $C_{6-10}$ aryl, optionally substituted $C_{7-16}$ aralkyl, and optionally substituted $C_{7-16}$ alkylaryl; B6 is B4-C(=O)—.

In the context of the present invention, the term "optionally substituted" is intended to mean that the group in question may be substituted one or several times, such as 1 to 5 times, preferably 1 to 3 times, most preferably one to two times, with one or more groups selected from $C_{1-8}$-alkyl, $C_{1-8}$-alkoxy, oxo (which may be represented in the tautomeric enol form), carboxyl, amino, hydroxy (which when present in an enol system may be represented in the tautomeric keto form), nitro, cyano, dihalogen-$C_{1-8}$-alkyl, trihalogen-$C_{1-8}$-alkyl, halogen. In general, the above substituents may be susceptible to further optional substitution.

In the present context, the term "$C_{1-6}$-alkyl" is intended to mean a linear or branched saturated hydrocarbon chain wherein the longest chains has from one to six carbon atoms, such as methyl, ethyl, n-propyl, isopropyl, n-butyl, isobutyl, sec-butyl, tert-butyl, pentyl, isopentyl, neopentyl, hexyl, heptyl and octyl. A branched hydrocarbon chain is intended to mean a $C_{1-6}$-alkyl substituted at any carbon with a hydrocarbon chain.

In the present context, the term "$C_{2-6}$-alkenyl" is intended to mean a linear or branched hydrocarbon group having from two to six carbon atoms and containing one or more double bonds. Illustrative examples of $C_{2-6}$-alkenyl groups include allyl, homo-allyl, vinyl, crotyl, butenyl, pentenyl, and hexenyl. Illustrative examples of $C_{2-6}$-alkenyl groups with more than one double bond include butadienyl, pentadienyl, hexadienyl, and hexatrienyl groups as well as branched forms of these. The position of the unsaturation (the double bond) may be at any position along the carbon chain.

In the present context the term "$C_{3-8}$-cycloalkyl" is intended to cover three-, four-, five-, six- seven-, and eight-membered rings comprising carbon atoms only whereas the term "heterocyclyl" is intended to mean three-, four-, five-, six- seven-, and eight-membered rings wherein carbon atoms together with from 1 to 3 heteroatoms constitute said ring. The heteroatoms are independently selected from oxygen, sulphur, and nitrogen.

$C_{3-8}$-cycloalkyl and heterocyclyl rings may optionally contain one or more unsaturated bonds situated in such a way, however, that an aromatic π-electron system does not arise.

Illustrative examples of preferred "$C_{3-8}$-cycloalkyl" are the carbocycles cyclopropane, cyclobutane, cyclopentane, cyclopentadiene, cyclohexane, cyclohexene, 1,3-cyclohexadiene, 1,4-cyclohexadiene, cycloheptane, cycloheptene, 1,2-cycloheptadiene, 1,3-cycloheptadiene, 1,4-cycloheptadiene and 1,3,5 cycloheptatriene.

Illustrative examples of "heterocyclyls" are the heterocycles 2H-thipyran, 3H-thipyran, 4H-thipyran, tetrahydrothiopyran, 2H-pyran, 4H-pyran, tetrahydropyran, piperidine, 1,2-dithiin, 1,2-dithiane, 1,3-dithiin, 1,3-dithiane, 1,4-dithiin, 1,4-dithiane, 1,2-dioxin, 1,2-dioxane, 1,3-dioxin, 1,3-dioxane, 1,4-dioxin, 1,4-dioxane, piperazine, 1,2-oxathiin, 1,2-oxathiane, 4H-1,3-oxathiin, 1,3-oxathiane, 1,4-oxathiin, 1,4-oxathiane, 2H-1,2-thiazine, tetrahydro-1,2-thiazine, 2H-1,3-thiazine, 4H-1,3-thiazine, 5,6-dihydro-4H-thiazine, 4H-1,4-thiazine, tetrahydro-1,4-thiazine, 2H-1,2-oxazine, 4H-1,2-oxazine, 6H-1,2-oxazine, 2H1,3-oxazine, 4H-1,3-oxazine, 4H-1,4-oxazine, maleimide, succinimide, imidazole, pyrazole, pyrrole, oxazole, furazan, barbituric acid, thiobarbituric acid, dioxopiperazine, isoxazole, hydantoin, dihydrouracil, morpholine, trioxane, 4H-1,2,3-trithiin, 1,2,3-trithiane, 1,3,5-trithiane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,2-dioxole, 1,2-dioxolane, 1,3-dioxole, 1,3-dioxolane, 3H-1,2-dithiole, 1,2-dithiolane, 1,3-dithiole, 1,3-dithiolane, isoxazoline, isoxazolidine, oxazoline, oxazolidine, thiazoline, thiozolidine, 3H-1,2-oxathiole, 1,2-oxathiolane, 5H-1,2-oxathiole, 1,3-oxathiole, 1,3-oxathiolane, 1,2,3-trithiole, 1,2,3-trithiolane, 1,2,4-trithiolane, 1,2,3-trioxole, 1,2,3-trioxolane, 1,2,4-trioxolane, 1,2,3-triazoline and 1,2,3-triazolidine. Binding to the heterocycle may be at the position of the heteroatom or via carbon atom of the heterocycle.

In the present context the term "aryl" is intended to mean a carbocyclic aromatic ring or ring system. Moreover, the term "aryl" includes fused ring systems wherein at least two aryl rings, or at least one aryl and at least one $C_{3-8}$-cycloalkyl, or at least one aryl and at least one heterocyclyl, share at least chemical bond. Illustrative examples of "aryl" rings include optionally substituted phenyl, naphthalenyl, phenanthrenyl, anthracenyl, acenaphthylenyl, tetralinyl, fluorenyl, indenyl, indolyl, coumaranyl, coumarinyl, chromanyl, isochromanyl, and azulenyl. A preferred aryl group is phenyl.

In the present context "C7-16 aralkyl" is intended to mean a C6-10 aryl substituted with C1-6 alkyl.

In the present context "C7-16 alkylaryl" is intended to mean a C1-6 alkyl substituted with C6-10 aryl.

In one embodiment, the invention relates to a peptide amounting in total from 12 to 19 amino acid residues comprising an amino acid sequence selected from the group consisting of

X-Y-Z,

X-$Aa_1$-Y-Z,

X-$Aa_1$-$Aa_2$-Y-Z,

X-$Aa_1$-$Aa_2$-$Aa_3$-Y-Z,

X-$Aa_1$-$Aa_2$-$Aa_3$-$Aa_4$-Y-Z,

X-$Aa_1$-$Aa_2$-$Aa_3$-$Aa_4$-$Aa_5$-Y-Z,

X-$Aa_1$-Y-$Aa_6$-Z,

X-$Aa_1$-$Aa_2$-Y-$Aa_6$-Z,

X-$Aa_1$-$Aa_2$-$Aa_3$-Y-$Aa_6$-Z,

X-$Aa_1$-$Aa_2$-$Aa_3$-$Aa_4$-Y-$Aa_6$-Z,

X-$Aa_1$-$Aa_2$-$Aa_3$-$Aa_4$-$Aa_5$-Y-$Aa_6$-Z,

X-$Aa_1$-Y-$Aa_6$-$Aa_7$-Z,

X-Aa$_1$-Aa$_2$-Y-Aa$_6$-Aa$_7$-Z,

X-Aa$_1$-Aa$_2$-Aa$_3$-Y-Aa$_6$-Aa$_7$-Z,

X-Aa$_1$-Aa$_2$-Aa$_3$-Aa$_4$-Y-Aa$_6$-Aa$_7$-Z, and

X-Aa$_1$-Aa$_2$-Aa$_3$-Aa$_4$-Aa$_5$-Y-Aa$_6$-Aa$_7$-Z wherein X comprises six amino acid residues R1-R2-R3-R4-R5-R6, wherein R1, R2, R3, R4, R5 and R6 independently can be Lys or Glu, and wherein Y comprises an amino acid sequence selected from His-Phe-Arg, His-(D-Phe)-Arg, His-Nal-Arg and His-(D-Nal)-Arg, and wherein Z comprises an amino acid sequence selected from Lys-Pro-Val and Lys-Pro-(D-Val), and wherein Aa$_1$, Aa$_2$, Aa$_3$, Aa$_4$, Aa$_5$, Aa$_6$ and Aa$_7$ independently can be any natural or unnatural amino acid residue or absent, and wherein the carboxy terminus of said peptide is —C(=O)—B1, wherein B1 is selected from OH, NH$_2$, NHB2, N(B2)(B3), OB2, and B2, wherein B2 and B3 are independently selected from optionally substituted C$_{1-6}$ alkyl, optionally substituted C$_{2-6}$ alkenyl, optionally substituted C$_{6-10}$ aryl, optionally substituted C$_{7-16}$ aralkyl, and optionally substituted C$_{7-16}$ alkylaryl; and wherein the amino terminus of said peptide is (B4)HN—, (B4)(B5)N—, or (B6)HN—, wherein B4 and 65 are independently selected from H, optionally substituted C$_{1-6}$ alkyl, optionally substituted C$_{2-6}$ alkenyl, optionally substituted C$_{6-10}$ aryl, optionally substituted C$_{7-16}$ aralkyl, and optionally substituted C$_{7-16}$ alkylaryl; B6 is B4-C(=O)—.

In a preferred embodiment, the invention relates to a peptide, wherein the peptide comprises the amino acid sequence:

X-Aa$_1$-Aa$_2$-Aa$_3$-Aa$_4$-Aa$_5$-Y-Aa$_6$-Aa$_7$-Z.

wherein Aa$_1$, Aa$_2$, Aa$_3$, Aa$_4$, Aa$_5$, Aa$_6$ and Aa$_7$ independently can be any natural or unnatural amino acid. Thus, Aa$_1$, Aa$_2$, Aa$_3$, Aa$_4$, Aa$_5$, Aa$_6$ and Aa$_7$ are all present in the peptide of the invention.

In one embodiment, the invention relates to peptides according to the invention, wherein the amino terminus is (B4)HN—, wherein B4=H.

In a further embodiment, the invention relates to peptides according to the invention, wherein the carboxy terminus of said peptide is —C(=O)—B1, wherein B1=OH.

Several methods can be used to stabilise peptides against degradation and to decrease the ability of peptides to react with other compounds, agents and/or peptides/proteins e.g. in plasma. The invention also relates to peptides according to the invention modified by such methods known in the art. In a preferred embodiment, the invention relates to peptides according to the invention, wherein the amino terminus of the peptide is modified by acetylation. Thus, in a preferred embodiment, the invention relates to peptides according to the invention, wherein the amino terminus is (B6)HN—, wherein B6=B4-C(=O)—, and B4=CH$_3$. In another preferred embodiment, the invention relates to peptides according to the invention, wherein the carboxy terminus of the peptide is modified by amidation. Thus, the invention relates to peptides according to the invention, wherein the carboxy terminus of said peptide is —C(=O)—B1, wherein B1=NH$_2$.

In the broadest aspect of the invention, X is selected from Lys-Lys-Lys-Lys-Lys-Lys (SEQ ID NO: 37), Glu-Lys-Lys-Lys-Lys-Lys (SEQ ID NO: 38), Lys-Glu-Lys-Lys-Lys-Lys (SEQ ID NO: 39), Lys-Lys-Glu-Lys-Lys-Lys (SEQ ID NO: 40), Lys-Lys-Lys-Glu-Lys-Lys (SEQ ID NO: 41), Lys-Lys-Lys-Lys-Glu-Lys (SEQ ID NO: 42), Lys-Lys-Lys-Lys-Lys-Glu (SEQ ID NO: 43), Glu-Glu-Lys-Lys-Lys-Lys (SEQ ID NO: 44), Glu-Lys-Glu-Lys-Lys-Lys (SEQ ID NO: 45), Glu-Lys-Lys-Glu-Lys-Lys (SEQ ID NO: 46), Glu-Lys-Lys-Lys-Glu-Lys (SEQ ID NO: 47), Glu-Lys-Lys-Lys-Lys-Glu (SEQ ID NO: 48), Lys-Glu-Glu-Lys-Lys-Lys (SEQ ID NO: 49), Lys-Glu-Lys-Glu-Lys-Lys (SEQ ID NO: 50), Lys-Glu-Lys-Lys-Glu-Lys (SEQ ID NO: 51), Lys-Glu-Lys-Lys-Lys-Glu (SEQ ID NO: 52), Lys-Lys-Glu-Glu-Lys-Lys (SEQ ID NO: 53), Lys-Lys-Glu-Lys-Glu-Lys (SEQ ID NO: 54), Lys-Lys-Glu-Lys-Lys-Glu (SEQ ID NO: 55), Lys-Lys-Lys-Glu-Glu-Lys (SEQ ID NO: 56), Lys-Lys-Lys-Glu-Lys-Glu (SEQ ID NO: 57), Lys-Lys-Lys-Lys-Glu-Glu (SEQ ID NO: 58), Glu-Glu-Glu-Lys-Lys-Lys (SEQ ID NO: 59), Glu-Glu-Lys-Glu-Lys-Lys (SEQ ID NO: 60), Glu-Glu-Lys-Lys-Glu-Lys (SEQ ID NO: 61), Glu-Glu-Lys-Lys-Lys-Glu (SEQ ID NO: 62), Glu-Lys-Glu-Glu-Lys-Lys (SEQ ID NO: 63), Glu-Lys-Glu-Lys-Glu-Lys (SEQ ID NO: 64), Glu-Lys-Glu-Lys-Lys-Glu (SEQ ID NO: 65), Glu-Lys-Lys-Glu-Glu-Lys (SEQ ID NO: 66), Glu-Lys-Lys-Glu-Lys-Glu (SEQ ID NO: 67), Glu-Lys-Lys-Lys-Glu-Glu (SEQ ID NO: 68), Lys-Lys-Glu-Glu-Glu-Lys (SEQ ID NO: 69), Lys-Lys-Glu-Lys-Glu-Glu (SEQ ID NO: 70), Lys-Lys-Glu-Glu-Lys-Glu (SEQ ID NO: 71), Lys-Lys-Glu-Glu-Glu-Lys (SEQ ID NO: 72), Lys-Glu-Lys-Lys-Glu-Glu (SEQ ID NO: 73), Lys-Glu-Lys-Glu-Lys-Glu (SEQ ID NO: 74), Lys-Glu-Lys-Glu-Glu-Lys (SEQ ID NO: 75), Lys-Glu-Glu-Lys-Lys-Glu (SEQ ID NO: 76), Lys-Glu-Glu-Lys-Glu-Lys (SEQ ID NO: 77), Lys-Glu-Glu-Glu-Lys-Lys (SEQ ID NO: 78), Lys-Lys-Glu-Glu-Glu-Glu (SEQ ID NO: 79), Lys-Glu-Lys-Glu-Glu-Glu (SEQ ID NO: 80), Lys-Glu-Glu-Lys-Glu-Glu (SEQ ID NO: 81), Lys-Glu-Glu-Glu-Lys-Glu (SEQ ID NO: 82), Lys-Glu-Glu-Glu-Glu-Lys (SEQ ID NO: 83), Glu-Lys-Lys-Glu-Glu-Glu (SEQ ID NO: 84), Glu-Lys-Glu-Lys-Glu-Glu (SEQ ID NO: 85), Glu-Lys-Glu-Glu-Lys-Glu (SEQ ID NO: 86), Glu-Lys-Glu-Glu-Glu-Lys (SEQ ID NO: 87), Glu-Glu-Lys-Lys-Glu-Glu (SEQ ID NO: 88), Glu-Glu-Lys-Glu-Lys-Glu (SEQ ID NO: 89), Glu-Glu-Lys-Glu-Glu-Lys (SEQ ID NO: 90), Glu-Glu-Glu-Lys-Lys-Glu (SEQ ID NO: 91), Glu-Glu-Glu-Lys-Glu-Lys (SEQ ID NO: 92), Glu-Glu-Glu-Glu-Lys-Lys (SEQ ID NO: 93), Lys-Glu-Glu-Glu-Glu-Glu (SEQ ID NO: 94), Glu-Lys-Glu-Glu-Glu-Glu (SEQ ID NO: 95), Glu-Glu-Lys-Glu-Glu-Glu (SEQ ID NO: 96), Glu-Glu-Glu-Lys-Glu-Glu (SEQ ID NO: 97), Glu-Glu-Glu-Glu-Lys-Glu (SEQ ID NO: 98), Glu-Glu-Glu-Glu-Glu-Lys (SEQ ID NO: 99), Glu-Glu-Glu-Glu-Glu-Glu (SEQ ID NO: 100)

Presently preferred peptides of the invention are stabilised compounds of the following peptide sequences:

```
                                                      (SEQ ID NO: 1)
Lys-Lys-Lys-Lys-Lys-Lys-Ser-Tyr-Ser-Met-Glu-His-Phe-Arg-Trp-Gly-Lys-Pro-Val (SEQ ID NO: 2)
Glu-Glu-Glu-Glu-Glu-Glu-Ser-Tyr-Ser-Met-Glu-His-Phe-Arg-Trp-Gly-Lys-Pro-Val (SEQ ID NO: 3)
Lys-Lys-Lys-Lys-Lys-Lys-Ser-Tyr-Ser-Met-Glu-His-Phe-Arg-Trp-Gly-Lys-Pro-(D-Val)
```

```
                                                         (SEQ ID NO: 4)
Glu-Glu-Glu-Glu-Glu-Glu-Ser-Tyr-Ser-Met-Glu-His-Phe-Arg-Trp-Gly-Lys-Pro-(D-Val)

(SEQ ID NO: 5)
Lys-Lys-Lys-Lys-Lys-Lys-Ser-Tyr-Ser-Nle-Glu-His-(D-Phe)-Arg-Trp-Gly-Lys-Pro-Val (SEQ ID NO: 6)
Glu-Glu-Glu-Glu-Glu-Glu-Ser-Tyr-Ser-Nle-Glu-His-(D-Phe)-Arg-Trp-Gly-Lys-Pro-Val (SEQ ID NO: 7)
Lys-Lys-Lys-Lys-Lys-Lys-Ser-Tyr-Ser-Nle-Glu-His-(D-Phe)-Arg-Trp-Gly-Lys-Pro-(D-Val)

(SEQ ID NO: 8)
Glu-Glu-Glu-Glu-Glu-Glu-Ser-Tyr-Ser-Nle-Glu-His-(D-Phe)-Arg-Trp-Gly-Lys-Pro-(D-Val)

(SEQ ID NO: 9)
Lys-Lys-Lys-Lys-Lys-Lys-Ser-Tyr-Ser-Nle-Glu-His-D-Nal-Arg-Trp-Gly-Lys-Pro-Val (SEQ ID NO: 10)
Glu-Glu-Glu-Glu-Glu-Glu-Ser-Tyr-Ser-Nle-Glu-His-D-Nal-Arg-Trp-Gly-Lys-Pro-Val (SEQ ID NO: 11)
Lys-Lys-Lys-Lys-Lys-Lys-Ser-Tyr-Ser-Nle-Glu-His-D-Nal-Arg-Trp-Gly-Lys-Pro-(D-Val)

(SEQ ID NO: 12)
Glu-Glu-Glu-Glu-Glu-Glu-Ser-Tyr-Ser-Nle-Glu-His-D-Nal-Arg-Trp-Gly-Lys-Pro-(D-Val)

(SEQ ID NO: 13)
Lys-Lys-Lys-Lys-Lys-Lys-Ser-Ser-Ile-Ile-Ser-His-Phe-Arg-Trp-Gly-Lys-Pro-Val (SEQ ID NO: 14)
Glu-Glu-Glu-Glu-Glu-Glu-Ser-Ser-Ile-Ile-Ser-His-Phe-Arg-Trp-Gly-Lys-Pro-Val (SEQ ID NO: 15)
Lys-Lys-Lys-Lys-Lys-Lys-Ser-Ser-Ile-Ile-Ser-His-Phe-Arg-Trp-Gly-Lys-Pro-(D-Val)

(SEQ ID NO: 16)
Glu-Glu-Glu-Glu-Glu-Glu-Ser-Ser-Ile-Ile-Ser-His-Phe-Arg-Trp-Gly-Lys-Pro-(D-Val)

(SEQ ID NO: 17)
Lys-Lys-Lys-Lys-Lys-Lys-Ser-Ser-Ile-Ile-Ser-His-(D-Phe)-Arg-Trp-Gly-Lys-Pro-Val (SEQ ID NO: 18)
Glu-Glu-Glu-Glu-Glu-Glu-Ser-Ser-Ile-Ile-Ser-His-(D-Phe)-Arg-Trp-Gly-Lys-Pro-Val (SEQ ID NO: 19)
Lys-Lys-Lys-Lys-Lys-Lys-Ser-Ser-Ile-Ile-Ser-His-(D-Phe)-Arg-Trp-Gly-Lys-Pro-(D-Val)

(SEQ ID NO: 20)
Glu-Glu-Glu-Glu-Glu-Glu-Ser-Ser-Ile-Ile-Ser-His-(D-Phe)-Arg-Trp-Gly-Lys-Pro-(D-Val)

(SEQ ID NO: 21)
Lys-Lys-Lys-Lys-Lys-Lys-Ser-Ser-Ile-Ile-Ser-His-D-Nal-Arg-Trp-Gly-Lys-Pro-Val (SEQ ID NO: 22)
Glu-Glu-Glu-Glu-Glu-Glu-Ser-Ser-Ile-Ile-Ser-His-D-Nal-Arg-Trp-Gly-Lys-Pro-Val (SEQ ID NO: 23)
Lys-Lys-Lys-Lys-Lys-Lys-Ser-Ser-Ile-Ile-Ser-His-D-Nal-Arg-Trp-Gly-Lys-Pro-(D-Val)

(SEQ ID NO: 24)
Glu-Glu-Glu-Glu-Glu-Glu-Ser-Ser-Ile-Ile-Ser-His-D-Nal-Arg-Trp-Gly-Lys-Pro-(D-Val)

(SEQ ID NO: 25)
Lys-Lys-Lys-Lys-Lys-Lys-Met-Glu-His-Phe-Arg-Trp-Gly-Lys-Pro-Val (SEQ ID NO: 26)
Glu-Glu-Glu-Glu-Glu-Glu-Met-Glu-His-Phe-Arg-Trp-Gly-Lys-Pro-Val (SEQ ID NO: 27)
Lys-Lys-Lys-Lys-Lys-Lys-Met-Glu-His-Phe-Arg-Trp-Gly-Lys-Pro-(D-Val)

(SEQ ID NO: 28)
Glu-Glu-Glu-Glu-Glu-Glu-Met-Glu-His-Phe-Arg-Trp-Gly-Lys-Pro-(D-Val)

(SEQ ID NO: 29)
Lys-Lys-Lys-Lys-Lys-Lys-Nle-Glu-His-(D-Phe)-Arg-Trp-Gly-Lys-Pro-Val (SEQ ID NO: 30)
Glu-Glu-Glu-Glu-Glu-Glu-Nle-Glu-His-(D-Phe)-Arg-Trp-Gly-Lys-Pro-Val,
```

-continued

```
                                                          (SEQ ID NO: 31)
Lys-Lys-Lys-Lys-Lys-Lys-Nle-Glu-His-(D-Phe)-Arg-Trp-Gly-Lys-Pro-(D-Val)

(SEQ ID NO: 32)
Glu-Glu-Glu-Glu-Glu-Glu-Nle-Glu-His-(D-Phe)-Arg-Trp-Gly-Lys-Pro-(D-Val)

(SEQ ID NO: 33)
Lys-Lys-Lys-Lys-Lys-Lys-Nle-Glu-His-D-Nal-Arg-Trp-Gly-Lys-Pro-Val (SEQ ID NO: 34)
Glu-Glu-Glu-Glu-Glu-Glu-Nle-Glu-His-D-Nal-Arg-Trp-Gly-Lys-Pro-Val (SEQ ID NO: 35)
Lys-Lys-Lys-Lys-Lys-Lys-Nle-Glu-His-D-Nal-Arg-Trp-Gly-Lys-Pro-(D-Val),
and (SEQ ID NO: 36)
Glu-Glu-Glu-Glu-Glu-Glu-Nle-Glu-His-D-Nal-Arg-Trp-Gly-Lys-Pro-(D-Val).
```

The stabilisation may be performed by modifying the N-terminally and/or C-terminal of the peptide as described above, such as e.g. to acetylate the N-terminal of the peptide of the invention and/or to amidate the C-terminal of the peptide of the invention.

The amino acid sequences are given by the known three-letter code for the natural amino acids. Modifications and substitions of naturally amino acid residues are abbreviated as follows: Nle is the abbreviation for Norleucine. D-Nal is the abbreviation for beta-2-naphthyl-d-alanine. D-Val (D-valine) is the abbreviation for the D-configuration of valine. D-Phe (D-phenylalanine) is the abbreviation for the D-configuration of Phenylalanine.

In a preferred embodiment, the invention relates to a peptide, which is a N-terminally acetylated and C-terminally amidated compound of:

```
                                                          (SEQ ID NO: 1)
Lys-Lys-Lys-Lys-Lys-Lys-Ser-Tyr-Ser-Met-Glu-His-Phe-Arg-Trp-Gly-Lys-Pro-Val.
```

In yet another preferred embodiment, the invention relates to a peptide according to the invention, which is a N-terminally acetylated and C-terminally amidated compound of:

```
                                                          (SEQ ID NO: 2)
Glu-Glu-Glu-Glu-Glu-Glu-Ser-Tyr-Ser-Met-Glu-His-Phe-Arg-Trp-Gly-Lys-Pro-Val
```

In still another preferred embodiment, the invention relates to a peptide according to the invention, which is a N-terminally acetylated and C-terminally amidated compound of:

```
                                                          (SEQ ID NO: 3)
Lys-Lys-Lys-Lys-Lys-Lys-Ser-Tyr-Ser-Met-Glu-His-Phe-Arg-Trp-Gly-Lys-Pro-(D-Val).
```

In yet a preferred embodiment, the invention relates to a peptide according to the invention, which is a N-terminally acetylated and C-terminally amidated compound of:

```
                                                          (SEQ ID NO: 5)
Lys-Lys-Lys-Lys-Lys-Lys-Ser-Tyr-Ser-Nle-Glu-His-(D-Phe)-Arg-Trp-Gly-Lys-Pro-Val.

(SEQ ID NO: 9)
Lys-Lys-Lys-Lys-Lys-Lys-Ser-Tyr-Ser-Nle-Glu-His-(D-Nal)-Arg-Trp-Gly-Lys-Pro-Val.
```

In yet another preferred embodiment, the invention relates to a peptide according to the invention, which is a N-terminally acetylated and C-terminally amidated compound of:

In a further preferred embodiment, the invention relates to a peptide according to the invention, which is a N-terminally acetylated and C-terminally amidated compound of:

```
                                                      (SEQ ID NO: 13)
Lys-Lys-Lys-Lys-Lys-Lys-Ser-Ser-Ile-Ile-Ser-His-Phe-Arg-Trp-Gly-Lys-Pro-Val.
```

In another preferred embodiment, the invention relates to a peptide according to the invention, which is a N-terminally acetylated and C-terminally amidated compound of:

```
                                                       (SEQ ID NO: 17)
Lys-Lys-Lys-Lys-Lys-Lys-Ser-Ser-Ile-Ile-Ser-His-(D-Phe)-Arg-Trp-Gly-Lys-Pro-Val.
```

As described above, the peptides of the invention possess an increased therapeutical effect and/or an increased maximal response and/or increased maximal efficacy compared to the naturally occurring peptide α-MSH.

The inventor has examined the biological effects of some of the peptides of the invention:

needed to give maximal inhibition of TNF-α accumulation, than the native melanocyte-stimulating hormone, α-MSH (Examples 1-7).

The inventor has also investigated the effect of the seven peptides listed above (SEQ ID NO: 1*, SEQ ID NO: 2*, SEQ ID NO: 3*, SEQ ID NO: 5*, SEQ ID NO: 9*, SEQ ID NO: 13* and SEQ ID NO: 17*, all *acetylated in the N-terminal and amidated in the C-terminal) in a setup where systemic inflammation were induced by intravenous infusion of LPS in rats (experimental setup 2). It was shown that the peptides significantly inhibit LPS induced TNF-α accumulation in circulating blood. Surprisingly, all seven peptides (SEQ ID NO: 1*, SEQ ID NO: 2*, SEQ ID NO: 3*, SEQ ID NO: 5*, SEQ ID NO: 9*, SEQ ID NO: 13* and SEQ ID NO: 17*, all *acetylated in the N-terminal and amidated in the C-terminal)

```
Ac-(Lys)₆-Ser-Tyr-Ser-Met-Glu-His-Phe-Arg-Trp-Gly-Lys-Pro-Val-NH₂
(SEQ ID NO: 1 *acetylated in the N-terminal and amidated in the C-terminal), Ac-(Glu)₆-Ser-Tyr-Ser-Met-Glu-His-Phe-Arg-Trp-Gly-Lys-Pro-Val-NH₂
(SEQ ID NO: 2 *acetylated in the N-terminal and amidated in the C-terminal), Ac-(Lys)₆-Ser-Tyr-Ser-Met-Glu-His-Phe-Arg-Trp-Gly-Lys-Pro-(D-Val)-NH₂
(SEQ ID NO: 3 *acetylated in the N-terminal and amidated in the C-terminal), Ac-(Lys)₆-Ser-Tyr-Ser-Nle-Glu-His-(D-Phe)-Arg-Trp-Gly-Lys-Pro-Val-NH2
(SEQ ID NO: 5 *acetylated in the N-terminal and amidated in the C-terminal), Ac-(Lys)₆-Ser-Tyr-Ser-Nle-Glu-His-(D-Nal)-Arg-Trp-Gly-Lys-Pro-Val-NH2
(SEQ ID NO: 9 *acetylated in the N-terminal and amidated in the C-terminal), Ac-(Lys)₆-Ser-Ser-Ile-Ile-Ser-His-Phe-Arg-Trp-Gly-Lys-Pro-Val-NH2
(SEQ ID NO: 13 *acetylated in the N-terminal and amidated in the C-terminal), Ac-(Lys)₆-Ser-Ser-Ile-Ile-Ser-His-(D-Phe)-Arg-Trp-Gly-Lys-Pro-Val-NH2
(SEQ ID NO: 17 *acetylated in the N-terminal and amidated in the C-terminal)
```

In general, "Ac-" indicates that the peptide of the invention is acetylated in the N-terminal, and "—NH2" indicates that the peptide of the invention is amidated in the C-terminal.

In a suspension of human leucocytes (experimental setup 1), all seven peptides dose-dependently inhibit LPS induced TNF-α accumulation (Examples 1-7). Surprisingly, it was where able to inhibit TNF-α concentration in circulating blood to a higher degree than the native melanocyte-stimulating hormone α-MSH (examples 1-7).

The inventor has also investigated the effect of the peptides:

```
Ac-(Lys)₆-Ser-Tyr-Ser-Met-Glu-His-Phe-Arg-Trp-Gly-Lys-Pro-Val-NH₂
   (SEQ ID NO: 1 *acetylated in the N-terminal and amidated in the C-terminal),
and Ac-(Lys)₆-Ser-Tyr-Ser-Nle-Glu-His-D-Phe-Arg-Trp-Gly-Lys-Pro-Val-NH2
   (SEQ ID NO: 5 *acetylated in the N-terminal and amidated in the C-terminal)
```

TNF-α accumulation (Examples 1-7). Surprisingly, it was found that all seven peptides were more effective, defined as the maximal inhibitory effect on TNF-α production, as well as more potent, defined as the concentration of the compound in a setup where inflammation were induced by inhalation of LPS in rats (experimental setup 3), and shown that the two peptides (SEQ ID NO:1* and 5*) significantly inhibits LPS induced eosinophil accumulation within the lungs (examples 1 and 2). Surprisingly, peptide (SEQ ID NO: 5*) in addition to this effect on eosinophils also markedly inhibited neutrophil infiltration to a much higher degree than was found in rats treated with the native melanocyte-stimulating hormone, α-MSH (example 2).

Temporal ischemia of the kidney is frequently seen as a consequence of reduced blood pressure, hypovolemia, surgical interventions that involves reduction in renal and/or aortic blood flow, or associated with septicemia. This results in ischemia-induce acute renal failure, which for a large fraction deteriorates into chronic renal failure. Currently no efficient treatment exists to prevent the development of renal failure. A common finding in the post ischemic phase is the development of urinary concentration defects with the formation of increased production of solute free urine.

Ischemia-induced experimental acute renal failure (ARF) induced by ischemia and reperfusion in rats is known to cause characteristic structural alterations in renal tubule epithelia in association with an impairment of urinary concentrating mechanism. This ischemia-induced ARF model provides an appropriate setting to evaluate the effect of a MSH analogue in ischemia-induced injury. The present inventor has investigated the effect of the peptide Ac-(Lys)$_6$-Ser-Tyr-Ser-Met-Glu-His-Phe-Arg-Trp-Gly-Lys-Pro-Val-NH$_2$ (SEQ ID NO: 1 *acetylated in the N-terminal and amidated in the C-terminal) and compared the effect of the peptide to the effect of the native peptide α-MSH in severe acute renal failure induced temporal bilateral occlusion of the renal arteries (experimental setup 6). When evaluated five days after the temporal renal artery occlusion, rats treated with vehicle developed polyuria defined by a 101% higher diuresis as the control rats, which had been subjected to sham occlusion of the renal arteries. Surprisingly, the compound (SEQ ID NO: 1 *acetylated in the N-terminal and amidated in the C-terminal) given in the same molar amount as the native peptide α-MSH, completely normalized the diuresis indicating that the peptide has the ability to protects against ischemia induced ARF, whereas treatment with the native peptide in this setting was unable to normalize the urine production.

Acute myocardial infarction (AMI) is one of the most common causes of death in the developed countries. AMI almost always occurs in patients with coronary atheroma because of sudden coronary thrombosis. Today, fibrinolytic therapy or primary percutaneous transluminal coronary angioplasty (PTCA) are standard treatments and can achieve early reperfusion in 50-70% of patients (spontaneous reperfusion rate is less than 30%). The goal of reperfusion is to reduce the size of the infarction, thereby reducing the development of impaired myocardial function. The overall effect of fibrinolysis/PTCA is a 20% reduction in short and long term mortality. However, AMI is associated with an inflammatory reaction, which is a prerequisite for healing and scar formation. Coronary artery occlusion critically reduces blood flow to the portion of the myocardium, which markedly impairs the energy metabolism. Significant duration of ischemia (>20 min) induces infarction and results in an inflammatory response, which is both accelerated and augmented when the ischemic myocardium is reperfused.

Myocardial ischemia/reperfusion (MIR) activates not only a classical inflammatory reperfusion response with neutrophil-infiltration, but also myocardial cytokine gene expression including tumor necrosis factor-α (TNF-α), interleukin (IL)-1β, IL-6, IL-8, interferon-γ, and intercellular adhesion molecule-1 (ICAM-1). This local myocardial over-expression of cytokines may playa critical role not only in the modulation of the size of the infarction, but also in the progression of the myocardial dysfunction, including vascular wall remodeling, heart failure, and cardiac hypertrophy. Furthermore, it has been suggested that locally produced TNF-χ contributes to postischemic myocardial dysfunction via direct depression of contractility and induction of apoptosis.

An increasing number of experimental studies have shown that anti-inflammatory/anti-oxidative/anti-apoptotic strategies have the ability to reduce infarct size in animal models of MIR. However, no clinical studies have shown significant effects in humans.

In a model of myocardial ischemia/reperfusion in rats in which the left anterior coronary artery was occluded for 60 minutes, treatment with a peptide according to the invention was given just prior to removal of the coronary artery occlusion and the rats were then followed for another three hours. Then the ability of the peptides to reduce infarction size was evaluated and compared to the effect of the native peptide α-MSH (experimental setup 5).

Surprisingly all three peptides:

```
Ac-(Lys)₆-Ser-Tyr-Ser-Met-Glu-His-Phe-Arg-Trp-Gly-Lys-Pro-Val-NH₂
(SEQ ID NO: 1 *acetylated in the N-terminal and amidated in the C-terminal), Ac-(Lys)₆-Ser-Tyr-Ser-Nle-Glu-His-D-Phe-Arg-Trp-Gly-Lys-Pro-Val-NH2
(SEQ ID NO: 5 *acetylated in the N-terminal and amidated in the C-terminal),
and Ac-(Lys)₆-Ser-Tyr-Ser-Nle-Glu-His-D-Nal-Arg-Trp-Gly-Lys-Pro-Val-NH2
(SEQ ID NO: 9 *acetylated in the N-terminal and amidated in the C-terminal)
``` reduced the infarction size to a higher degree as the native peptide α-MSH (examples 1, 3-4).

In light of the functional properties of the peptides described above and in the examples, the invention relates to peptides having at least one of the following properties:

a) inhibits LPS-induced TNF-α production by human leucocytes
b) inhibits inflammation induced eosinophil infiltration within the lungs
c) inhibits inflammation induced neutrophil infiltration within the lungs
d) inhibits inflammation induced TNF-α accumulation in circulating blood
e) reduces ischemia-induced acute renal failure
f) reduces myocardiac infarct size
g) reduces the degree of post myocardial infarctional heart failure
h) reduces pulmonary vascular hypertension
i) reduces cisplatin induced renal failure The peptide may have more than one of these properties, such as e.g. 2, 3, 4, 5, 6, 7, 8 or all of the above properties. These properties can be tested as outlined in the examples.

As described above, the α-MSH analogues of the invention are characterised by having an increased efficacy compared to the native α-MSH.

In this specification and claims, the term "efficacy" is defined as maximal response obtainable by a compound. The α-MSH analogues of the invention are able to produce a higher maximal response compared to the native α-MSH in the various experiments described in the examples.

Preferably, an α-MSH analogue of the invention inhibits LPS-induced TNF-α production by human leucocytes by a minimum of 10%, more preferably by 25% and most preferably by 40% compared to α-MSH.

Furthermore, an α-MSH analogue of the invention may inhibit inflammation induced eosinophil infiltration within the lungs as measured by the ability to reduce the number of eosinofils within fluid collected by broncho-alveolar lavage or a comparably method. The minimal expected effect is a 10%, more preferably a 25% and most preferably a 50% reduction in eosinophils is found when compared to α-MSH.

Moreover, an α-MSH analogue of the invention may inhibit inflammation induced neutrophil infiltration within the lungs as measured by the ability to reduce the number of neutrophils within fluid collected by broncho-alveolar lavage or a comparably method. The minimal expected effect is a 10%, more preferably a 20% and most preferably a 40% reduction in neutrophils is found when compared to α-MSH.

An α-MSH analogue of the invention may also inhibit inflammation induced TNF-α accumulation in circulating blood by a minimum of 10%, more preferably by 25% and most preferably by 40% compared to α-MSH.

Moreover, an α-MSH analogue of the invention may reduce ischemia-induced acute renal failure as measured by the ability to reduce the degree of post ischemic polyuria. The minimal expected effect is a 10%, more preferably a 30% and most preferably a 50% reduction in polyuria is found when compared to α-MSH.

Furthermore, an α-MSH analogue of the invention may reduce myocardiac infarct size as evidenced by the ability to reduce the size of the necrotic area within the ischemic myocardium. The minimal expected effect is a 10%, more preferably a 20% and most preferably a 30% reduction in infarction size is found when compared to α-MSH.

In a further aspect, an α-MSH analogue of the invention may reduce the degree of post myocardial infarctional heart failure as evidenced by cardiac performance evaluated through direct measurement of left ventricular end diastolic pressure or a similar quantitative measurement. The minimal expected effect is a 10%, more preferably a 20% and most preferably a 25% reduction in the degree of heart failure is found when compared to α-MSH.

In a yet further aspect, an α-MSH analogue of the invention may reduce pulmonary vascular hypertension. The minimal expected effect is a 10%, more preferably a 20% and most preferably a 30% reduction in pulmonary artery pressure is found when compared to αMSH.

In another aspect, an α-MSH analogue of the invention may reduce cisplatin induced renal failure. The minimal expected effect is a 10%, more preferably a 20% and in the most preferable setting a 30% reduction in hypomagnesia and/or Glomerular filtration rate found when compared to αMSH.

As earlier described, the native peptide α-melanocyte stimulating hormone (α-MSH) is known as the native agonist for the type 1, the type 3, the type 4 and the type 5 melanocortin (MC) receptor, while ACTH is the native ligand to the Type 2 receptor (MC2). As the peptides comprise the amino acid sequence of α-MSH or an analogue thereof, the peptides of the invention have the ability to stimulate one or more melanocortin receptors, i.e melanocortin receptor type 1, 3, 4, or 5.

Methods of Preparation of Peptides of the Invention

The peptides of the invention may be prepared by methods known per se in the art. Thus, the α-MSH, α-MSH-variants, α-MSH analogues and the X motif may be prepared by standard peptide-preparation techniques such as solution synthesis or Merrifield-type solid phase synthesis.

In one possible synthesis strategy, the peptides of the invention may be prepared by solid phase synthesis by first constructing the pharmacologically active peptide sequence (α-MSH, α-MSH-variant or α-MSH analogue) using well-known standard protection, coupling and deprotection procedures, thereafter sequentially coupling the amino acid sequence of the motif X on the active peptide in a manner similar to the construction of the active peptide, and finally cleaving off the entire peptide from the carrier. This strategy yields a peptide, wherein the peptide sequence X is covalently bound to the pharmacologically active peptide at the N-terminal nitrogen atom of the peptide.

Another possible strategy is to prepare the sequence of the α-MSH peptide/analogue and the X-motif (or parts thereof) separately by solution synthesis, solid phase synthesis, recombinant techniques, or enzymatic synthesis, followed by coupling of the two sequences by well-known segment condensation procedures, either in solution or using solid phase techniques or a combination thereof. In one embodiment, the α-MSH peptide/analogue may be prepared by recombinant DNA methods and the X motif may be prepared by solid phase synthesis. The conjugation of the α-MSH peptide/analogue and the X motif may be carried out by using chemical ligation. This technique allows for the assembling of totally unprotected peptide segments in a highly specific manner (Liu et al., 1996). The conjugation can also be performed by protease-catalysed peptide bond formation, which offers a highly specific technique to combine totally unprotected peptide segments via a peptide bond (Kullmann, 1987).

Examples of suitable solid support materials (SSM) are e.g., functionalised resins such as polystyrene, polyacrylamide, polydimethylacrylamide, polyethyleneglycol, cellulose, polyethylene, polyethyleneglycol grafted on polystyrene, latex, dynabeads, etc.

It should be understood that it may be necessary or desirable that the C-terminal amino acid of the peptide sequence of the X-motif or the C-terminal amino acid of the α-MSH, α-MSH-variant, or α-MSH analogue is attached to the solid support material by means of a common linker such as 2,4-dimethoxy-4'-hydroxy-benzophenone, 4-(4-hydroxy-methyl-3-methoxyphenoxy)-butyric acid, 4-hydroxy-methyl-benzoic acid, 4-hydroxymethyl-phenoxyacetic acid, 3-(4-hydroxymethylphenoxy)propionic acid, and p-[(R,S)-a[1-(9H-fluoren-9-yl)methoxyformamido]-2,4-dimethoxybenzyl]-phenoxy-acetic acid.

The peptides of the invention may be cleaved from the solid support material by means of an acid such as trifluoracetic acid, trifluoromethanesulfonic acid, hydrogen bromide, hydrogen chloride, hydrogen fluoride, etc. optionally in combination with one or more "scavengers" suitable for the purpose, e.g., ethanedithiol, triisopropylsilane, phenol, thioanisole, etc., or the peptide conjugate of the invention may be cleaved from the solid support by means of a base such as ammonia, hydrazine, an alkoxide, such as sodium ethoxide, an hydroxide, such as sodium hydroxide, etc.

The peptides of the invention may also be prepared by means of recombinant DNA-technology using general methods and principles known to the person skilled in the art. A nucleic acid sequence encoding the peptide of the invention may be prepared synthetically by established standard methods, e.g., the phosphoamidite method. According to the phosphoamidite method, oligonucleotides are synthesized, e.g., in an automatic DNA synthesizer, purified, annealed, ligated and cloned in suitable vectors.

The nucleic acid sequence encoding the peptide of the invention is then inserted into a recombinant expression vector, which may be any vector which may conveniently be subjected to recombinant DNA procedures. The choice of vector will often depend on the host cell into which it is to be introduced. Thus, the vector may be an autonomously replicating vector, i.e., a vector, which exists as an extrachromosomal entity, the replication of which is independent of chromosomal replication, e.g., a plasmid. Alternatively, the vector may be one which, when introduced into a host cell, is integrated into the host cell genome and replicated together with the chromosome(s) into which it has been integrated.

In the vector, the nucleic acid sequence encoding the peptide of the present invention should be operably connected to a suitable promoter sequence. The promoter may be any nucleic acid sequence, which shows transcriptional activity in the host cell of choice and may be derived from genes encoding proteins either homologous or heterologous to the host cell. Examples of suitable promoters for directing the transcription of the nucleic acid sequence encoding said peptide in mammalian cells are the SV 40 promoter, the MT-1 (metallothionein gene) promoter or the adenovirus 2 major late promoter, a Rous sarcoma virus (RSV) promoter, cytomegalovirus (CMV) promoter and a bovine papilloma virus promoter (BPV). A suitable promoter for use in insect cells is the polyhedrin promoter.

Examples of suitable promoters for directing the transcription of the nucleic acid sequence encoding the peptide of the invention, especially in a bacterial host cell, are the promoters obtained from the *E. coli* lac operon, the *Streptomyces coelicolor* agarase gene (dagA), the *Bacillus subtilis* levansucrase gene (sacB), the *Bacillus licheniformis* alpha-amylase gene (amyL), the *Bacillus stearothermophilus* maltogenic amylase gene (amyM), the *Bacillus amyloliquefaciens* alpha amylase gene (amyQ), the *Bacillus licheniformis* penicillinase gene (penP), the *Bacillus subtilis* xylA and xylB genes, and the prokaryotic beta-lactamase gene, as well as the tac promoter. Further promoters are described in "Useful proteins from recombinant bacteria" in Scientific American, 1980, 242:74-94; and in Sambrook et al., 1989, supra.

Examples of suitable promoters for directing the transcription of the nucleic acid sequence encoding the peptide of the invention in a filamentous fungal host cell are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (as described in U.S. Pat. No. 4,288,627, which is incorporated herein by reference), and hybrids thereof. Particularly preferred promoters for use in filamentous fungal host cells are the TAKA amylase, NA2-tpi (a hybrid of the promoters from the genes encoding *Aspergillus niger* neutral a amylase and *Aspergillus oryzae* triose phosphate isomerase), and glaA promoters.

In a yeast host, useful promoters are obtained from the *Saccharomyces cerevisiae* enolase (ENO-1) gene, the *Saccharomyces cerevisiae* galactokinase gene (GAL1), the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, Yeast 8:423-488.

The nucleic acid sequence encoding said peptide of the invention may also be operably connected to a suitable terminator, such as the human growth hormone terminator. Preferred terminators for filamentous fungal host cells are obtained from the genes encoding *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes encoding *Saccharomyces cerevisiae* enolase, *Saccharomyces cerevisiae* cytochrome C(CYC1), or *Saccharomyces cerevisiae* glyceraldehyde-3-phosphate dehydrogenase. Other useful terminators for yeast host cells are described by Romanos et al., 1992, supra.

The vector may further comprise elements such as polyadenylation signals (e.g., from SV or the adenovirus 5 Elb region), transcriptional enhancer sequences (e.g., the SV 40 enhancer) and translational enhancer sequences (e.g., the ones encoding adenovirus VA RNAs). Furthermore, preferred polyadenylation sequences for filamentous fungal host cells are obtained from the genes encoding *Aspergillus oryzae* TAKA amylase, *Aspergillus niger* glucoamylase, Aspergillus nidulans anthranilate synthase, and *Aspergillus niger* alpha-glucosidase. Useful polyadenylation sequences for yeast host cells are described by Guo and Sherman, 1995, Molecular Cellular Biology 15:5983-5990.

The recombinant expression vector may further comprise a DNA sequence enabling the vector to replicate in the host cell in question. Examples of such a sequence (when the host cell is a mammalian cell) is the SV 40 or polyoma origin of replication. Examples of bacterial origins of replication are the origins of replication of plasmids pBR322, pUC19, pACYC177, pACYC184, pUB110, pE194, pTA1060, and pAMβ1. Examples of origin of replications for use in a yeast host cell are the 2 micron origin of replication, the combination of CEN6 and ARS4, and the combination of CEN3 and ARS1. The origin of replication may be one having a mutation to make its function temperature-sensitive in the host cell (see, e.g., Ehrlich, 1978, Proc. Natl. Acad. Sci. USA 75:1433).

The vector may also comprise a selectable marker, e.g., a gene the product of which complements a defect in the host cell, such as the gene coding for dihydrofolate reductase (DHFR) or one which confers resistance to a drug, e.g., neomycin, geneticin, ampicillin, or hygromycin. Suitable markers for yeast host cells are ADE2, HIS3, LEU2, LYS2, MET3, TRP1, and URA3. A selectable marker for use in a filamentous fungal host cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), and glufosinate resistance markers, as well as equivalents from other species. Preferred for use in an *Aspergillus* cell are the amdS and pyrG markers of *Aspergillus nidulans* or *Aspergillus oryzae* and the bar marker of *Streptomyces hygroscopicus*. Furthermore, selection may be accomplished by cotransformation, e.g., as described in WO 91/17243, where the selectable marker is on a separate vector.

The procedures used to ligate the nucleic acid sequences coding peptide of the invention, the promoter and the terminator, respectively, and to insert them into suitable vectors containing the information necessary for replication, are well known to persons skilled in the art (cf., for instance, Sambrook et al., op. cit.).

The host cell into which the expression vector is introduced may be any cell which is capable of producing the peptide of the invention and is may be a eukaryotic cell, such as invertebrate (insect) cells or vertebrate cells, e.g., *Xenopus laevis* oocytes or mammalian cells, in particular insect and mammalian cells. Examples of suitable mammalian cell lines are the COS (e.g., ATCC CRL 1650), BHK (e.g., ATCC CRL 1632, ATCC CCL 10) or CHO (e.g., ATCC CCL 61) cell lines.

Methods for transfecting mammalian cells and expressing DNA sequences introduced in the cells can be any method known in the art (e.g. MANIATIS, T., E. F. FRITSCH and J. SAMBROOK, 1982 *Molecular Cloning: A Laboratory Manual*. Cold Spring Harbor Laboratory Press, Cold Spring Harbor, N.Y.

The host cell may also be a unicellular pathogen, e.g., a prokaryote, or a non-unicellular pathogen, e.g., a eukaryote. Useful unicellular cells are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis*, and *Bacillus thuringiensis*; or a *Streptomyces* cell, e.g., *Streptomyces lividans* or *Streptomyces murinus*, or gram negative bacteria such as *E. coli* and *Pseudomonas* sp. The transformation of a bacterial host cell may, for instance, be effected by protoplast transformation, by using competent cells, by electroporation, or by conjugation.

The host cell may be a fungal cell. "Fungi" as used herein includes the phyla Ascomycota, Basidiomycota, Chytridiomycota, and Zygomycota as well as the Oomycota and all mitosporic fungi. Representative groups of Ascomycota include, e.g., *Neurospora, Eupenicillium* (=*Penicillium*), *Emericella* (=*Aspergillus*), *Eurotium* (=*Aspergillus*), and the true yeasts listed above. The fungal host cell may also be a yeast cell. "Yeast" as used herein includes ascosporogenous yeast (Endomycetales), basidiosporogenous yeast, and yeast belonging to the Fungi Imperfecti (Blastomycetes). The medium used to culture the cells may be any conventional medium suitable for growing mammalian cells, such as a serum-containing or serum-free medium containing appropriate supplements, or a suitable medium for growing insect, yeast or fungal cells. Suitable media are available from commercial suppliers or may be prepared according to published recipes (e.g, in catalogues of the American Type Culture Collection).

The peptide of the invention produced by the cells may then be recovered from the culture medium by conventional procedures including separating the host cells from the medium by centrifugation or filtration, precipitating the proteinaceous components of the supernatant or filtrate by means of a salt, e.g., ammonium sulphate, purification by a variety of chromatographic procedures, e.g., ion exchange chromatography, affinity chromatography, or the like.

Thus, the present invention relates to methods for the preparation of the peptides according to the invention, by means of recombinant DNA-technology comprising the steps of (a) introducing a nucleic acid sequence encoding said peptide into a host cell and (b) culturing said host cell and (c) isolating said peptide from the culture or (a) culturing a recombinant host cell comprising a nucleic acid sequence encoding said peptide under conditions permitting the production of said peptide and (b) isolating said peptide from the culture.

Use

The invention also relates to peptides according to the invention for use in medicine, in particular for use in connection with one or more of the conditions, disorders or diseases mentioned above or in the following.

In one embodiment, the invention relates to use of one or more peptides according to the invention for the manufacture of a pharmaceutical composition for the treatment or prophylaxis of a condition in the tissue of one or more organs of a mammal. The organ is not limited to, but can be selected from the group consisting of kidney, liver, brain, heart, muscles, bone marrow, skin, skeleton, lungs, the respiratory tract, spleen, exocrine glands, bladder, endocrine glands, reproduction organs including the phallopian tubes, eye, ear, vascular system, the gastroinstestinal tract including small intestines, colon, rectum, and canalis analis and prostate gland.

As described above, the peptides of the invention display increased anti-inflammatory effects and increased capability to prevent ischemic conditions compared to $\alpha$-MSH.

Thus, the present invention relates to use of one or more peptides according to the invention for the manufacture of a pharmaceutical composition for the treatment or prophylaxis of a condition in the tissue of one or more organs of a mammal, wherein said condition is an ischemic or inflammatory condition. The condition can also be due to toxin- or drug-induced cell, tissue or organ failure.

In the present specification and claims, the term "treatment" will generally include treatment of an existing condition as well as prevention of such condition (prophylactic treatment) unless the text specifically excludes this interpretation.

In its broadest concept the invention relates to any condition wherein the normal function of the organ(s) or tissue(s) is altered due to ischemia or inflammation. The injury may include acute and/or chronic injury. Chronic injury includes situations of repetitive injuries alternating with periods of complete or partial recovery of the organ(s) or tissue(s) function.

Ischemia

In the present specification and claims, ischemia is defined as a reduced blood flow to one or more organs resulting in a reduced oxygen delivery and/or utilization by the tissues. Ischemia may occur in one or more organs including (non-listing list): brain, heart, extremities, kidney, spleen, liver, intestine, stomach, lung, eye, skin, muscles, pancreas, endocrine organs and others.

Ischemia induces by reduced/complete arrest in arterial blood supply multiple tissue reactions including neutrophil accumulation, other inflammatory responses and cell death. Ischemia is involved in multiple diseases, associated with major surgery and secondary to other severe diseases. Identification of compounds that can inhibit or prevent (either completely or partially) many of the cell/tissue/organ impairments or destructions occurring as a result of ischemia are of great benefit.

The condition to be treated can be due to or caused by ischemia of the tissue such as in arterial stenosis or any other complete or partial restriction in blood supply. The ischemia may be acute or chronic depending on the severity of the disease and, furthermore, the condition may be reversible or irreversible. An example of a reversible condition may be due to fall in the blood pressure during surgery or other intervention, which affect the blood perfusion of the organ. Accordingly, the condition to be treated may be any decrease in systemic blood flow such as hypotension, which may affect the systemic blood flow to the intestine, heart kidney or any other organ.

In one embodiment, the invention relates to use of a peptide according to the invention for the manufacture of a pharmaceutical composition for the treatment of ischemia, wherein said condition is caused by acute, subacute or chronic ischemia.

Acute, subacute or chronic ischemia of an organ or an extremity or a tissue can be caused by a wide variety of diseases. This includes (non-limiting list) atheromatous disease with thrombosis, embolism from the heart or from blood vessel from any organ, vasospasm, aortic aneurysm or aneurisms in other organs, thoracal or abdominal or dissecting aortic aneurysm, hypotension due to heart disease, hypotension due to systemic disease including infection or allergic reactions, hypotension due to one or more toxic compound or poison(s) or drug(s).

In a second embodiment, the invention relates to use of a peptide according to the invention for the manufacture of a pharmaceutical composition for the treatment of ischemia, wherein said condition is caused by secondary ischemia.

Ischemia secondary to a disease or condition can be observed in one or more of the diseases and condtions selected from: diabetes mellitus, hyperlipidaemia, thromboangiitis obliterans (Buerger's disease), Takayasu's syndrome, arteritis temporalis, mucocutaneous lymph node syndrome (Kawasaki disease), cardiovascular syphilis, connective tissue disorders as Raynaud's disease, phlegmasia coerulae dolens, blood vessel trauma including iatrogene trauma such as cannulation or surgery or organtransplantation. Moreover the list include ischemia caused by surgery of one or more organs, transplantation of one or more organs, surgical insertion transplants, devices, grafts, prostheses or other biomedical compounds or devices.

In a third embodiment, the invention relates to use of a peptide according to the invention, wherein said condition is caused by ischemia due to septic chock or conditions associated with systemic hypotension.

Inflammatory Condition

By the term "an inflammatory condition" is in the present context meant a condition in which mechanisms such as reaction of specific T lymphocytes or antibody with antigen causes the recruitment of inflammatory cells and endogenous mediator chemicals. In some cases, the normal function of the organ or tissue will be altered by an increase in vascular permeability and/or by contraction of visceral smooth muscle. Such inflammatory conditions may give rise to inflammatory diseases.

In one embodiment, the invention relates to use of one or more peptides according to the invention for the manufacture of a pharmaceutical composition for the treatment or prophylaxis of a condition in the tissue of one or more organs of a mammal, wherein said condition is an inflammatory condition.

An inflammatory condition can be caused by inflammatory diseases including (non-limiting list): Arthritis, (including diseases associated with arthritis), osteoartritis, rheumatoid arthritis; spondylarthropathies (e.g. ankylosing spondilitis), reactive arthritis (including arthritis following rheumatic fever), Henoch-Schonlein purpura, and Reiter's disease. Moreover inflammatory diseases include connective tissue disorders such as systemic lupus erythematosus, polymyositis/dermatomyositis, systemic sclerosis, mixed connective tissue disease, sarcoidosis and primary Sjogrens syndrome including keratoconjunctivitis sicca, polymyalgia rheumatica, and other types of vasculitis, crystal deposition diseases (including gout), pyrophosphate arthropathy, acute calcific periarthritis. Moreover inflammatory diseases include juvenile arthritis (Still's disease), psoriasis, osteoarthritis, osteoarthritis secondary to hypermobilty, congenital dysplasias, slipped femoral epiphysis, Perthes' disease, intra-articular fractures, meniscectomy, obesity, recurrent dislocation, repetitive actions, crystal depositions and diseases and metabolic abnormalities of cartilage including pyrophosphate arthropathy, ochronosis, haemochromatosis, avascular necrosis including Sickle Cell disease, therapy with corticoids or other drugs, Caisson disease, septic or infectious arthitis (including tuberculous arthritis, meningococcal arthritis, gonococcal arthritis, *salmonella* arthritis), infective endocarditis (including endocarditis induced by *Streptococcus viridans, Enterococcus Faecalis, Staphylococcus aureus, Staphylocossus epidermidis, Histoplasma, Brucella, Candida* and *Aspergellus* species and *Coxiella Burnetii*), viral arthritis (including infection with rubella, mumps, hepatitis B, HIV or Parvovirus), or recurrent haemarthrosis. Moreover inflammatory diseases include vasculitis such as infective vasculitis due to infections with bacterial species including spirochaetal diseses as Lyme disease, syphilis, rickettsial and mycobacterial infections, fungal, viral or protozoal infections. Moreover inflammatory diseases include non-infective vascultitis including Takayasu's arteritis, Giant Cell Arteritis (Temporal arteritis and polymyalgia rheumatica), Buerger's disease, polyarteritis nodosa, microscopic polyarteritis, Wegener's granulomatose, Churg-Strauss syndrome, vasculitis secondary to connective tissue diseases including Systemic Lupus Erythematosus, Polymyositis/Dermatomyositis, Systemic Sclerosis, Mixed Connetive Tissue Disease, sarcoidosis and Primary Sjogrens syndrome. Moreover inflammatory diseases include vasculitis secondary to rheumatoid arthritis.

Moreover inflammatory diseases include non-infective vasculitis secondary to hypersensibility and leucocytoplastic vasculitis including Serum Sickness, Henoch-Schonlein purpura, Drug induced vasculitis, essential mixed cryoglobulinaemia, hypocomplentaemia, Vasculitis associated with other kinds of malignancy, inflammatory bowel disease and primary biliary cirrhosis, Goodpasture syndrome.

Moreover inflammatory diseases include all kinds of arthritis in children such as Juvenile Chronic arthritis including Still's disease, juvenile rheumatoid arthritis, juvenile ankylosing spondylitis.

Moreover, inflammatory diseases include upper and lower airway diseases such as chronic obstructive pulmonary diseases (COPD), allergic and non-allergic asthma, allergic rhinitis, allergic and non-allergic conjunctivitis. Moreover, inflammatory diseases also include allergic and non-allergic dermatitis.

Moreover inflammatory diseases include all kinds of deposition diseases as Gout, pyrophosphate arthopathy and acute calcific periarthritis.

Moreover inflammatory diseases include all kind of inflammatory conditions causing backpain including infections, septic discitis, tuberculosis, malignancies (such as matastases, myeloma and others), spinal tumours, ancylosing spondylitis, acute disc prolapse, chronic disc disease/osteoarthritis, osteoporosis, and osteomalacia. It also includes Pagets disease, hyperparathyroidism, renal osteodystrophy, spondylolisthesis, spinal senosis congenital abnormalities and fibromyalgia.

Moreover inflammatory diseases include all kinds of soft-tissue rheumatism including bursitis, tenosynovitis or peritendonitis, enthesitis, nerve compression, periarthritis or capsulitis, muscle tension and muscle dysfunction.

Moreover inflammatory diseases include inflammatory diseases of the gastrointestinal system (including stomatitis of all kinds, pemfigus, bulloid pemphigoid and benign mucous membrane pemphigoid), salivary gland diseases (such as sarcoidosis, salivary duct obstruction and Sjogrens syndrome), inflammaton of the oesophagus (e.g. due to gastro-oesophagel reflux or infections with candida species, herpes simplex and cytomegalus virus), inflammatory diseases of the stomach (including acute and chronic gastritis, *helicobacter pylori* infection and Mentriers disease), inflammation of the small intestine (including coeliac disease, gluten sensitive enteropathy, dermatitis herpitiformis, tropical sprue, Whipple's diease, radiation enteritis, systemic amyloidosis, connective tissue disorders including systemic lupus erythematosus, polymyositis/dermatomyositis, systemic sclerosis, mixed connetive tissue disease and sarcoidosis), eosinophilic gastroenteritis, intestinal lympangiectasia, inflammatory bowel disease (including Chrohn's disease and ulcerative colitis), diverticular disease of the colon, and irritable bowel syndrome.

In a preferred embodiment, the invention relates to use of one or more peptides according to the invention for the manufacture of a pharmaceutical composition for the treatment or prophylaxis of a condition in the tissue of one or more organs of a mammal, wherein the condition is an inflammatory condition selected from lung inflammation, artritis, dermatitis, pancreatitis and inflammatory bowel diseases.

Drug Induced Cell, Tissue and Organ Failure

In one embodiment, the present invention relates to use of one or more peptides according to the invention for the manufacture of a pharmaceutical composition for the treatment or prophylaxis of toxin- or drug-induced cell, tissue or organ failure.

In the present specification and claims, "drug induced cell, tissue and organ failure" is defined as changes in the function and/or morphology of a cell a tissue or induced by a pharmacological compound. The pharmacological compound includes but are not restricted to cancer chemotherapeutics including cisplatin, carboplatin, dacarbezine, procarbazine, altretamine, semustine, lomustine, carmustine, busulfan, thiotepa, melphalan, cyclophosphamide, chlorambucil, mechlorethamine, azacitidine, cladribine, cytorabine, fludarabine, fluorouracil, mercaptopurine, metrotrexate, thioguanine, allopurinol, bleomycin, dactinomycin, daunorubicin, docetaxel, doxorubicin (adriamycin), etoposide, idarubicin, irinotecan, mitomycin, paclitaxel, plicamycin, topotecan, vinblastine, vincristine, vinorelbine, amasacrine, asparaginase, hydroxyurea, mititane, mitoxantrone; Antibiotics as aminoglycosides including streptomycin, neomycin, kanamycin, amikacin, gentamicin, tobramycin, sisomicin and nitilmicin; immunodepressive compounds as cyclosporine. tricyclic antidepressants, lithium salts, prenylamine and phenothizine derivatives.

Conditions wherein the normal function of the cell, tissue or organ is altered include conditions associated with ischemia, acute and/or chronic inflammation, allergy, rheumatic diseases, infection including viral, fungal, bacterial infections, prions and other microbes and infectious agents known in the art, all forms of toxic reactions including drug induced toxicity, and acute and chronic injury. Chronic injury includes situations of repetitive injuries alternating with periods of complete or partial recovery of the organ(s) or tissue(s) function. Conditions wherein the normal function of the cell, tissue or organ is altered may also include injury, which is associated with implantation of one or more organs or other devices for transplantation and it is contemplated that the peptides of the invention will also be useful in the treatment or prevention of said conditions. The organ can be from the individual him or herself, the animal itself or from other individuals or animals. This includes: organ transplants, bone transplants, soft tissue implants (silicone implants), metal and plastic implants, or other medical implantable devices. Individual represents humans as well as other mammals.

The condition to be treated may also be caused by a cancer or a by premalignant disorder having an impact on the organ, e.g. on the respiratory system including lung, bronchiole, upper airways, and/or on the heart and/or on the kidney and/or on the gastrointestinal system, including acute leukemia, chronic myelocytic leukemia, chronic lymphocytic leukemia, Hodgkin's disease, lymphosarcoma, myeloma, metastasizing carcinoma of any origin. It is contemplated that the peptides of the invention will also be useful in the treatment or prevention of said conditions.

Furthermore, the condition to be treated may be caused by any disease selected from diabetes mellitus, conditions with increased fasting levels of LDL-Cholesterol, conditions with combined increased fasting levels of LDL-Cholesterol and triglycerid, conditions with increased fasting levels of triglycerid, conditions with increased fasting levels of HDL-Cholesterol, retroperitoneal fibrosis, lupus erythematosus, polyarteritis nodosa, sclerodermia, polymyositis, dermatomyositis, rheumatoid arthritis, anaphylaxis, serum sickness, hemolytic anaemia, and allergic agranulocytosis. It is contemplated that the peptides of the invention will also be useful in the treatment or prevention of said conditions.

Many infections may have an influence on the tissue and disturb the normal function resulting in decreased performance, which may be improved by administration of an effective dose of a peptide of the invention. Such infections include infections by protozoa, virus, bacteria and fungus and include conditions such as AIDS, bacterial septicemia, systemic fungal infections, Rickettsial diseases, toxic shock syndrome, infectious mononucleosis, chlamydia thrachomatis, *chlamydia psittaci*, cytomegalovirus infection, *campylobacter, salmonella*, influenza, poliomyelitis, toxoplasmosis, Lassa Fever, Yellow Fever, billharziose, colibacteria, *enterococcus*, preteus, *klebsiella*, pseudomonas, *staphylococcus aureus, staphylococcus epidermidis, candida albicans*, tuberculosis, mumps, infectious mononucleosis, hepatitis and Coxackie virus The condition to be treated may be associated with a chemical trauma involving one or more toxic substances and/or drugs. Such drugs include tricyclic antidepressants, lithium salts, prenylamine, phenothizine derivatives, cancer chemotherapeutics including cisplatin, carboplatin, dacarbezine, procarbazine, altretamine, semustine, lomustine, carmustine, busulfan, thiotepa, melphalan, cyclophosphamide, chlorambucil, mechlorethamine, azacitidine, cladribine, cytorabine, fludarabine, fluorouracil, mercaptopurine, metrhotrexate, thioguanine, allopurinol, bleomycin, dactinomycin, daunorubicin, docetaxel, doxorubicin (adriamycin), etoposide, idarubicin, irinotecan, mitomycin, paclitaxel, plicamycin, topotecan, vinblastine, vincristine, vinorelbine, amasacrine, asparaginase, hydroxyurea, mititane, mitoxantrone; Antibiotics as aminoglycosides including streptomycin, neomycin, kanamycin, amikacin, gentamicin, tobramycin, sisomicin and nitilmicin; and immunodepressive compounds as cyclosporine. Also physical traumas including electromagnetic radiation may cause damages, which can be alleviated by administration of an effective dose of a α-MSH analogue according to the present invention.

The condition to be treated according to the present invention, may further include connective tissue disease such as scleroderma, systemic lupus erythematosus or by neuromyopathic disorders such as progressive muscular dystrophy of Duchenne's type, Friedreich's ataxia, and myotonic dystrophy. The condition may e.g. be related to the tissue of the intestine of the mammal.

The invention also relates to use of a peptide according to the invention, wherein the condition is selected from the group consisting of myocardial ischemia, angina, pericarditis, myocardial infarction, myocardial ischemia, myocarditis, myxodemia, and endocarditis.

In one embodiment, the invention relates to use of a peptide according to invention, wherein the condition is associated with cardial arrhytmia.

Methods of Treatment

The invention also relates to methods for the treatment or prevention of a condition in the tissue of one or more organs of an individual mammal in need thereof, the method comprising administering an effective dose of one or more peptides according to the invention. Said condition can be an ischemic or inflammatory condition and/or result from toxic effects of poising or drug treatment.

The method of treatment of the invention may be of special benefit in relation to conditions caused by or associated with transplantation of any organ or vessel, including prevention of graft versus host reaction. In such conditions, the entire organ is extremely sensitive to all alterations with respect to nutrition, metabolism, perfusion etc., and the treatment according to the present invention is believed to stabilize the condition and make the tissue more resistant to any situation stressing the function of the organ. The method according to the present invention also encompasses administration of an effective dose of a peptide of the invention to the organ transplant during transport to the recipient, including addition of an effective dose of a peptide of the invention to the transportation medium.

Moreover, the present application provides evidence that treatment with an α-MSH analogue according to the invention in severe diseases such as myocardial ischemia dramatically prevents death and organ dysfunction.

One of the most common heart conditions is intermittent angina or chest pain wherein the treatment according to the invention may be of special interest. Conditions relating to angina include unstable angina, stable angina and Prinzmetal's variant angina.

In a further aspect, the prevention and treatment may be utilized in situations caused by pericarditis, myocardiel infarction, myocardial ischemia, myocarditis, myxodemia, and endocarditis.

The condition to be treated can be associated with cardial arrhythmia. Either as the primary disease or secondary to another condition of the individual. Examples of miscellaneous causes of arrhythmia include acute infections particularly those affecting the lungs, pulmonary embolism, hypotension, shock, anoxaemia or anaemia which can precipitate myocardial ischemia and thus cause arrhythmia. The arrhythmia will aggravate the circulatory disturbance and thereby set up a vicious, self-perpetuating cycle.

It is believed that the treatment according to the present invention will increase the threshold for development of arrhythmia thus preventing the development of the arrhythmia. The effect may by directly on the conduction system or indirectly by acting on a condition tricking or being the cause of the arrhythmia.

A syndrome or an arrhythmia which can be alleviated according to the present method may be either primary or secondary and may be selected from ventricular or supra ventricular tachyarrhythmias, atrioventricular block, sinus node disease, Wolff-Parkinson-White syndrome, Lenégres disease, Lev's disease any syndrome involving an abnormal myocardial connection between atrium and ventricle.

Antiarrhythmic therapy performed with the aim of suppressing an arrhythmia is always associated with a risk of creating new arrhythmias. The arrhythmias may occur as a toxic reaction due to an overdose of the drug. However, particularly during treatment with the group of drugs known as Class IA drugs, arrhythmias can occur as a non dosage-dependent side effect—an idiosyncratic reaction—developing at drug concentrations well within the therapeutic range. According to a further embodiment, the condition may be caused by one or more antiarrhytmic drugs including, digitalis, quinidine, disopyramide, adenosin, aprindine, flecamide, amiodarone, sotalol, meciletine, beta blocking agents, and verapamil.

It is contemplated that treatment with an α-MSH analogue according to the invention will decrease the risk of developing arrythmias due to concommittant treatment with other anti-arrythmic medicament(s).

In a further aspect of the invention, the condition may be characterised by one or more abnormalities as measured by electrocardiography (ECG). The abnormality on the ECG may relate to an alteration selected from one or more changes in the configuration selected from the P wave, the ST segment, the T wave, the QRS complex, the Q wave, the delta wave, and the U wave.

Other conditions which may be alleviated by administration of an effective dose of a peptide according to the invention are the effect of electrolyte derangement on the organ (e.g. the heart) as well as the derangement itself, including abnormalities in the relative concentrations of individual ions one to another. Such condition includes an abnormal serum concentration of one or more of the electrolytes selected from the group consisting of potassium, calcium, sodium, and magnesium According to the present invention, the tissue that may be affected includes one or more cell types present in the organ and may be selected from epithelial cells, macrophages, the reticulo endothelial system monocytes, neutrophil granulocytes, eosinophil granulocytes, basophil granulocytes, T-cells, B-cells, mast cells, and dendritic cells. Especially, the T-cells, B-cells, and mast cells may be of certain interest in this respect.

A preferred aspect of the invention relates to prevention or treatment wherein a dose of α-MSH analogue according to the invention is administered prophylactically for preventing a progress of the condition or of any symptom of the condition.

A preventive or prophylactic treatment may be an ongoing treatment during e.g. surgery or for the prevention of heart attacks in a patient suffering from coronary stenosis. The preventive treatment may also be for a limited period. The skilled person will be able to evaluate the specific treatment schedule based on the actual situation. In a preferred embodiment, the treatment or prevention is able to reduce the infarction size upon ischemia of the coronary arteries. Such infarction size may be reduced by 20%, such as at least 30%, preferably by at least 50% compared to the untreated individual.

Accordingly, the dose of a α-MSH analogue according to the invention is administered prophylactically for prevention of the establishment of the condition or of any symptom of the condition.

The dose of a α-MSH analogue according to the invention may be administered as a single dosage, regular or continued administration, or as a sequential administration.

The administration may be systemic administration, local administration including use of drug target systems, cathedrals and implants, oral administration, parenteral administration, such as subcutaneous, intramuscular, intravenous administration, intraperitoneal administration, intrathecal administration, pulmonary administration e.g. by inhalation, topical administration, transmucosal administration, transdermal administration.

Accordingly, the administration includes systemic administration; injection into tissue or into a body cavity including joints; implantation into tissue or into a body cavity; topical application to the skin or to any gastrointestinal surface, or to a mucosal surface including the lining of body cavities.

As evident from the above, the present invention relates to the use of a peptide according to the invention for the preparation of a medicament for treatment or prevention of any of the conditions disclosed herein by any relevant route of administration.

Pharmaceutical Formulations and Compositions

The invention also relates to pharmaceutical compositions comprising one or more peptides according to the invention. Said pharmaceutical compositions may further comprise one or more pharmaceutical carriers. Furthermore, said pharmaceutical compositions may further comprise one or more pharmaceutically acceptable excipients The pharmaceutical compositions according to invention can be, but are not limited to, a parental, oral, topical, trans-mucosal or trans-dermal composition.

In the following examples, suitable compositions containing one or more peptides according to the invention are given. For the administration to an individual (an animal or a human) the substance(s) are preferably formulated into a pharmaceutical composition containing the substance(s) and, optionally, one or more pharmaceutically acceptable excipients.

The compositions may be in form of, e.g., solid, semi-solid or fluid compositions such as, e.g., but not limited to bioabsorbable patches, drenches, dressings, hydrogel dressings, hydrocolloid dressings, films, foams, sheets, bandages, plasters, delivery devices, implants, powders, granules, granulates, capsules, agarose or chitosan beads, tablets, pills, pellets, microcapsules, microspheres, nanoparticles, sprays, aerosols, inhalation devices, gels, hydrogels, pastes, ointments, creams, soaps, suppositories, vagitories, tooth pastes, solutions, dispersions, suspensions, emulsions, mixtures, lotions, mouthwashes, shampoos, enemas, kits containing e.g. two separate containers, wherein the first one of the containers contains a peptide according to the invention and the second container contains a suitable medium intended to be added to the first container before use in order to obtain a ready-to-use composition; and in other suitable forms such as, e.g., implants or coating of implants or in a form suitable for use in connection with implantation or transplantation.

The compositions may be formulated according to conventional pharmaceutical practice, see, e.g., "Remington: The science and practice of pharmacy" $20^{th}$ ed. Mack Publishing, Easton Pa., 2000 ISBN 0-912734-04-3 and "Encyclopedia of Pharmaceutical Technology", edited by Swarbrick, J. & J. C. Boylan, Marcel Dekker, Inc., New York, 1988 ISBN 0-8247-2800-9.

A pharmaceutical composition comprising an active substance serves as a drug delivery system. In the present context the term "drug delivery system" denotes a pharmaceutical composition (a pharmaceutical formulation or a dosage form), which upon administration presents the active substance to the body of a human or an animal. Thus, the term "drug delivery system" embraces plain pharmaceutical compositions such as, e.g., creams, ointments, liquids, powders, tablets, etc. as well as more sophisticated formulations such as sprays, plasters, bandages, dressings, devices, etc.

As mentioned above, a pharmaceutical composition for use according to the invention may comprise pharmaceutically or cosmetically acceptable excipients.

The choice of pharmaceutically acceptable excipients in a composition for use according to the invention and the optimum concentration thereof cannot generally be predicted and must be determined on the basis of an experimental determination thereof. Also whether a pharmaceutically acceptable excipient is suitable for use in a pharmaceutical composition is generally dependent on which kind of dosage form is chosen. However, a person skilled in the art of pharmaceutical formulation can find guidance in e.g., "Remington: The science and practice of pharmacy" $20^{th}$ ed. Mack Publishing, Easton Pa., 2000 ISBN 0-912734-04-3.

A pharmaceutically acceptable excipient is a substance, which is substantially harmless to the individual to which the composition will be administered. Such an excipient normally fulfils the requirements given by the national drug agencies. Official pharmacopeias such as the British Pharmacopeia, the United States of America Pharmacopeia and the European Pharmacopeia set standards for well-known pharmaceutically acceptable excipients.

In the following is given a review on relevant pharmaceutical compositions for use according to the invention. The review is based on the particular route of administration. However, it is appreciated that in those cases where a pharmaceutically acceptable excipient may be employed in different dosage forms or compositions, the application of a particular pharmaceutically acceptable excipient is not limited to a particular dosage form or of a particular function of the excipient.

Parenteral Compositions

For systemic application, the compositions according to the invention may contain conventionally non-toxic pharmaceutically acceptable carriers and excipients including microspheres and liposomes.

The compositions for use according to the invention include all kinds of solid, semisolid and fluid compositions. Compositions of particular relevance are e.g. solutions, suspensions, emulsions, gels, implantation tablets and implants.

The pharmaceutically acceptable excipients may include solvents, buffering agents, preservatives, humectants, chelating agents, antioxidants, stabilizers, emulsifying agents, suspending agents, gel-forming agents, diluents, disintegrating agents, binding agents, lubricants and wetting agents. For examples of the different agents see below.

Topical, Trans-mucosal and Trans-Dermal Compositions

For application to the mucosa or the skin, the compositions for use according to the invention may contain conventionally non-toxic pharmaceutically acceptable carriers and excipients including microspheres and liposomes.

The compositions for use according to the invention include all kinds of solid, semi-solid and fluid compositions. Compositions of particular relevance are e.g. pastes, ointments, hydrophilic ointments, creams, gels, hydrogels, solutions, emulsions, suspensions, lotions, liniments, resoriblets, suppositories, enema, pessaries, moulded pessaries, vaginal capsules, vaginal tablets, shampoos, jellies, soaps, sticks, sprays, powders, films, foams, pads, sponges (e.g. collagen sponges), pads, dressings (such as, e.g., absorbent wound dressings), drenches, bandages, plasters and transdermal delivery systems.

The pharmaceutically acceptable excipients may include solvents, buffering agents, preservatives, humectants, chelating agents, antioxidants, stabilizers, emulsifying agents, suspending agents, gel-forming agents, ointment bases, suppository bases, penetration enhancers, perfumes, skin protective agents, diluents, disintegrating agents, binding agents, lubricants and wetting agents. For examples of the different agents see below.

Oral Compositions

For application to the mucosa or the skin, the compositions for use according to the invention may contain conventionally non-toxic pharmaceutically acceptable carriers and excipients including microspheres and liposomes.

The composition for use according to the invention includes all kinds of solid, semi-solid and fluid compositions. Compositions of particular relevance are e.g. solutions, suspensions, emulsions, uncoated tablets, modified-release tablets, gastro-resistant tablets, orodispersible tablets, effervescent tablets, chewable tablets, soft capsules, hard capsules, modified release capsules, gastro-resistant capsules, uncoated granules, effervescent granules, granules for the preparation of liquids for oral use, coated granules, gastro-resistant granules, modified-release granules, powders for oral administration and powders for the preparation of liquids for oral use.

The pharmaceutically acceptable excipients may include solvents, buffering agents, preservatives, humectants, chelating agents, antioxidants, stabilizers, emulsifying agents, suspending agents, gel-forming agents, diluents, disintegrating agents, binding agents, lubricants, coating agents and wetting agents. For examples of the different agents see below.

Examples of Various Agents

Examples of solvents are but not limited to water, alcohols, vegetable or marine oils (e.g. edible oils like almond oil, castor oil, cacao butter, coconut oil, corn oil, cottonseed oil, linseed oil, olive oil, palm oil, peanut oil, poppyseed oil, rapeseed oil, sesame oil, soybean oil, sunflower oil, and teaseed oil), mineral oils, fatty oils, liquid paraffin, polyethylene glycols, propylene glycols, glycerol, liquid polyalkylsiloxanes, and mixtures thereof.

Examples of buffering agents are but not limited to citric acid, acetic acid, tartaric acid, lactic acid, hydrogenphosphoric acid, diethylamine etc.

Examples of preservatives for use in compositions are but not limited to parabens, such as methyl, ethyl, propyl p-hydroxybenzoate, butylparaben, isobutylparaben, isopropylparaben, potassium sorbate, sorbic acid, benzoic acid, methyl benzoate, phenoxyethanol, bronopol, bronidox, MDM hydantoin, iodopropynyl butylcarbamate, EDTA, benzalconium chloride, and benzylalcohol, or mixtures of preservatives.

Examples of humectants are but not limited to glycerin, propylene glycol, sorbitol, lactic acid, urea, and mixtures thereof.

Examples of chelating agents are but not limited to sodium EDTA and citric acid.

Examples of antioxidants are but not limited to butylated hydroxy anisole (BHA), ascorbic acid and derivatives thereof, tocopherol and derivatives thereof, cysteine, and mixtures thereof.

Examples of emulsifying agents are but not limited to naturally occurring gums, e.g. gum acacia or gum tragacanth; naturally occurring phosphatides, e.g. soybean lecithin; sorbitan monooleate derivatives; wool fats; wool alcohols; sorbitan esters; monoglycerides; fatty alcohols; fatty acid esters (e.g. triglycerides of fatty acids); and mixtures thereof.

Examples of suspending agents are but not limited to celluloses and cellulose derivatives such as, e.g., carboxymethyl cellulose, hydroxyethylcellulose, hydroxypropylcellulose, hydroxypropylmethylcellulose, carraghenan, acacia gum, arabic gum, tragacanth, and mixtures thereof.

Examples of gel bases and viscosity-increasing are but not limited to liquid paraffin, polyethylene, fatty oils, colloidal silica or aluminium, zinc soaps, glycerol, propylene glycol, tragacanth, carboxyvinyl polymers, magnesium-aluminium silicates, Carbopol®, hydrophilic polymers such as, e.g. starch or cellulose derivatives such as, e.g., carboxymethylcellulose, hydroxyethylcellulose and other cellulose derivatives, water-swellable hydrocolloids, carragenans, hyaluronates (e.g. hyaluronate gel optionally containing sodium chloride), and alginates including propylene glycol aginate.

Examples of ointment bases are but not limited to beeswax, paraffin, cetanol, cetyl palmitate, vegetable oils, sorbitan esters of fatty acids (Span), polyethylene glycols, and condensation products between sorbitan esters of fatty acids and ethylene oxide, e.g. polyoxyethylene sorbitan monooleate (Tween).

Examples of hydrophobic ointment bases are but not limited to paraffins, vegetable oils, animal fats, synthetic glycerides, waxes, lanolin, and liquid polyalkylsiloxanes.

Examples of hydrophilic ointment bases are but not limited to solid macrogols (polyethylene glycols).

Examples of powder components are but not limited to alginate, collagen, lactose, powder which is able to form a gel when applied to a wound (absorbs liquid/wound exudate).

Examples of diluents and disintegrating agents are but not limited to lactose, saccharose, emdex, calcium phosphates, calcium carbonate, calcium sulphate, mannitol, starches and microcrystalline cellulose.

Examples of binding agents are but not limited to saccharose, sorbitol, gum acacia, sodium alginate, gelatine, starches, cellulose, sodium coboxymethylcellulose, methylcellulose, hydroxypropylcellulose, polyvinylpyrrolidone and polyetyleneglycol.

Examples of wetting agents are but not limited to sodium laurylsulphate and polysorbate 80.

Examples of lubricants are but not limited to talcum, magnesium stearate, calcium stearate, silicium oxide, precirol and polyethylenglycol.

Examples of coating agents are but not limited to hydroxypropylcellulose, hydroxypropylmethylcellulose, polyvinylpropylidone, ethylcellulose and polymethylacrylates.

Examples of suppository bases are but not limited to oleum cacao, adeps solidus and polyethylenglycols.

The α-MSH analogue may be present in the medicament in an amount of 0.001-99%, typically 0.01-75%, more typically 0.1-20%, especially 1-15% such as 1-10% by weight of the medicament.

The dose depends on the condition to be treated. The individual drugs may be used in the doses known in the art. It is contemplated that the dose of the one or more peptides according to the invention will be in the range of 1 ng to 100 mg pr. kg body weight, typically 1 μg to 10 mg pr. kg body weight, more typically 10 μg to 1 mg pr. kg body weight, such as 50-500 μg pr. kg body weight.

In a still further aspect, the present invention relates to a pharmaceutical composition as described above comprising one or more peptides according to the invention optionally with a pharmaceutically acceptable carrier.

The pharmaceutical compositions according to the present invention may be prepared by use of conventional techniques known in the art and with conventional pharmaceutical carriers. Furthermore, the pharmaceutical composition may be in any form suitable for any of the uses as described herein.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosure of which are incorporated by reference in their entireties.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

With respect to the above description of the various aspects of the present invention and of the specific embodiments of these aspects it should be understood that any feature and characteristic described or mentioned above in connection with one aspect and/or one embodiment of an aspect of the invention also apply by analogy to any or all other aspects and/or embodiments of the invention described.

The invention will hereinafter be described by way of the following non-limiting Figures and Examples.

EXAMPLES

In the following the methods for testing the peptides of the invention are described in general. The results for the tested peptides are given in examples 1-7. The aim of the methods is to test the peptides of the invention for anti-inflammatory effects and ability to inhibit or prevent the cell/tissue/organ impairment or destruction occurring as a result of ischemia, inflammation or toxic effects of a drug.

An inflammatory response or an exacerbation in chronic inflammation is characterized by production of cell-derived mediators such as tumor necrosis factor α (TNF)-α, interleukins (IL-1β, IL-8), nitric oxide (NO), and free oxygen radicals, which eventually will induce widespread endothelial damage with loss of arteriolar tonus in systemic vessels, increased capillary permeability, sustained hypotension and organ dysfunction, which in the lung is associated with accumulation of leucocytes including neutrophils and eosinophils within the alveolar space. Lipopolysaccharide (LPS), released from infectious agents, plays a central role in the inflammatory response to infection by inducing a number of inflammatory mediators including TNF-α. Treatments with the ability to inhibit TNF-α production are therefore believed to have marked anti-inflammatory effects. The inventor is using LPS stimulation to produce an inflammatory response in a number of setups (see experimental setups 1-3) and the primary marker for an anti-inflammatory effect of the peptides according to the invention is the ability to inhibit TNF-α production.

Ischemia induced by reduced/complete arrest in arterial blood supply induces multiple tissue reactions including neutrophil accumulation, other inflammatory responses and cell death. Identification of compounds that could inhibit or prevent (either completely or partially) many of the cell/tissue/organ impairments or destructions occurring as a result of ischemia/inflammation is of great benefit. The inventor is using two models of temporarily ischemia: 1) the myocardial ischemia reperfusion model in rats, which mimics the development of acute myocardial infarction followed by restoration of blood supply as it is achieved by either fibrinolytic therapy or coronary angioplasty (Experimental setup 5); 2) bilateral renal artery occlusion, which induces acute renal failure (ARF) comparable to AFR induced by temporarily reduction in the renal blood supply as seen in patients undergoing major surgical interventions (an example could be surgical intervention due to abdominal aorta aneurism) (experimental setup 6).

Nephrotoxicity is a well-known side effect to cisplatin treatment. Though not necessarily dose limiting renal toxicity still affects the majority of patients and a significant decrease in glomerular filtration rate is observed during treatment. The renal toxicity of cisplatin is seen as a direct cytotoxic damage on the nephrons in the outer medulla especially in the S3 segment of the proximal tubules and in the thick ascending limb of the loop of Henle. Hence cisplatin treatment often results in tubular reabsorption defects including an impaired ability to dilute the urine. Hypomagnesemia is observed in approximately 50% of patients treated with cisplatin and is probably due to a defect in renal magnesium (Mg) reabsorption. A recent study has suggested that Mg supplementation is a crucial factor in protection against the nephrotoxic actions of Cyclosporin A and a possible relation between Mg loss and cisplatin induced nephrotoxicity has recently been suggested. Treatment aimed to prevent hypomagnesemia would therefore have beneficial effects in order not only to reduce the need of Mg supplementation, but also hi order to reduce the renal toxicity of cisplatin. The effect of the peptides according to the invention on cisplatin induced nephrotoxicity is examined in experimental setup 7.

Methods and Materials

The peptides of the present invention are the test compounds in the methods described below.

Experimental Setup 1

Inhibition of LPS Induced TNF-α Production by Human Leucocytes in vitro 20 mL human blood is collected in vacutainer tubes containing EDTA. PBMC is isolated using Ficoll-Paque Plus as in Amersham's Instruction 71-7167-00 AD, 2002-06. PBMC is counted using Tryphan Blue Solution (Sigma) and incubated in RPMI 1640, (Applichem), supplemented with 10 mM Hepes (Sigma), 2 mM L-glutamin (Sigma), 0.1% BSA (Sigma) and 50 U/50 μg/mL Penicillin/Streptomycin (Sigma) in the concentration $5\times10^5$ cells/mL. The isolated PBMC is incubated in a humidified 5% $CO_2$, 95% air atmosphere, at 37° C., in 24 well flat-bottomed plates (Corning Incorporated) with medium, 10 ng LPS/mL (Sigma), and test compound. After 18 hours the samples are centrifuged, and TNF-α in the supernatants is measured using Tumour Necrosis Factor Alpha [(h)TNF-α] from Human Biotrak ELISA System (Amersham).

The samples are incubated as following per donor:

PBMC's in RPMI (Time Control)
PBMC's with 10 ng LPS/mL (Vehicle)
PBMC's, 10 ng LPS/mL, $10^{-17}$M α-MSH or α-MSH analogue
PBMC's, 10 ng LPS/mL, $10^{-15}$M α-MSH or α-MSH analogue
PBMC's, 10 ng LPS/mL, $10^{-13}$M α-MSH or α-MSH analogue
PBMC's, 10 ng LPS/mL, $10^{-11}$M α-MSH or α-MSH analogue
PBMC's, 10 ng LPS/mL, $10^{-9}$M α-MSH or α-MSH analogue
PBMC's, 10 ng LPS/mL, $10^{-7}$M α-MSH or α-MSH analogue All samples are diluted from an initial stock solution between $1.4\times10^{-4}$M and $1.8\times10^{-3}$M. All solutions are handled in BSA coated vials in order to protect against binding of the compound to the surface of the vials.

Data is presented as mean±SE. The effect of test compounds on LPS induced TNF-α liberation is expressed as percentage of the TNF-α accumulation in the LPS-vehicle group. All comparisons are analysed with Student's unpaired t-test. Differences are considered significant at probability levels (p) of 0.05.

Experimental Setup 2
Inhibition of LPS Induced TNFα Production in Rats in vivo

Experimental Animals. Female Wistar rats (220-240 g) are obtained from the Charles River, Sulzfeld, Germany, and housed in a temperature—(22-24° C.) and moisture-controlled (40-70%) room with a 12 h light-dark cycle (light on from 6:00 A.M. to 6:00 P.M.). The rats are maintained on a standard rodent diet with 140 mmol/kg of sodium, 275 mmol/kg potassium and 23% protein (Altromin International, Lage, Germany) and have free access to water.

Animal Preparation. In isoflurane-nitrous oxide anesthesia, the animals are implanted with permanent medical grade Tygon catheters into the abdominal aorta and the inferior caval vein, respectively, via a femoral artery and vein. After instrumentation, the animals are housed individually for 7-10 days until the day of the experiment.

Experimental Protocol. Prior to the experiments all rats are adapted to the restraining cage used for the experiments by training them for two periods of two hours each. On the day of the experiment, the animal is transferred to a restraining cage, and an intravenous infusion of vehicle solution containing 150 mM glucose is started. The infusion rate is 0.5 ml/h throughout the experiment. After a short adaptation period, infusion of lipopolysaccharide (LPS) is started. LPS (E coli serotype 0127 B8, L 3129, Sigma, St. Louis, USA) is given at a dose of 4 mg/kg body weight delivered as an i.v. infusion over 1 hour. Arterial blood samples of 0.3 ml are taken 60, 90, and 120 minutes after start of the LPS infusion and replaced immediately with heparinized blood from a normal donor rat.

Experimental Groups:
In addition to LPS infusion all rats are treated with a bolus injection of:
Vehicle (0.5 mL isotonic saline);
α-MSH in one of the following doses: 50 µg/kg bw; 200 µg/kg/bw or 1000 µg/kg bw;
Test compound in one of the following doses: 50 µg/kg bw; 200 µg/kg/bw or 1000 µg/kg bw.

Measurement of TNF-α in Plasma: The blood samples are collected in a prechilled test tube with 0.5 mM EDTA, pH 7.4, and $20\times10^6$ IU/ml aprotinin. After centrifugation at 4° C., plasma samples are transferred to pre-chilled test tubes and stored at −20° C. for later measurements of TNF-α. TNF-α in plasma is determined by an ELISA (Biotrak, Amersham, UK).

Statistical Analyses. Results are presented as means±SE. A two-way ANOVA for repeated measures is used to test for differences between groups. In case of P<0.05, the differences between corresponding periods are evaluated by unpaired t-tests with Bonferroni's correction of the level of significance.

Experimental Setup 3
Inhibition of Neutrophil and Eosinophil Infiltration after LPS Inhalation in Rats.

Male Sprague-Dawley rats (weight ~200 g) from M&B A/S, DK-8680 Ry, Denmark, are used for all experiments. The rats are caged in standard cages type 3 and housed in a temperature—(22-24° C.) and moisture-controlled (40-70%) room with a 12 h light-dark cycle (light on from 6:00 A.M. to 6:00 P.M.). The diet is autoclaved Altromin 1324 special formulation, Produced by Altromin Denmark, Chr. Pedersen A/S, 4100 Ringsted, Denmark. Diet and water are administered ad libitum.

After acclimatization the rats are randomly allocated to the experimental groups and dosed i.v. with test compound at start of LPS-induction and once again 8 hours after LPS-induction.

Rats in groups of 3 are anaesthetized with 0.1 ml hypnorm/dormicum pr. 100 g and dosed i.v with the test compound. Immediately after dosing they are placed in the inhalation chamber where they are subjected to a nebulized LPS solution. The concentration of LPS is mg/ml. Dosing time is 15 minutes. The rats are euthanized 24 hours after dosing with the test substance. At termination the rats are eutanized with $CO_2/O_2$.

Then bronchoalveolar lavage is performed by installing and withdrawing 6×2.5 ml of PBS to the right lung. Lavage is done with the lungs remaining in the thorax after removing sternum and costae. The connection to the left lung is tied off during this procedure. Bronchoalveolar fluid (BALF) is centrifuged at 1000 rpm at 4° C. for 10 minutes. After removing the supernatant the cell pellet is resuspended in 0.5 ml PBS and total cell count performed. Two smears of BALF stained with May-Grüwald Giemsa stain is made from each rat. BALF from each rat is subjected to total cell count and to differential count of leucocytes.

Experimental Groups:
In addition to LPS infusion all rats are treated with bolus injections of either:
Vehicle (0.5 mL isotonic saline);
α-MSH: 200 µg/kg/bw
α-MSH analogue: 200 µg/kg/bw
Finally a time control group without LPS inhalation is treated with Vehicle.

Statistics
Data are presented as mean±S.E. Between group comparisons are performed by one way analysis of variance followed by Fishers Least Significant Difference test. Differences are considered significant at the 0.05 level.

Experimental Setup 4
Inhibition of LPS Induced Cytokine Release and Pulmonary Hypertension in Pigs in vivo.

Female Landrace pigs (~30 kg) are fasted overnight but allowed free access to water. Then the pigs are premedicated with intramuscular ketamine (10 mg/kg) and midazolam (0.25 mg/kg). Anesthesia is induced with intravenous ketamine (5 mg/kg). The pigs are orally intubated, and anesthesia is maintained with a continuous intravenous infusion of fentanyl (60 µg/kg/h and midazolam (6 mg/kg/h). The animals are ventilated with a volume-controlled ventilator (Servo 900 ventilator; Siemens Elema, Solna, Sweden) with a positive end-expiratory pressure of 5 cm $H_2O$. Tidal volume is kept at 10-15 ml/kg, and the respiratory rate adjusted (20-25 breaths/min) to maintain normocapnia (arterial carbon dioxide tension [$PaCO_2$] in the range of 34-45 mmHg). Ventilation is performed with oxygen in air aimed tot reach an arterial oxygen tension ($PaO_2$) higher than 105 mmHg. One arterial and 2 venous sheaths are placed in the carotid artery and corresponding veins for infusion, blood pressure measurements through fluid filled catheter, blood sampling and for introducing catheters.

A Swan-Ganz catheter (Edwards Lifescience Corp., Irvine, Calif.) is inserted in the pulmonary artery via the right cava superior vein. Localization of the balloon-tipped catheter is determined by observing the characteristic pressure trace on the monitor as it is advance through the right side of the heart into the pulmonary artery as well as by x-ray. Another catheter (5 French; St. Jude Medical Company, St. Paul, Minn.) is inserted into the left carotid artery for continuous blood pressure monitoring and blood sampling. A urine catheter is inserted for urine collection. A temporary pace catheter is inserted through the venous sheath to the right atrium (x-ray guided) to standardise heart rate, when assessing cardiac performance Hemodynamic Monitoring. Continuous observations is performed of arterial blood pressure, heart rate (from the electrocardiogram), and pulmonary artery pressure (PAP).

Lipopolysaccharide Infusion. *Escherichia coli* lipopolysaccharide endotoxin, (*E. coli* 026:_6, Bacto Lipopolysaccharides; Difco Laboratories, Detroit, Mich.) is dissolved in saline min before each experiment to dissolve any precipitate. After a stabilization period, lipopolysaccharide infusion is started at baseline at a rate of 2.5 μg/kg/h and increased stepwise to 15 μg/kg/min during 30 min. After this, the fusion was kept at a rate of 2.5 μg/h kg/h during 150 min and thereafter discontinued.

Interventional Groups: The control group is given vehicle in equal volume to the intervention group immediately before LPS infusion is initiated. The interventional group is given a dose of α-MSH analogue, 200 μg/kg, as a single intravenous bolus injection.

Cytokines. Fresh frozen plasma samples (−80° C.) obtained from EDTA-stabilized blood is used for measurements of TNFα by use of commercial available enzyme-linked immunosorbent assays according to the manufacturer's instructions.

Statistics. Data are presented as mean±S.E. Between group comparisons are performed by one way analysis of variance followed by Fishers Least Significant Difference test. Differences are considered significant at the 0.05 level.

Experimental Setup 5
Inhibition of Myocardial Infarction Size, Induced by 60 Minutes Occlusion of the Left Anterior Descending Coronary Artery in Rats.

Barrier-bred and specific pathogen-free female Wistar rats (250 g) are obtained from Charles River, Hannover, Germany. The animals are housed in a temperature (22-24° C.) and moisture (40-70%) controlled room with a 12-hour light-dark cycle (light on from 6:00 A.M. to 6:00 P.M.). All animals are given free access to tap water and a pelleted rat diet containing approximately 140 mmol/kg of sodium, 275 mmol/kg potassium and 23% protein (Altromin catalogue no. 1310, Altromin International, Lage, Germany).

The rats are instrumented with permanent medical grade Tygon catheters in the inferior caval vein and the abdominal aorta via the femoral vein and artery. One week later the Rats are anaesthetized in an inhalation chamber with 4% isoflurane in $O_2$. After insertion of an endotracheal tube the animal is artificially ventilated with 1.0% isoflurane in $O_2$ using of Hugo Basile Rodent ventilator. Tidal volume is 8-10 ml/kg b.w. and respiratory rate 75 min$^{-1}$, which maintains arterial pH between 7.35 and 7.45. During surgery the animal is placed on a heated table that maintains rectal temperature at 37-38° C. Standard ECG (second lead) is measured using a Hugo Sachs ECG Coupler and collected on line at 4,000 Hz in PowerLab. After parasternal thoracotomy and opening of the pericardium the left anterior descending coronary artery (LAD) is localized visually. An atraumatic 6-0 silk suture with an occluder that allows reopening of the ligature is placed around the LAD between the pulmonary trunk and the lower right end of the left auricle. After 10 minutes the left anterior descending coronary artery (LAD) is occluded. Successful occluding is confirmed by alterations in ECG (ST-segment elevation and increase in R-wave amplitude) and by fall in MAP. Reperfusion is made after 60 minutes by opening the occluder. Control rats are sham-operated.

The rats are subjected to one of the following i.v treatments:
Vehicle: 0.5 ml 150 mM NaCl.
α-MSH: 200 μg or 1000 μg α-melanocyte stimulating hormone/kg b.w. in 0.5 ml 150 mM NaCl.
Test compound 200 μg or 1000 μg test compound/kg b.w. in 0.5 ml 150 mM NaCl. Treatment is given 5 minutes prior to reperfusion.

Determination of the Size of the Ischemic and Necrotic Myocardium

The rats are kept anaesthetized after the ischemia/reperfusion and re-occluding of the LAD is performed after three hours reperfusion. During this period ECG and MAP are measured continuously. Then Evans Blue dye (1 ml; 2% w/v) is administered i.v. to determine the size of the ischemic area. The heart is removed and cut into horizontal slices to determine the size of the ischemic area and to separate the ischemic myocardium from the non-ischemic myocardium. The ischemic area is isolated and incubated in a 0.5% triphenyltetrazolium chloride solution for 10 minutes at 37° C. The size of the necrotic tissue is then measured by used of a computerized image program. An additional setup of animals are treated with buprenorphine post-surgical and returned to there cages for measurement of left ventricular end diastolic pressure (LVEDP) two weeks later in order to evaluate the effect of the pharmacological treatment on the development of congestive heart failure. LVEDP is measured using a 2F microtip catheters inserted into the left ventricle via the right carotid artery. Isoflurane concentration is adjusted to stabilize mean arterial pressure (MAP) at 85-90 mmHg.

Statistics

Data are presented as mean±S.E. Within group comparisons are analysed with Student's paired t test. Between group comparisons are performed by one way analysis of variance followed by Fishers Least Significant Difference test. Differences are considered significant at the 0.05 level.

Experimental Setup 6
Inhibition of Renal Failure Induced by 40 Minutes Bilateral Occlusion of the Renal Arteries in Rats Barrier-bred and specific pathogen-free female Wistar rats (250 g) are obtained from Charles River, Hannover, Germany. The animals are housed in a temperature (22-24° C.) and moisture (40-70%) controlled room with a 12-hour light-dark cycle (light on from 6:00 A.M. to 6:00 P.M.). All animals are given free access to tap water and a pelleted rat diet containing approximately 140 mmol/kg of sodium, 275 mmol/kg potassium and 23% protein (Altromin catalogue no. 1310, Altromin International, Lage, Germany).

The rats, which previously have been instrumented with a chronic venous catheter, are placed in metabolic cages and after a two days acclimation period to the metabolic cages, experimental ARF is induced by occlusion of both renal arteries for 60 min. During surgery, the rats are anesthetized with isoflurane-nitrous oxide and placed on a heated table to maintain rectal temperature at 37° C. Both kidneys are exposed through flank incisions, mobilized by being dissected free from the perirenal fat, then a small portion of the renal artery is gently dissected from the vein. The renal arteries are occluded with a smooth surfaced vascular clip (60 g pressure; World Precision Instruments, UK) for 40 min. Total ischemia is confirmed by observing blanching of the entire kidney surface. During the period of ischemia, the wounds are closed temporarily to maintain body temperature. After the clips are removed, the kidneys are observed for additional 2-5 min. to ensure color change, indicating blood reflow. Then the wound are closed with 3-0 silk ligatures. The rats returned to the metabolic cages, and daily 24 h urine output and water intake are measured for five days. As a control group, rats are subjected to sham operations identical to the ones used for ARF rats without occlusion of the renal arteries. Sham-operated rats are monitored in parallel with rats with ARF.

The rats are subjected to one of the following i.v treatments:

Vehicle: 0.5 ml 150 mM NaCl.

α-MSH: 200 μg α-melanocyte stimulating hormone/kg b.w. in 0.5 ml 150 mM NaCl.

Test compound: 200 μg test compound/kg b.w. in 0.5 ml 150 mM NaCl. Treatment is given 5 minutes prior to reperfusion of the kidney and subsequently 6 and 24 hours later.

Statistics

Data are presented as mean±S.E. Within group comparisons are analysed with Student's paired t test. Between group comparisons are performed by one way analysis of variance followed by Fishers Least Significant Difference test. Differences are considered significant at the 0.05 level.

Experimental Setup 7

Inhibition of Cisplatin Induced Renal Failure

Rats, which previously have been instrumented with a chronic venous catheter, are placed in metabolic cages and after a period of acclimation to the metabolic cages the rats are treated with an intreperitoneal cisplatin injection 5.0 mg/kg bw in 0.5 ml 150 mM NaCl or vehicle (0.5 ml 150 mM NaCl). Five days later the rats are then returned to metabolic cages, and daily 24 h urine output and water intake are measured and collected for the next five days. All rats are then anesthetized in halothan/$N_2O$ and an arterial blood sample collected in prechilled EDTA coated vials. The blood samples are collected in a prechilled test tube with 0.5 mM EDTA, pH 7.4, and $20 \times 10^6$ IU/ml aprotinin. After centrifugation at 4° C., plasma samples are transferred to pre-chilled test tubes and stored at −20° C. for later measurements of creatinine and Magnesium (Mg). In addition to this creatinine is also measured in the urine collected in the last 24 hours period prior to the blood collection. Creatinine clearance ($C_{cr}$), used as an index of glomerular filtration rate (GFR), can then be calculated as the $C_{cr} = V_u \times U_{cr}/P_{cr}$, where $V_u$ is 24 hours urine production; $U_{cr}$ is the creatinine concentration on the urine and $P_{cr}$ is the creatinine concentration in plasma. Measurement of creatinine in urine and plasma is performed by use of the clinical chemistry systems VITROS 950 (Ortho-Clinical Diagnostics Inc., Johnson & Johnson, NJ) and Roche Hitachi Modular (Roche Diagnostics, Mannheim, Germany).

The rats are subjected to one of the following i.v treatments:

Vehicle: 0.5 ml 150 mM NaCl

α-MSH: 200 μg α-melanocyte stimulating hormone/kg b.w. in 0.5 ml 150 mM NaCl.

Test compound: 200 μg test compound/kg b.w. in 0.5 ml 150 mM NaCl. Treatment is given 5 minutes prior to reperfusion of the kidney and subsequently 6 and 24 hours later.

Statistics

Data are presented as mean±S.E. Within group comparisons are analysed with Student's paired t test. Between group comparisons are performed by one way analysis of variance followed by Fishers Least Significant Difference test. Differences are considered significant at the 0.05 level.

Results

Example 1

Test compound is α-MSH analogue #1:

The compound is tested in experimental setup 1-7.

Inhibition of LPS Induced TNF-α Production by Human Leucocytes in vitro

Figure 1:
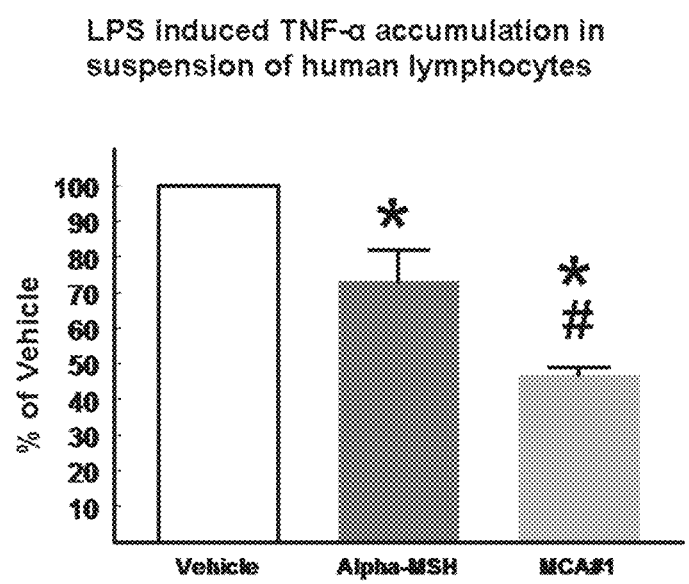
FIG. 1 LPS Induced TNF-α Accumulation in Suspension of Human Lymphocytes

Both α-MSH and the α-MSH analogue #1 (SEQ ID NO.1*) dose dependently reduce LPS induced TNF-α accumulation in the human leucocyte suspension. Surprisingly, the inhibitory effect of the α-MSH analogue #1 (SEQ ID NO.1*) is markedly more pronounced that the anti-inflammatory effect of the native peptide α-MSH. α-MSH inhibits the TNF-α accumulation to 73±9% of the maximal response (LPS-Vehicle). In contrast to this the α-MSH analogue #1 (SEQ ID NO.1*) is able to reduce the TNF-α accumulation to 47±2% of vehicle (P<0.01 vs αMSH) (see FIG. 1).

Inhibition of LPS Induced TNF-α Production in Rats in vivo

Both α-MSH and the α-MSH analogue #1 (SEQ ID NO.1*) reduce TNF-α accumulation in rats during iv infusion of LPS. The maximal inhibitory effect of α-MSH as well as the α-MSH analogue #1 (SEQ ID NO.1*) is achieved at a dose of 200 μg/kg body weight and the maximal inhibitory effect on TNF-α production is shown 120 minutes after initiation of the LPS infusion. Surprisingly, the inhibitory effect of the α-MSH analogue #1 (SEQ ID NO.1*) is markedly more pronounced that the anti-inflammatory effect of the native peptide α-MSH. Whereas α-MSH inhibits the TNF-α concentration in the rats plasma to 17±3% of the maximal response (LPS-Vehicle), the α-MSH analogue #1 (SEQ ID NO.1*) is able to reduce the TNF-α accumulation to 9±1% of vehicle (P=0.05 vs α-MSH) (see FIG. 2).

Figure 3:
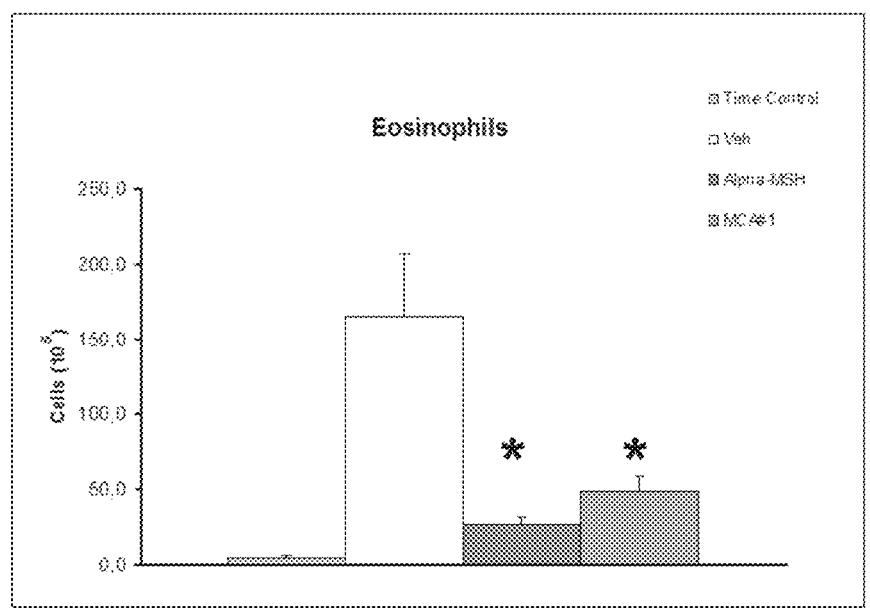

Inhibition of Neutrophil and Eosinophil Infiltration after LPS Inhalation in Rats Both α-MSH and the α-MSH analogue #1 (SEQ ID NO.1*) reduce the inflammatory response to LPS inhalation within the alveolar space as shown by a marked reduction of eosinophils in the BALF collected 24 hours after LPS inhalation. α-MSH treatment reduces the number of eosinophils within the BALF to $26.7 \pm 4.3 \times 10^5$ cells (P vs Vehicle<0.05) and the α-MSH analogue #1 (SEQ ID NO.1*) reduces the number of eosinophils to $49.0 \pm 10.5 \times 10^5$ cells (P vs Vehicle<0.05) compared to vehicle treated rats where the number of eosinophils within the BALF are $164.6 \pm 42.2 \times 10^5$ cells (see FIG. 3). In agreement with the above, the effect of the number of neutrophils within the BALF is similar for α-MSH and the α-MSH analogue #1 (SEQ ID NO.1*).

Inhibition of LPS Induced Cytokine Release and Pulmonary Hypertension in Pigs in vivo.

The α-MSH analogue #1 (SEQ ID NO.1*) has marked anti-inflammatory effects shown by a marked reduction in plasma concentrations of TNFα after LPS infusion in pigs treated with α-MSH analogue #1 (SEQ ID NO.1*). In addition to this anti-inflammatory effect, the α-MSH analogue #1 (SEQ ID NO.1*) surprisingly also has the ability to protects against development of pulmonary hypertension as evidenced by a marked attenuation in LPS induced increases in PAP found in the rats treated with α-MSH analogue #1 (SEQ ID NO.1*) (maximal increase in PAP: Vehicle: 22±4 mmHg vs α-MSH analogue #1 (SEQ ID NO.1*): 8±2 mmHg; p=0.05) (See FIG. 4).

Inhibition of Myocardial Infarction Size, Induced by 60 Minutes Occlusion of the Left Anterior Descending Coronary Artery in Rats

```
Ac-Lys-Lys-Lys-Lys-Lys-Lys-Ser-Tyr-Ser-Met-Glu-His-Phe-Arg-Trp-Gly-Lys-Pro-
Val-NH2
(SEQ ID NO. 1 *acetylated in the N-terminal and amidated in the C-terminal)
```

In contrast to α-MSH the α-MSH analogue #1 (SEQ ID NO.1*) surprisingly reduces the myocardial infarction size expressed as the necrotic area as fraction of the area of risk measured 3 hours after LAD-reperfusion. The maximal inhibitory effect of the α-MSH analogue #1 (SEQ ID NO.1*) is achieved at a dose of 200 µg/kg body weight where the reduction in infarction size is ~30% compared to Vehicle treated rats (Vehicle: 50.6±2.6% of area of risk vs α-MSH analogue #1 (SEQ ID NO.1*): 35.7±5.6% of area of risk, p=0.01). At the dose of 1000 µg/kg body weight the reduction in infarction size is also ~30% compared to Vehicle treated rats (α-MSH analogue #1 (SEQ ID NO.1*): 35.0±4.4% of area of risk, p<0.01 vs Vehicle) (See FIG. 5). Measurement of left ventricular end diastolic pressure (LVEDP) in an additional setup of animals 14 days after the 60 minutes occlusion of LAD, show that the beneficial effect of α-MSH analogue #1 (SEQ ID NO.1*) of infarctions size was associated with a marked reduction in LVEDP and thereby the development of post-infarctional congestive heart failure (LVEDP: α-MSH analogue #1 (SEQ ID NO.1*): 10.4±2.9 mmHg; vs Vehicle: 20.0±2.2 mmHg; P<0.01; vs Time control: 7.5±2.3 mmHg; NS) (see FIG. 6).

Figure 7:
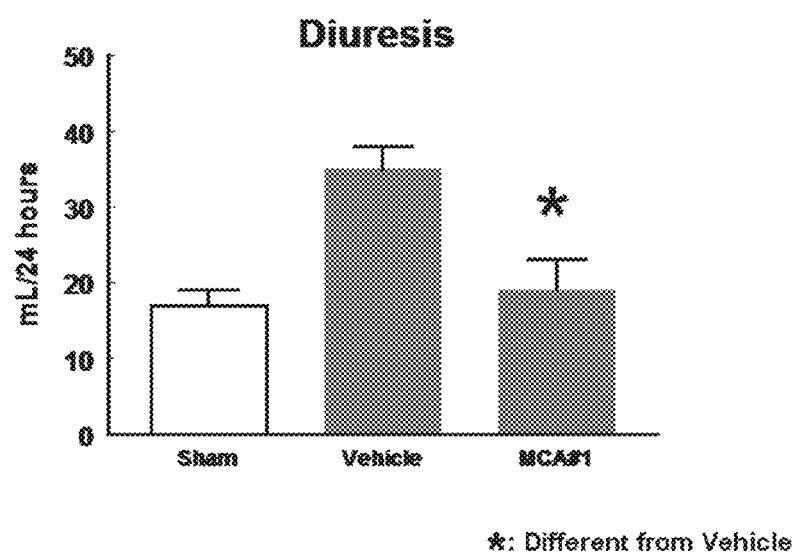

Inhibition of Renal Failure Induced by 40 Minutes Bilateral Occlusion of the Renal Arteries in Rats The 60 minutes bilateral renal ischemia (RIR) induces marked post ischemic polyuria. RIR rats have sustained polyuria, which at 5 day after the ischemic insult is increased by 101% compared to the sham-operated control rats (RIR-Vehicle: 34.8±3.3 ml/24 hours vs time-control: 17.3±2.1 ml/24 hours, p<0.01). α-MSH treatment is unable to reduce the polyuria (RIR-α-MSH: 29.0±2.9 ml/24 hours; NS vs RIR-Vehicle). Surprisingly, the α-MSH analogue #1 (SEQ ID NO.1*) is able induce a complete normalization of urine flow rate (RIR-α-MSH analogue #1 (SEQ ID NO.1*): 18.8±3.6 ml/24 hours; NS vs time-control; P<0.01 vs RIR-Vehicle) (see FIG. 7).

Inhibition of Cisplatin Induced Renal Failure

Cisplatin treatment induces marked hypomagnesemia and nephrotoxicity as evidenced by at fall in GFR. In accordance with this the rats treated with cisplatin and vehicle induced hypomagnesemia (Plasma Mg: 0.61±0.04 mM vs control rats: 0.77±0.05 mM, P<0.05) and a marked fall in GFR. Plasma Mg is also reduced in the rats treated with cisplatin and α-MSH (0.37±0.04 mM, P<0.05 vs control rats). Surprisingly, treatment with the α-MSH analogue #1 (SEQ ID NO.1*) prevents cisplatin induced hypomagnesemia (0.84±0.04 mM, NS vs control rats) and prevents the cisplatin induced fall in GFR.

Example 2

Test compound is α-MSH analogue #2:

The compound is tested in experimental setup 1-3 and 5-7.
Inhibition of LPS Induced TNF-α Production by Human Leucocytes in vitro Both α-MSH and the α-MSH analogue #2 (SEQ. NO. 5*) dose dependently reduce LPS induced TNF-α accumulation in the human leucocyte suspension. Surprisingly, the inhibitory effect of the α-MSH analogue #2 (SEQ. NO. 5*) is markedly more pronounced than the anti-inflammatory effect of the native peptide α-MSH. α-MSH inhibits the TNF-α accumulation to 73±9% of the maximal response (LPS-Vehicle). In contrast to this the α-MSH analogue #2 (SEQ. NO. 5*) is able to reduce the TNF-α accumulation to 42±11% of vehicle (P<0.01 vs α-MSH) (see FIG. 8).

Inhibition of LPS Induced TNF-α Production in Rats in vivo

Both α-MSH and the α-MSH analogue #2 (SEQ. NO. 5*) reduce TNF-α accumulation in rats during iv infusion of LPS. The maximal inhibitory effect of α-MSH as well as the α-MSH analogue #2 (SEQ. NO. 5*) is achieved at a dose of 200 µg/kg body weight. Surprisingly, the inhibitory effect of the α-MSH analogue #2 (SEQ. NO. 5*) is markedly more pronounced than the anti-inflammatory effect of the native peptide α-MSH. Whereas α-MSH inhibits the TNF-α concentration in the rats plasma to 17±3% of the maximal response (LPS-Vehicle), the α-MSH analogue #2 (SEQ. NO. 5*) is able to reduce the TNF-αaccumulation to 9±1% of vehicle (P<0.05 vs α-MSH) (see FIG. 9).

Inhibition of Neutrophil and Eosinophil Infiltration after LPS Inhalation in Rats Both α-MSH and the α-MSH analogue #2 (SEQ. NO. 5*) reduce the inflammatory response to LPS inhalation within the alveolar space as shown by a marked reduction of eosinophils in the BALF collected 24 hours after LPS inhalation. α-MSH treatment reduces the number of eosinophils within the BALF to $26.7 \pm 4.3 \times 10^5$ cells (P vs Vehicle<0.05) and the α-MSH analogue #2 (SEQ. NO. 5*) reduces the number of eosinophils to $34.0 \pm 8.6 \times 10^5$ cells (P vs Vehicle<0.05) compared to vehicle treated rats where the number of eosinophils within the BALF are $164.6 \pm 42.2 \times 10^5$ cells (see FIG. 10). Surprisingly, the α-MSH analogue #2 (SEQ. NO. 5*) has much more pronounced inhibitory effects on neutrophils within the BALF than α-MSH (α-MSH analogue #2 (SEQ. NO. 5*): $9.1 \pm 2.4 \times 10^5$ cells vs α-MSH: $20.1 \pm 2.5 \times 10^5$ cells; P<0.05) (see FIG. 11).

Inhibition of Myocardial Infarction Size, Induced by 60 Minutes Occlusion of the left anterio descending coronary artery in rats In contrast to α-MSH the α-MSH analogue #2 (SEQ. NO. 5*) surprisingly reduces the myocardial infarction size expressed as the necrotic area as fraction of the area of risk measured 3 hours after LAD-reperfusion. The maximal inhibitory effect of the α-MSH analogue #2 (SEQ. NO. 5*) is achieved at a dose of 200 µg/kg body weight where the reduction in infarction size is ~27% compared to Vehicle treated rats (Vehicle: 51.4±2.1% of area of risk vs α-MSH analogue #2 (SEQ. NO. 5*): 37.4±5.1% of area of risk,

```
Ac-Lys-Lys-Lys-Lys-Lys-Lys-Ser-Tyr-Ser-Nle-Glu-His-(D-Phe)-Arg-Trp-Gly-Lys-
Pro-Val-NH2
(SEQ. NO. 5 *acetylated in the N-terminal and amidated in the C-terminal)
```

The α-MSH analogue #2 (SEQ. NO. 5) differs from α-MSH analogue #1 (SEQ ID NO.1*) by substitution of Met with Nle at position 10 and by stereochemical substitution of Phe with (D-Phe) at position 13.

p=0.01) (See FIG. 12). Measurement of left ventricular end diastolic pressure (LVEDP) in an additional setup of animals 14 days after the 60 minutes occlusion of LAD, show that the beneficial effect of α-MSH analogue #2 (SEQ. NO. 5*) of infarctions size is associated with a marked reduction in LVEDP and thereby the development of post-infarctional congestive heart failure.

Inhibition of Renal Failure Induced by 40 Minutes Bilateral Occlusion of the Renal Arteries in Rats The 60 minutes bilateral renal ischemia (RIR) induces marked post ischemic polyuria. RIR rats have sustained polyuria, which at 5 day after the ischemic insult is increased by 101% compared to the sham-operated control rats (RIR-Vehicle: 34.8±3.3 ml/24 hours vs time-control: 17.3±2.1 ml/24 hours, p<0.01). α-MSH treatment is unable to reduce the polyuria (RIR-αMSH: 29.0±2.9 ml/24 hours; NS vs RIR-Vehicle) in contrast to this treatment with the α-MSH analogue #2 (SEQ. NO. 5*) markedly reduces the degree of polyuria found after RIR.

Inhibition of Cisplatin Induced Renal Failure

Cisplatin treatment induces marked hypomagnesemia and nephrotoxicity as evidenced by at fall in GFR. In accordance with this the rats treated with cisplatin and vehicle develops hypomagnesemia (Plasma Mg: 0.61±0.04 mM vs control rats: 0.77±0.05 mM, P<0.05) associated with a fall in GFR. Plasma Mg is also reduced in the rats treated with cisplatin and α-MSH (0.37±0.04 mM, P<0.05 vs control rats). In contrast to this, the α-MSH analogue #2 (SEQ. NO. 5*) prevents cisplatin induced hypomagnesemia as well as the cisplatin induced fall in GFR.

Example 3

Test compound is α-MSH analogue #3:

```
Ac-Lys-Lys-Lys-Lys-Lys-Lys-Ser-Tyr-Ser-Nle-Glu-His-D-Nal-Arg-Trp-Gly-Lys-Pro-
Val-NH2
(SEQ ID NO. 9 *acetylated in the N-terminal and amidated in the C-terminal)
```

The α-MSH analogue #3 (SEQ. NO. 9) differs from α-MSH analogue #1 (SEQ ID NO.1*) by substitution of Met wilt Nle at position 10 and by substitution of Phe with D-Nal at position 13.

The compound is tested in experimental setup 1, 2 and 5.

Inhibition of LPS Induced TNF-α Productin by Human Leucocytes in vitro

Both α-MSH and the α-MSH analogue #3 (SEQ ID NO.9*) dose dependently reduce LPS induced TNF-α accumulation in the human leucocyte suspension. Surprisingly, the inhibitory effect of the α-MSH analogue #3 (SEQ ID NO.9*) is markedly more pronounced than the anti-inflammatory effect of the native peptide α-MSH. α-MSH inhibits the TNF-αaccumulation to 73±9% of the maximal response (LPS-Vehicle). In contrast to this the α-MSH analogue #3 (SEQ ID NO.9*) is able to reduce the TNF-α accumulation to 53±13% of vehicle (P<0.05 vs α-MSH) (see FIG. 13).

Inhibition of LPS Induced TNF-α Production in Rats in vivo

Both α-MSH and the α-MSH analogue #3 (SEQ ID NO.9*) reduce TNF-α accumulation in rats during iv infusion of LPS. The maximal inhibitory effect of α-MSH as well as the α-MSH analogue #3 (SEQ ID NO.9*) is achieved at a dose of 200 µg/kg body weight. Surprisingly, the inhibitory effect of the α-MSH analogue #3 (SEQ ID NO.9*) is markedly more pronounced than the anti-inflammatory effect of the native peptide α-MSH. Whereas α-MSH inhibits the TNF-α concentration in the rats plasma to 17±3% of the maximal response (LPS-Vehicle), the α-MSH analogue #3 (SEQ ID NO.9*) is able to reduce the TNF-α accumulation to 11±3% of vehicle (P<0.05 vs αMSH) (see FIG. 14).

Inhibition of Myocardial Infarction Size, Induced by 60 Minutes Occlusion of the Left Anterior Descending Coronary Artery in Rats In contrast to α-MSH, the α-MSH analogue #3 (SEQ ID NO.9*) surprisingly reduces the myocardial infarction size expressed as the necrotic area as fraction of the area of risk measured 3 hours after LAD-reperfusion. The maximal inhibitory effect of the α-MSH analogue #3 (SEQ ID NO.9*) is achieved at a dose of 200 µg/kg body weight where the reduction in infarction size is ~24% compared to Vehicle treated rats (Vehicle: 51.3±2.1% of area of risk vs α-MSH analogue #3 (SEQ ID NO.9*): 39.0±3.4% of area of risk, p=0.05) (See FIG. 15). Measurement of left ventricular end diastolic pressure (LVEDP) in an additional setup of animals 14 days after the 60 minutes occlusion of LAD, show that the beneficial effect of α-MSH analogue #3 (SEQ ID NO.9*) on infarctions size is associated with a marked reduction in LVEDP and thereby the development of post-infarctional congestive heart failure.

Example 4

Test compound is α-MSH analogue #4:

```
Ac-Lys-Lys-Lys-Lys-Lys-Lys-Ser-Ser-Ile-Ile-Ser-His-Phe-Arg-Trp-Gly-Lys-Pro-Val-
NH2
(SEQ. NO. 13 *acetylated in the N-terminal and amidated in the C-terminal)
```

The α-MSH analogue #4 (SEQ. NO. 13) differs from α-MSH analogue #1 (SEQ ID NO.1*) by substitution of Tyr with Ser at position 8, by substitution of Ser with Ile at position 9, by substitution of Met with Ile in position 10 and by substitution of Glu with Ser in position 11.

The compound is tested in experimental setup 1 and 2.

Inhibition of LPS Induced TNF-α Production by Human Leucocytes in vitro

Both α-MSH and the α-MSH analogue #4 (SEQ. NO. 13*) dose dependently reduce LPS induced TNF-α accumulation in the human leucocyte suspension. Surprisingly, the inhibitory effect of the α-MSH analogue #4 (SEQ. NO. 13*) is markedly more pronounced than the anti-inflammatory effect of the native peptide α-MSH.

Inhibition of LPS Induced TNF-α Production in Rats in vivo

Both α-MSH and the α-MSH analogue #4 (SEQ. NO. 13*) reduce TNF-α accumulation in rats during iv infusion of LPS. The maximal inhibitory effect of α-MSH as well as the α-MSH analogue #4 is achieved at a dose of 200 µg/kg body weight. Surprisingly, the inhibitory effect of the α-MSH analogue #4 is markedly more pronounced than the anti-inflammatory effect of the native peptide α-MSH. Whereas α-MSH inhibits the TNF-α concentration in the rats plasma to 17±3% of the maximal response (LPS-Vehicle), the α-MSH analogue #4 (SEQ ID NO.13*) is able to reduce the TNF-α accumulation to 12±2% of vehicle (P<0.05 vs αMSH) (see FIG. 16).

Example 5

Test compound is α-MSH analogue #5:

```
Ac-Lys-Lys-Lys-Lys-Lys-Lys-Ser-Ser-Ile-Ile-Ser-His-(D-Phe)-Arg-Trp-Gly-Lys-
Pro-Val-NH2
(SEQ. NO. 17 *acetylated in the N-terminal and amidated in the C-terminal)
```

The α-MSH analogue #5 (SEQ. NO. 17) differs from α-MSH analogue #1 (SEQ ID NO.1*) by substitution of Tyr with Ser at position 8, by substitution of Ser with Ile at position 9, by substitution of Met with Ile in position 10, by substitution of Glu with Ser in position 11 and by stereochemical substitution of Phe with (D-Phe) at position 13.

The compound is tested in experimental setup 1 and 2.

Inhibition of LPS Induced TNF-α Production by Human Leucocytes in vitro

Both α-MSH and the α-MSH analogue #5 (SEQ. NO. 17*) dose dependently reduce LPS induced TNF-α accumulation in the human leucocyte suspension. Surprisingly, the inhibitory effect of the α-MSH analogue #5 (SEQ. NO. 17*) is markedly more pronounced than the anti-inflammatory effect of the native peptide α-MSH.

Inhibition of LPS Induced TNF-α Production in Rats in vivo

Both α-MSH and the α-MSH analogue #5 (SEQ. NO. 17*) reduce TNF-α accumulation in rats during iv infusion of LPS. The maximal inhibitory effect of α-MSH as well as the α-MSH analogue #5 (SEQ. NO. 17*) is achieved at a dose of 200 µg/kg body weight. Surprisingly, the inhibitory effect of the α-MSH analogue #5 (SEQ. NO. 17*) is markedly more pronounced that the anti-inflammatory effect of the native peptide α-MSH.

Example 6

Test compound is α-MSH analogue #6:

```
Ac-Glu-Glu-Glu-Glu-Glu-Glu-Ser-Tyr-Ser-Met-Glu-His-Phe-Arg-Trp-Gly-Lys-Pro-Val-NH2
(SEQ. NO. 2 *acetylated in the N-terminal and amidated in the C-terminal)
```

The α-MSH analogue #6 (SEQ. NO. 2) differs from α-MSH analogue #1 (SEQ ID NO.1*) by substitution of $(Lys)_6$ with $(Glu)_6$ at position 1-6

The compound is tested in experimental setup 1 and 2.

Inhibition of LPS Induced TNF-α Production by Human Leucocytes in vitro

Both α-MSH and the α-MSH analogue #6 (SEQ. NO. 2*) dose dependently reduce LPS induced TNF-α accumulation in the human leucocyte suspension. Surprisingly, the inhibitory effect of the α-MSH analogue #6 (SEQ. NO. 2*) is markedly more pronounced than the anti-inflammatory effect of the native peptide α-MSH.

Inhibition of LPS Induced TNF-α Production in Rats in vivo

Both α-MSH and the α-MSH analogue #6 (SEQ. NO. 2*) reduce TNF-α accumulation in rats during iv infusion of LPS. The maximal inhibitory effect of α-MSH as well as the α-MSH analogue #6 (SEQ. NO. 2*) is achieved at a dose of 200 µg/kg body weight. Surprisingly, the inhibitory effect of the α-MSH analogue #6 (SEQ. NO. 2*) is markedly more pronounced that the anti-inflammatory effect of the native peptide α-MSH.

Example 7

Test compound is α-MSH analogue #7:

```
Ac-Lys-Lys-Lys-Lys-Lys-Lys-Ser-Tyr-Ser-Met-Glu-His-Phe-Arg-Trp-Gly-Lys-Pro-
(D-Val)-NH2
(SEQ. NO. 3 *acetylated in the N-terminal and amidated in the C-terminal)
```

The α-MSH analogue #7 (SEQ. NO. 3) differs from α-MSH analogue #1 (SEQ ID NO.1*) by stereochemical substitution of Phe with (D-Val) at position 19.

The compound is tested in experimental setup 1 and 2.

Inhibition of LPS Induced TNF-α Production by Human Leucocytes in vitro

Both α-MSH and the α-MSH analogue #7 (SEQ. NO. 3*) dose dependently reduce LPS induced TNF-α accumulation in the human leucocyte suspension. Surprisingly, the inhibitory effect of the α-MSH analogue #7 (SEQ. NO. 3*) is markedly more pronounced than the anti-inflammatory effect of the native peptide α-MSH.

Inhibition of LPS Induced TNF-α Production in Rats in vivo

Both α-MSH and the α-MSH analogue #7 (SEQ. NO. 3*) reduce TNF-α accumulation in rats during iv infusion of LPS. The maximal inhibitory effect of α-MSH as well as the α-MSH analogue #7 (SEQ. NO. 3*) is achieved at a dose of 200 µg/kg body weight. Surprisingly, the inhibitory effect of the α-MSH analogue #7 (SEQ. NO. 3*) is markedly more pronounced that the anti-inflammatory effect of the native peptide α-MSH.

REFERENCES

U.S. Pat. No. 4,288,627
WO 91/17243
WO 99/46283
Beaucage, S. L. and Caruthers, M. H. Tetrahedron Letters 22, 1981, pp. 1859-1869
Bodanszky, M. and Bodanszky, A., "The Practice of Peptide Synthesis", 2. Ed, Springer-Verlag, 1994.
Catania, A., Rajora, F., Capsoni, F., Minonzio, R. A., Star, and Lipton, J. M. Peptides 17: 675-679, 1996.
Ehrlich, 1978, Proc. Natl. Acad. Sci. USA 75:1433).

Guo and Sherman, 1995, Molecular Cellular Biology 15:5983-5990.
Hartmeyer, M., Scholzen T., Becher E., Bhardwaj R. S., Schwarz T. and Luger T. A., J. Immunol., 159: 1930-1937, 1997.
Hiltz M. E. et al. (1991), Peptides, 12, 767-771.
Hruby V. J. et al. (1995), J. Med. Chem., 38, 3454-3461.
Jones, J. "The Chemical Synthesis of Peptides", Clarendon Press, 1991.
Kullmann, W. 1987, Enzymatic Peptide Synthesis, CRC Press, Boca Raton, Fla., pp. 41-59.
Lipton, J. M and Catania, A. Immunol. Today 18: 140-145. 1997
Liu et al., 1996, J. Am. Chem. Soc. 118:307-312 and Dawson et al., 1996, 226:776.
Luger, T. A., Scholzen T. and Grabbe S., J. Investig. Dermatol. Symp. Proc., 2: 87-93, 1997.
Matthes et al., EMBO Journal 3, 1984, pp. 801-805.
MANIATIS, T., E. F. FRITSCH and J. SAMBROOK, 1982 *Molecular Cloning: A Laboratory Manual*. Cold Spring Harbor Laboratory Press, Cold Spring Harbor, N.Y.
Remington: The science and practice of pharmacy" 20$^{th}$ ed. Mack Publishing, Easton Pa., 2000 ISBN 0-912734-04-3 and "Encyclopedia of Pharmaceutical Technology", edited by Swarbrick, J. & J. C. Boylan, Marcel Dekker, Inc., New York, 1988 ISBN 0-8247-2800-9.
Rajora, N., Boccoli, G., Catania and Lipton J. M., Peptides, 18: 381-385, 1997.
Remington: The science and practice of pharmacy" 20$^{th}$ ed. Mack Publishing, Easton Pa., 2000 ISBN 0-912734-04-3.
Rizzi A. et al. (2002), British Journal of Pharmacology, 137, 369-374.
Romanos et al., 1992, Yeast 8:423-488.
Sawyer T. K. (1980), Proc. Nat. Acad. Sci., 10, 5754-5758.
Schiöth H. B. et al. (1998), Eur. J. Pharm., 349, 359-366.
Star, R. A., Rajora N., Huang J., Stock R. C., Catania A. and Lipton J. M.; Proc. Natl. Acad. Sci. U.S.A, 92: 8016-8020, 1995.
Wong, K. Y., Rojora, G., Boccoli, A., Catania, A., and Lipton J. M., Neuroimmunomodulation, 4: 37-41, 1997.
"Useful proteins from recombinant bacteria" in Scientific American, 1980, 242:74-94

What is claimed is:

1. A method for preventing or reducing ischemia-induced acute renal failure, comprising administering to a subject in need thereof a peptide comprising the amino acid sequence of SEQ ID NO: 1 wherein said amino acid sequence is N-terminally acetylated and C-terminally amidated.

2. A method for preventing or reducing ischemia-induced acute renal failure, comprising administering to a subject in need thereof a peptide comprising the amino acid sequence of SEQ ID NO: 1, wherein said amino acid sequence is N-terminally acetylated and C-terminally amidated, and wherein said peptide is administered in an amount that is less than that required for native α-melanocyte-stimulating hormone to achieve the same effect.

3. A method of preventing or reducing ischemia-induced acute renal failure, comprising administering to a subject in need thereof a peptide comprising the amino acid sequence of SEQ ID NO: 1, wherein said amino acid sequence is N-terminally acetylated and C-terminally amidated, and wherein said peptide is administered in such an amount that the same amount of native α-melanocyte-stimulating hormone is less effective in preventing or reducing said failure.

* * * * *